US012534730B2

(12) United States Patent
Brown et al.

(10) Patent No.: US 12,534,730 B2

(45) **Date of Patent: *Jan. 27, 2026**

(54) COMPOSITIONS AND METHODS FOR INHIBITING GYS2 EXPRESSION

(71) Applicant: NOVO NORDISK A/S, Bagsværd (DK)

(72) Inventors: Bob D. Brown, Littleton, MA (US); Natalie Pursell, Westborough, MA (US); Henryk T. Dudek, Belmont, MA (US); Cheng Lai, Lexington, MA (US)

(73) Assignee: NOVO NORDISK A/S, Bagsværd (DK)

( * ) Notice: Subject to any disclaimer, the term of this patent is extended or adjusted under 35 U.S.C. 154(b) by 154 days.

This patent is subject to a terminal disclaimer.

(21) Appl. No.: 18/156,177

(22) Filed: Jan. 18, 2023

(65) Prior Publication Data

US 2023/0365974 A1 Nov. 16, 2023

Related U.S. Application Data

(63) Continuation of application No. 16/977,152, filed as application No. PCT/US2019/018189 on Feb. 15, 2019, now Pat. No. 11,572,562.

(60) Provisional application No. 62/637,574, filed on Mar. 2, 2018.

(51) Int. Cl.
*C12N 15/113* (2010.01)
*A61K 31/7088* (2006.01)

(52) U.S. Cl.
CPC ...... *C12N 15/1137* (2013.01); *A61K 31/7088* (2013.01); *C12N 2310/14* (2013.01); *C12N 2310/3519* (2013.01); *C12N 2310/533* (2013.01); *C12N 2320/11* (2013.01); *C12Y 204/01011* (2013.01)

(58) Field of Classification Search
None
See application file for complete search history.

(56) References Cited

U.S. PATENT DOCUMENTS

| | | | | |
|---|---|---|---|---|
| 8,513,207 | B2 * | 8/2013 | Brown | C12N 15/111 536/24.5 |
| 10,689,647 | B2 | 6/2020 | Brown et al. | |
| 11,572,562 | B2 | 2/2023 | Brown et al. | |
| 2003/0004122 | A1 | 1/2003 | Beigelman et al. | |
| 2005/0255487 | A1 | 11/2005 | Khvorova et al. | |
| 2006/0078902 | A1 | 4/2006 | Bunting et al. | |
| 2008/0113351 | A1 | 5/2008 | Naito et al. | |
| 2011/0105591 | A1 | 5/2011 | Feinstein et al. | |
| 2021/0062197 | A1 | 3/2021 | Brown et al. | |
| 2021/0115438 | A1 | 4/2021 | Bleicher et al. | |

FOREIGN PATENT DOCUMENTS

| | | | |
|---|---|---|---|
| WO | 2001075067 | A2 | 10/2001 |
| WO | 2004045543 | A2 | 6/2004 |
| WO | WO-2005001092 | A2 | 1/2005 |
| WO | 2010033225 | A2 | 3/2010 |
| WO | WO-2010105372 | A1 | 9/2010 |
| WO | 2013052677 | A1 | 4/2013 |
| WO | 2016057932 | A1 | 4/2016 |
| WO | WO-2016100401 | A1 | 6/2016 |
| WO | 2016183009 | A2 | 11/2016 |
| WO | WO-2017141109 | A1 | 8/2017 |
| WO | WO-2019168687 | A1 | 9/2019 |

OTHER PUBLICATIONS

Nutall et al. Archives of Biochemistry and Biophysics vol. 311 pp. 443-449 (Year: 1994).*
Bhanot et al. Leukemia 29:1555-1563 (Year: 2015).*
Dicerna Pharmaceuticals, Inc., "Taking RNAi under the skin," Nature.com. 2016:B12; Retrieved from the Internet: https://media.nature.com/original/magazine-assets/d43747-020-00189-y/d43747-020-00189-y.pdf.
Gusarov et al., "Glycogen controls Caenorhabditis elegans lifespan and resistance to oxidative stress," Nat Commun. 8:15868 (2017) [includes Supplementary Figures and Tables (2017).
Huang, "Preclinical and Clinical Advances of GalNAc-Decorated Nucleic Acid Therapeutics," Mol Ther Nucleic Acids. 2017;6:116-132.
International Search Report and Written Opinion issued by the United States Patent and Trademark Office as International Searching Authority for International Application No. PCT/US2019/018189, mailed Jul. 17, 2019 (13 pages).
Pursell et al., "Inhibition of Glycogen Synthase II with RNAi Prevents Liver Injury in Mouse Models of Glycogen Storage Diseases," Mol Ther. 2018; 26(7):1771-1782.

* cited by examiner

*Primary Examiner* — Brian Whiteman

(74) *Attorney, Agent, or Firm* — Foley Hoag LLP; Ariana D. Harris; Samantha N. Devenport

(57) ABSTRACT

This disclosure relates to oligonucleotides, compositions and methods useful for reducing GYS2 expression, particularly in hepatocytes. Disclosed oligonucleotides for the reduction of GYS2 expression may be double-stranded or single-stranded, and may be modified for improved characteristics such as stronger resistance to nucleases and lower immunogenicity. Disclosed oligonucleotides for the reduction of GYS2 expression may also include targeting ligands to target a particular cell or organ, such as the hepatocytes of the liver, and may be used to treat glycogen storage diseases (e.g., GSDIa, GSDIII, GSDIV, GSDVI, and GSDIX) and related conditions.

13 Claims, 14 Drawing Sheets

Specification includes a Sequence Listing.

COMPOSITIONS AND METHODS FOR INHIBITING GYS2 EXPRESSION

RELATED APPLICATION

This application is a continuation of U.S. application Ser. No. 16/977,152, filed Sep. 1, 2020, which is a 35 U.S.C. § 371 National Stage filing of PCT International Application No. PCT/US2019/018189, filed Feb. 15, 2019, which claims the benefit under 35 U.S.C. § 119(e) to U.S. Provisional Application No. 62/637,574, filed Mar. 2, 2018, and entitled "COMPOSITIONS AND METHODS FOR INHIBITING GYS2 EXPRESSION." The entirety of each application is incorporated herein by reference thereto.

FIELD OF THE INVENTION

The present application relates to oligonucleotides and uses thereof, particularly uses relating to the treatment of glycogen storage diseases and associated conditions.

REFERENCE TO THE SEQUENCE LISTING

The present application is being filed along with a Sequence Listing in electronic format. The Sequence Listing is provided as a file entitled 400930_013USD1_195876_SL.xml created on Jun. 26, 2023 which is 935,659 bytes in size. The information in electronic format of the sequence listing is incorporated herein by reference in its entirety.

BACKGROUND OF THE INVENTION

Glycogen is a complex sugar used by the body to store glucose. When the body requires more glucose to function, it normally breaks down the stored glycogen for use in cellular processes. Several enzymes participate in the processes that are used to store glucose as glycogen (glycogen synthesis) and break down glycogen to glucose (glycogen breakdown). When one or more of these enzymes are inhibited, it can result in a glycogen storage disease in which a dearth of glycogen storage, a buildup of glycogen in affected cells (e.g., liver and/or muscle cells), or the formation of abnormally structured glycogen may be observed. When a disorder of glycogen storage or breakdown occurs, those affected may suffer from a number of symptoms including, but not limited to: hepatomegaly, increased liver toxicity (e.g., higher levels of AST, ALT, and/or ALP), liver fibrosis, fatty acid deposition in the liver, hepatic hyperplasia, hepatocellular adenoma, and/or hepatocellular carcinoma. A non-limiting set of exemplary glycogen storage diseases may include: GSDI (e.g., GSDIa), GSDIII, GSDIV, GSDVI, and GSDIX.

BRIEF SUMMARY OF THE INVENTION

Aspects of the disclosure relate to oligonucleotides and related methods for treating a glycogen storage disease (e.g., a disease or disorder affecting glycogen breakdown or storage such as GSDIa, GSDIII, GSDIV, GSDVI, or GSDIX) in a subject. In some embodiments, potent RNAi oligonucleotides have been developed for selectively inhibiting GYS2 expression in a subject. In some embodiments, the RNAi oligonucleotides are useful for reducing overall GYS2 activity in hepatocytes, and thereby decreasing or preventing hepatomegaly, liver toxicity (e.g., levels of AST, ALT, and/or ALP), liver fibrosis, fatty acid deposition in the liver, hepatic hyperplasia, hepatocellular adenoma, and/or hepatocellular carcinoma. In some embodiments, key regions of GYS2 mRNA (referred to as hotspots) have been identified herein that are particularly amenable to targeting using such oligonucleotide-based approaches (See, e.g., Example 1).

One aspect of the present disclosure provides oligonucleotides for reducing expression of GYS2. In some embodiments, the oligonucleotides comprise an antisense strand comprising a sequence as set forth in any one of SEQ ID NOs: 193-384, 417-466, 518-568, 575-580, 586-598, or 620-627. In some embodiments, the antisense strand consists of a sequence as set forth in any one of SEQ ID NOs: 193-384, 417-466, 518-568, 575-580, 586-598, or 620-627. In some embodiments, the antisense strand comprises, or consists of, a sequence as set forth in any one of SEQ ID NOs: 417-466, 575-580, 586-598, 620-627. In some embodiments, the oligonucleotides further comprise a sense strand that comprises a sequence as set forth in any one of SEQ ID NOs: 1-192, 385-416, 467-517, 569-574, 581-585, or 612-619. In some embodiments, the sense strand consists of a sequence as set forth in any one of SEQ ID NOs: 1-192, 385-416, 467-517, 569-574, 581-585, or 612-619. In some embodiments, the sense strand comprises, or consists of, a sequence as set forth in any one of SEQ ID NOs: 385-416, 569-574, 581-585, 612-619.

One aspect of the present disclosure provides oligonucleotides for reducing expression of GYS2, in which the oligonucleotides comprise an antisense strand of 15 to 30 nucleotides in length. In some embodiments, the antisense strand has a region of complementarity to a target sequence of GYS2 as set forth in any one of SEQ ID NOs: 599-608. In some embodiments, the region of complementarity is at least 15, at least 16, at least 17, at least 18, at least 19, at least 20, at least 21, or at least 22 contiguous nucleotides in length. In some embodiments, the region of complementarity is fully complementary to the target sequence of GYS2. In some embodiments, the region of complementarity to GYS2 is at least 19 contiguous nucleotides in length.

In some embodiments, the antisense strand is 19 to 27 nucleotides in length. In some embodiments, the antisense strand is 21 to 27 nucleotides in length. In some embodiments, the oligonucleotide further comprises a sense strand of 15 to 40 nucleotides in length, in which the sense strand forms a duplex region with the antisense strand. In some embodiments, the sense strand is 19 to 40 nucleotides in length. In some embodiments, the antisense strand is 27 nucleotides in length and the sense strand is 25 nucleotides in length. In some embodiments, the duplex region is at least 15, at least 16, at least 17, at least 18, at least 19, at least 20, or at least 21 nucleotides in length. In some embodiments, the antisense strand and sense strand form a duplex region of 25 nucleotides in length.

In some embodiments, an oligonucleotide comprises an antisense strand and a sense strand that are each in a range of 21 to 23 nucleotides in length. In some embodiments, an oligonucleotide comprises a duplex structure in a range of 19 to 21 nucleotides in length. In some embodiments, an oligonucleotide comprises a 3'-overhang sequence of one or more nucleotides in length, in which the 3'-overhang sequence is present on the antisense strand, the sense strand, or the antisense strand and sense strand. In some embodiments, an oligonucleotide further comprises a 3'-overhang sequence on the antisense strand of two nucleotides in length. In some embodiments, an oligonucleotide comprises a 3'-overhang sequence of two nucleotides in length, in which the 3'-overhang sequence is present on the antisense strand, and in which the sense strand is 21 nucleotides in length and the antisense strand is 23 nucleotides in length, such that the sense strand and antisense strand form a duplex of 21 nucleotides in length.

In some embodiments, the sense strand comprises a sequence as set forth in any one of SEQ ID NOs: 1-192, 385-416, 467-517, 569-574, 581-585, or 612-619. In some embodiments, the sense strand consists of a sequence as set forth in any one of SEQ ID NOs: 1-192, 385-416, 467-517, 569-574, 581-585, or 612-619. In some embodiments, the antisense strand comprises a sequence as set forth in any one of SEQ ID NOs: 193-384, 417-466, 518-568, 575-580, 586-598, or 620-627. In some embodiments, the antisense strand consists of a sequence as set forth in any one of SEQ ID NOs: 193-384, 417-466, 518-568, 575-580, 586-598, or 620-627.

In some embodiments, the sense strand comprises at its 3'-end a stem-loop set forth as: S1-L-S2, in which S1 is complementary to S2, and in which L forms a loop between S1 and S2 of 3 to 5 nucleotides in length.

Another aspect of the present disclosure provides an oligonucleotide for reducing expression of GYS2, the oligonucleotide comprising an antisense strand and a sense strand, in which the antisense strand is 21 to 27 nucleotides in length and has a region of complementarity to GYS2, in which the sense strand comprises at its 3'-end a stem-loop set forth as: S1-L-S2, in which S1 is complementary to S2, and in which L forms a loop between S1 and S2 of 3 to 5 nucleotides in length, and in which the antisense strand and the sense strand form a duplex structure of at least 19 nucleotides in length but are not covalently linked (see, e.g., FIG. 3). In some embodiments, the region of complementarity is fully complementary to at least 15, at least 16, at least 17, at least 18, at least 19, at least 20, or at least 21 contiguous nucleotides of GYS2 mRNA. In some embodiments, L is a tetraloop. In some embodiments, L is 4 nucleotides in length. In some embodiments, L comprises a sequence set forth as GAAA.

In some embodiments, an oligonucleotide comprises at least one modified nucleotide. In some embodiments, the modified nucleotide comprises a 2'-modification. In some embodiments, the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid. In some embodiments, all of the nucleotides of an oligonucleotide are modified.

In some embodiments, an oligonucleotide comprises at least one modified internucleotide linkage. In some embodiments, the at least one modified internucleotide linkage is a phosphorothioate linkage. In some embodiments, the 4'-carbon of the sugar of the 5'-nucleotide of the antisense strand comprises a phosphate analog. In some embodiments, the phosphate analog is oxymethylphosphonate, vinylphosphonate, or malonylphosphonate.

In some embodiments, at least one nucleotide of an oligonucleotide is conjugated to one or more targeting ligands. In some embodiments, each targeting ligand comprises a carbohydrate, amino sugar, cholesterol, polypeptide, or lipid. In some embodiments, each targeting ligand comprises a N-acetylgalactosamine (GalNAc) moiety. In some embodiments, the GalNac moiety is a monovalent GalNAc moiety, a bivalent GalNAc moiety, a trivalent GalNAc moiety, or a tetravalent GalNAc moiety. In some embodiments, up to 4 nucleotides of L of the stem-loop are each conjugated to a monovalent GalNAc moiety. In some embodiments, the targeting ligand comprises an aptamer.

Another aspect of the present disclosure provides a composition comprising an oligonucleotide of the present disclosure and an excipient. Another aspect of the present disclosure provides a method comprising administering a composition of the present disclosure to a subject. In some embodiments, the method results in a decreased level or prevention of hepatomegaly, liver nodule formation, liver toxicity (e.g., levels of AST, ALT, and/or ALP), liver fibrosis, hepatocellular proliferation, fatty acid deposition in the liver, hepatic hyperplasia, hepatocellular adenoma, and/or hepatocellular carcinoma. Another aspect of the present disclosure provides a method for treating a glycogen storage disease or one or more symptoms of a glycogen storage disease. A non-limiting set of exemplary glycogen storage diseases may include: GSDI (e.g., GSDIa), GSDIII, GSDIV, GSDVI, and GSDIX.

Another aspect of the present disclosure provides an oligonucleotide for reducing expression of GYS2, the oligonucleotide comprising a sense strand of 15 to 40 nucleotides in length and an antisense strand of 15 to 30 nucleotides in length, in which the sense strand forms a duplex region with the antisense strand, in which the sense strand comprises a sequence as set forth in any one of SEQ ID NOs: 1-192, 385-416, 467-517, 569-574, 581-585, or 612-619, and results in a the antisense strand comprises a complementary sequence selected from SEQ ID NOs: 193-384, 417-466, 518-568, 575-580, 586-598, or 620-627.

In some embodiments, the oligonucleotide comprises a pair of sense and antisense strands selected from a row of the table set forth in Table 4.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

DETAILED DESCRIPTION OF THE INVENTION

Figure 1A:
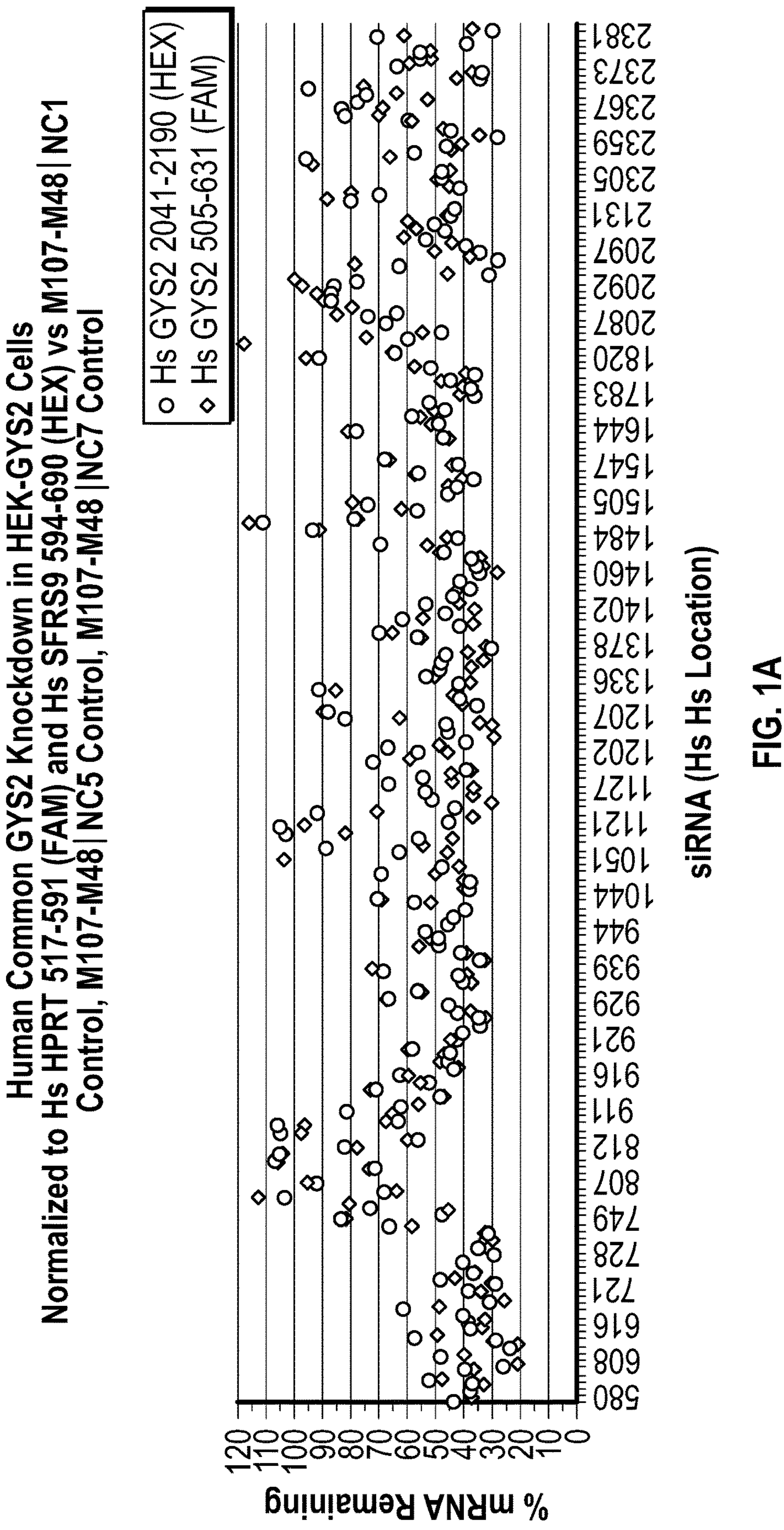
FIGS. 1A and 1B are graphs showing the percentage of GYS2 mRNA remaining after a screen of 264 GYS2 conjugates in HEK-293 cells. The nucleotide position in NM_021957.3 that corresponds to the 3' end of the sense strand of each siRNA is indicated on the x axis.

According to some aspects, the disclosure provides oligonucleotides targeting GYS2 mRNA that are effective for reducing GYS2 expression in cells, particularly liver cells (e.g., hepatocytes) for the treatment of a glycogen storage disease (e.g., GSDIa, GSDIII, GSDIV, GSDVI, and GSDIX) or one or more symptoms of a glycogen storage disease. Accordingly, in related aspects, the disclosure provided methods of treating a glycogen storage disease (e.g., GSDIa, GSDIII, GSDIV, GSDVI, and GSDIX) or one or more symptoms of a glycogen storage disease that involve selectively reducing GYS2 gene expression in liver. In certain embodiments, GYS2 targeting oligonucleotides provided herein are designed for delivery to selected cells of target tissues (e.g., liver hepatocytes) to treat a glycogen storage disease (e.g., GSDIa, GSDIII, GSDIV, GSDVI, and GSDIX) or one or more symptoms of a glycogen storage disease in a subject.

Further aspects of the disclosure, including a description of defined terms, are provided below.

I. Definitions

Administering: As used herein, the terms “administering” or “administration” means to provide a substance (e.g., an oligonucleotide) to a subject in a manner that is pharmacologically useful (e.g., to treat a condition in the subject).

Approximately: As used herein, the term “approximately” or “about,” as applied to one or more values of interest, refers to a value that is similar to a stated reference value. In certain embodiments, the term “approximately” or “about” refers to a range of values that fall within 25%, 20%, 19%, 18%, 17%, 16%, 15%, 14%, 13%, 12%, 11%, 10%, 9% 8% 7%, 6%, 5%, 4%, 3%, 2%, 1%, or less in either direction (greater than or less than) of the stated reference value unless otherwise stated or otherwise evident from the context (except where such number would exceed 100% of a possible value).

Asialoglycoprotein receptor (ASGPR): As used herein, the term “Asialoglycoprotein receptor” or “ASGPR” refers to a bipartite C-type lectin formed by a major 48 kDa (ASGPR-1) and minor 40 kDa subunit (ASGPR-2). ASGPR is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins).

Complementary: As used herein, the term “complementary” refers to a structural relationship between nucleotides (e.g., two nucleotide on opposing nucleic acids or on opposing regions of a single nucleic acid strand) that permits the nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have nucleotide sequences that are complementary to each other so as to form regions of complementarity, as described herein.

Deoxyribonucleotide: As used herein, the term “deoxyribonucleotide” refers to a nucleotide having a hydrogen at the 2' position of its pentose sugar as compared with a ribonucleotide. A modified deoxyribonucleotide is a deoxyribonucleotide having one or more modifications or substitutions of atoms other than at the 2' position, including modifications or substitutions in or of the sugar, phosphate group or base.

Double-stranded oligonucleotide: As used herein, the term “double-stranded oligonucleotide” refers to an oligonucleotide that is substantially in a duplex form. In some embodiments, complementary base-pairing of duplex region (s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from a single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed, e.g., having overhangs at one or both ends. In some embodiments, a double-stranded oligonucleotide comprises antiparallel sequences of nucleotides that are partially complementary, and thus, may have one or more mismatches, which may include internal mismatches or end mismatches.

Duplex: As used herein, the term “duplex,” in reference to nucleic acids (e.g., oligonucleotides), refers to a structure formed through complementary base-pairing of two antiparallel sequences of nucleotides.

Excipient: As used herein, the term “excipient” refers to a non-therapeutic agent that may be included in a composition, for example, to provide or contribute to a desired consistency or stabilizing effect.

Glycogen Storage Disease: As used herein, the term “glycogen storage disease,” “GSD,” or “glycogen storage diseases” refers to metabolic disorders caused by enzyme deficiencies affecting glycogen synthesis, glycogen breakdown, and/or glucose breakdown (glycolysis). Various types of glycogen storage diseases have been characterized, including GSD 0, GSD I (also known as GSD 1 or von Gierke’s disease; e.g., GSDIa), GSD II (also known as Pompe disease or acid maltase deficiency disease), GSD III (also known as GSD 3, Cori’s disease, or Forbes’ disease), GSD IV (GSD 4 or Andersen disease), GSD V (also known as McArdle disease), GSD VI (also known as GSD 6 or Hers’ disease), GSD VII (also known as GSD 7 or Tarui’s disease), GSD VIII, and GSD IX (also known as GSD 9). In some embodiments, individuals having a glycogen storage disease exhibit one or more of a number of symptoms including, but not limited to: hepatomegaly, increased liver toxicity (e.g., higher levels of AST, ALT, and/or ALP), liver fibrosis, fatty acid deposition in the liver, hepatic hyperplasia, hepatocellular adenoma, and/or hepatocellular carcinoma.

GYS2: as used herein, the term "GYS2" or "glycogen synthase 2" refers to the liver glycogen synthase gene. This gene encodes a protein, liver glycogen synthase, that catalyzes a rate-limiting stem in the synthesis of glycogen (i.e., the transfer of a glucose molecule from UDP-glucose to a terminal branch of the glycogen molecule). GYS2 is expressed in liver cells, e.g., hepatocytes. Homologs of GYS2 are conserved across a range of species, including human, mouse, rat, non-human primate species, and others (see, e.g., NCBI HomoloGene: 56580.) In humans, GYS2 encodes multiple transcripts, namely as set forth in GenBank accession numbers NM_021957.3 (SEQ ID NO: 609), XM_006719063.3, and XM_017019245.1, each encoding a different isoform, GenBank accession numbers NP_068776.2, XP_006719126.1 (isoform X1) and XP_016874734.1 (isoform X2), respectively. An example monkey (Rhesus macaque) transcript sequence is set forth in GenBank accession number XM_001098578.2 (SEQ ID NO: 610). An example mouse transcript is set forth in GenBank accession number NM_145572.2 (SEQ ID NO: 611).

Hepatocyte: As used herein, the term "hepatocyte" or "hepatocytes" refers to cells of the parenchymal tissues of the liver. These cells make up approximately 70-85% of the liver's mass and manufacture serum albumin, fibrinogen, and the prothrombin group of clotting factors (except for Factors 3 and 4). Markers for hepatocyte lineage cells may include, but are not limited to: transthyretin (Ttr), glutamine synthetase (Glul), hepatocyte nuclear factor 1a (Hnf1a), and hepatocyte nuclear factor 4a (Hnf4a). Markers for mature hepatocytes may include, but are not limited to: cytochrome P450 (Cyp3al 1), fumarylacetoacetate hydrolase (Fah), glucose 6-phosphate (G6p), albumin (Alb), and OC2-2F8. See, e.g., Huch et al., (2013), Nature, 494(7436): 247-250, the contents of which relating to hepatocyte markers is incorporated herein by reference.

Loop: As used herein, the term "loop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

Modified Internucleotide Linkage: As used herein, the term "modified internucleotide linkage" refers to an internucleotide linkage having one or more chemical modifications compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

Modified Nucleotide: As used herein, the term "modified nucleotide" refers to a nucleotide having one or more chemical modifications compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modifications in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc. In certain embodiments, a modified nucleotide comprises a 2'-O-methyl or a 2'-F substitution at the 2' position of the ribose ring.

Nicked Tetraloop Structure: A "nicked tetraloop structure" is a structure of a RNAi oligonucleotide characterized by the presence of separate sense (passenger) and antisense (guide) strands, in which the sense strand has a region of complementarity to the antisense strand such that the two strands form a duplex, and in which at least one of the strands, generally the sense strand, extends from the duplex in which the extension contains a tetraloop and two self-complementary sequences forming a stem region adjacent to the tetraloop, in which the tetraloop is configured to stabilize the adjacent stem region formed by the self-complementary sequences of the at least one strand.

Oligonucleotide: As used herein, the term "oligonucleotide" refers to a short nucleic acid, e.g., of less than 100 nucleotides in length. An oligonucleotide can comprise ribonucleotides, deoxyribonucleotides, and/or modified nucleotides including, for example, modified ribonucleotides. An oligonucleotide may be single-stranded or double-stranded. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA, or single-stranded siRNA. In some embodiments, a double-stranded oligonucleotide is an RNAi oligonucleotide.

Overhang: As used herein, the term "overhang" refers to terminal non-base-pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a double-stranded oligonucleotide. In certain embodiments, the overhang is a 3' or 5' overhang on the antisense strand or sense strand of a double-stranded oligonucleotide.

Phosphate analog: As used herein, the term "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, for example, International Patent Application PCT/US2017/049909, filed on Sep. 1, 2017, U.S. Provisional Application Nos. 62/383,207, filed on Sep. 2, 2016, and 62/393,401, filed on Sep. 12, 2016, the contents of each of which relating to phosphate analogs are incorporated herein by reference. Other modifications have been developed for the 5' end of oligonucleotides (see, e.g., WO 2011/133871; U.S. Pat. No. 8,927,513; and Prakash et al. (2015), Nucleic Acids Res., 43(6):2993-3011, the contents of each of which relating to phosphate analogs are incorporated herein by reference).

Reduced expression: As used herein, the term "reduced expression" of a gene refers to a decrease in the amount of RNA transcript or protein encoded by the gene and/or a decrease in the amount of activity of the gene in a cell or subject, as compared to an appropriate reference cell or subject. For example, the act of treating a cell with a double-stranded oligonucleotide (e.g., one having an antisense strand that is complementary to GYS2 mRNA sequence) may result in a decrease in the amount of RNA transcript, protein and/or enzymatic activity (e.g., encoded by the GYS2 gene) compared to a cell that is not treated with the double-stranded oligonucleotide. Similarly, "reducing expression" as used herein refers to an act that results in reduced expression of a gene (e.g., GYS2).

Region of Complementarity: As used herein, the term "region of complementarity" refers to a sequence of nucleotides of a nucleic acid (e.g., a double-stranded oligonucleotide) that is sufficiently complementary to an antiparallel sequence of nucleotides (e.g., a target nucleotide sequence within an mRNA) to permit hybridization between the two sequences of nucleotides under appropriate hybridization conditions, e.g., in a phosphate buffer, in a cell, etc. A region of complementarity may be fully complementary to a nucleotide sequence (e.g., a target nucleotide sequence present within an mRNA or portion thereof). For example, a region of complementary that is fully complementary to a nucleotide sequence present in an mRNA has a contiguous sequence of nucleotides that is complementary, without any mismatches or gaps, to a corresponding sequence in the mRNA. Alternatively, a region of complementarity may be partially complementary to a nucleotide sequence (e.g., a nucleotide sequence present in an mRNA or portion thereof). For example, a region of complementary that is partially complementary to a nucleotide sequence present in an mRNA has a contiguous sequence of nucleotides that is complementary to a corresponding sequence in the mRNA but that contains one or more mismatches or gaps (e.g., 1, 2, 3, or more mismatches or gaps) compared with the corresponding sequence in the mRNA, provided that the region of complementarity remains capable of hybridizing with the mRNA under appropriate hybridization conditions.

Ribonucleotide: As used herein, the term "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

RNAi Oligonucleotide: As used herein, the term "RNAi oligonucleotide" refers to either (a) a double stranded oligonucleotide having a sense strand (passenger) and antisense strand (guide), in which the antisense strand or part of the antisense strand is used by the Argonaute 2 (Ago2) endonuclease in the cleavage of a target mRNA or (b) a single stranded oligonucleotide having a single antisense strand, where that antisense strand (or part of that antisense strand) is used by the Ago2 endonuclease in the cleavage of a target mRNA.

Strand: As used herein, the term "strand" refers to a single contiguous sequence of nucleotides linked together through internucleotide linkages (e.g., phosphodiester linkages, phosphorothioate linkages). In some embodiments, a strand has two free ends, e.g., a 5'-end and a 3'-end.

Subject: As used herein, the term "subject" means any mammal, including mice, rabbits, and humans. In one embodiment, the subject is a human or non-human primate. The terms "individual" or "patient" may be used interchangeably with "subject."

Synthetic: As used herein, the term "synthetic" refers to a nucleic acid or other molecule that is artificially synthesized (e.g., using a machine (e.g., a solid state nucleic acid synthesizer)) or that is otherwise not derived from a natural source (e.g., a cell or organism) that normally produces the molecule.

Targeting ligand: As used herein, the term "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

Tetraloop: As used herein, the term "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a melting temperature of at least 50° C., at least 55° C., at least 56° C., at least 58° C., at least 60° C., at least 65° C., or at least 75° C. in 10 mM $NaHPO_4$ to a hairpin comprising a duplex of at least 2 base pairs in length. In some embodiments, a tetraloop may stabilize a base pair in an adjacent stem duplex by stacking interactions. In addition, interactions among the nucleotides in a tetraloop include, but are not limited to: non-Watson-Crick base-pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). In some embodiments, a tetraloop comprises or consists of 3 to 6 nucleotides, and is typically 4 to 5 nucleotides. In certain embodiments, a tetraloop comprises or consists of three, four, five, or six nucleotides, which may or may not be modified (e.g., which may or may not be conjugated to a targeting moiety). In one embodiment, a tetraloop consists of four nucleotides. Any nucleotide may be used in the tetraloop and standard IUPAC-IUB symbols for such nucleotides may be used as described in Cornish-Bowden (1985) Nucl. Acids Res. 13: 3021-3030. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA)), the d(GNRA) family of tetraloops, the d(GNAB) family of tetraloops, the d(CNNG) family of tetraloops, and the d(TNCG) family of tetraloops (e.g., d(TTCG)). See, for example: Nakano et al. Biochemistry, 41 (48), 14281-14292, 2002. SHINJI et al. Nippon Kagakkai Koen Yokoshu VOL. 78th; NO. 2; PAGE. 731 (2000), which are incorporated by reference herein for their relevant disclosures. In some embodiments, the tetraloop is contained within a nicked tetraloop structure.

Treat: As used herein, the term "treat" refers to the act of providing care to a subject in need thereof, e.g., through the administration a therapeutic agent (e.g., an oligonucleotide) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide-Based Inhibitors i. GYS2 Targeting Oligonucleotides

Potent oligonucleotides have been identified herein through examination of the GYS2 mRNA, including mRNAs of different species (human and Rhesus macaque, (see, e.g., Example 1)) and in vitro and in vivo testing. Such oligonucleotides can be used to achieve therapeutic benefit for subjects with a glycogen storage disease (e.g., GSDIa, GSDIII, GSDIV, GSDVI, and GSDIX) or one or more symptoms of a glycogen storage disease by reducing GYS2 activity, and consequently, by decreasing or preventing hepatomegaly, liver toxicity (demonstrated, e.g., levels of AST, ALT, and/or ALP), liver fibrosis, fatty acid deposition in the liver, hepatic hyperplasia, hepatocellular adenoma, and/or hepatocellular carcinoma. For example, potent RNAi oligonucleotides are provided herein that have a sense strand comprising, or consisting of, a sequence as set forth in any one of SEQ ID NOs: 1-192, 385-416, 467-517, 569-574, 581-585, or 612-619, and an antisense strand comprising, or consisting of, a complementary sequence selected from SEQ ID NOs: 193-384, 417-466, 518-568, 575-580, 586-598, or 620-627, as is also arranged the table provided in Table 4 (e.g., a sense strand comprising a sequence as set forth in SEQ ID NO: 1 and an antisense strand comprising a sequence as set forth in SEQ ID NO: 193).

The sequences can be put into multiple different oligonucleotide structures (or formats) as described herein.

In some embodiments, it has been discovered that certain regions of GYS2 mRNA are hotspots for targeting because they are more amenable than other regions to oligonucleotide-based inhibition. In some embodiments, a hotspot region of GYS2 consists of a sequence as forth in any one of SEQ ID NOs: 599-608. These regions of GYS2 mRNA may be targeted using oligonucleotides as discussed herein for purposes of inhibiting GYS2 mRNA expression.

Accordingly, in some embodiments, oligonucleotides provided herein are designed so as to have regions of complementarity to GYS2 mRNA (e.g., within a hotspot of GYS2 mRNA) for purposes of targeting the mRNA in cells and inhibiting its expression. The region of complementarity is generally of a suitable length and base content to enable annealing of the oligonucleotide (or a strand thereof) to GYS2 mRNA for purposes of inhibiting its expression.

In some embodiments, an oligonucleotide disclosed herein comprises a region of complementarity (e.g., on an antisense strand of a double-stranded oligonucleotide) that is at least partially complementary to a sequence as set forth in SEQ ID NOs: 1-192, 385-416, 467-517, 569-574, 581-585, or 612-619, which include sequences mapping to within hotspot regions of GYS2 mRNA. In some embodiments, an oligonucleotide disclosed herein comprises a region of complementarity (e.g., on an antisense strand of a double-stranded oligonucleotide) that is fully complementary to a sequence as set forth in SEQ ID NOs: 1-192, 385-416, 467-517, 569-574, 581-585, or 612-619. In some embodiments, a region of complementarity of an oligonucleotide that is complementary to contiguous nucleotides of a sequence as set forth in SEQ ID NOs: 1-192, 385-416, 467-517, 569-574, 581-585, or 612-619 spans the entire length of an antisense strand. In some embodiments, a region of complementarity of an oligonucleotide that is complementary to contiguous nucleotides of a sequence as set forth in any one of SEQ ID NOs: 1-192, 385-416, 467-517, 569-574, 581-585, or 612-619 spans a portion of the entire length of an antisense strand (e.g., all but two nucleotides at the 3' end of the antisense strand). In some embodiments, an oligonucleotide disclosed herein comprises a region of complementarity (e.g., on an antisense strand of a double-stranded oligonucleotide) that is at least partially (e.g., fully) complementary to a contiguous stretch of nucleotides spanning nucleotides 1-19 of a sequence as set forth in SEQ ID NOs: 1-192, 385-416, 467-517, 569-574, 581-585, or 612-619.

In some embodiments, the region of complementarity is at least 12, at least 13, at least 14, at least 15, at least 16, at least 17, at least 18, at least 19, at least 20, at least 21, at least 22, at least 23, at least 24, or at least 25 nucleotides in length. In some embodiments, an oligonucleotide provided herein has a region of complementarity to GYS2 mRNA that is in the range of 12 to 30 (e.g., 12 to 30, 12 to 22, 15 to 25, 17 to 21, 18 to 27, 19 to 27, or 15 to 30) nucleotides in length. In some embodiments, an oligonucleotide provided herein has a region of complementarity to GYS2 mRNA that is 12, 13, 14, 15, 16, 17, 18, 19, 20, 21, 22, 23, 24, 25, 26, 27, 28, 29, or 30 nucleotides in length.

In some embodiments, a region of complementarity to GYS2 mRNA may have one or more mismatches compared with a corresponding sequence of GYS2 mRNA. A region of complementarity on an oligonucleotide may have up to 1, up to 2, up to 3, up to 4 etc. mismatches provided that it maintains the ability to form complementary base pairs with GYS2 mRNA under appropriate hybridization conditions. Alternatively, a region of complementarity on an oligonucleotide may have no more than 1, no more than 2, no more than 3, or no more than 4 mismatches provided that it maintains the ability to form complementary base pairs with GYS2 mRNA under appropriate hybridization conditions. In some embodiments, if there are more than one mismatches in a region of complementarity, they may be positioned consecutively (e.g., 2, 3, 4, or more in a row), or interspersed throughout the region of complementarity provided that the oligonucleotide maintains the ability to form complementary base pairs with GYS2 mRNA under appropriate hybridization conditions.

Still, in some embodiments, double-stranded oligonucleotides provided herein comprise, or consist of, a sense strand having a sequence as set forth in any one of SEQ ID NOs: 1-192, 385-416, 467-517, 569-574, 581-585, or 612-619 and an antisense strand having a complementary sequence selected from SEQ ID NOs: 193-384, 417-466, 518-568, 575-580, 586-598, or 620-627, as is arranged in the table provided in Table 4 (e.g., a sense strand comprising a sequence as set forth in SEQ ID NO: 1 and an antisense strand comprising a sequence as set forth in SEQ ID NO: 193).

ii. Oligonucleotide Structures

There are a variety of structures of oligonucleotides that are useful for targeting GYS2 mRNA in the methods of the present disclosure, including RNAi, miRNA, etc. Any of the structures described herein or elsewhere may be used as a framework to incorporate or target a sequence described herein (e.g., a hotpot sequence of GYS2 such as those illustrated in SEQ ID NOs: 599-608, or a sense or antisense strand that comprises or consists of a sequence as set forth SEQ ID NOs: 1-192, 385-416, 467-517, 569-574, 581-585, or 612-619 or as set forth SEQ ID NOs: 193-384, 417-466, 518-568, 575-580, 586-598, or 620-627, respectively). Double-stranded oligonucleotides for targeting GYS2 expression (e.g., via the RNAi pathway) generally have a sense strand and an antisense strand that form a duplex with one another. In some embodiments, the sense and antisense strands are not covalently linked. However, in some embodiments, the sense and antisense strands are covalently linked.

In some embodiments, sequences described herein can be incorporated into, or targeted using, oligonucleotides that comprise sense and antisense strands that are both in the range of 17 to 40 nucleotides in length. In some embodiments, oligonucleotides incorporating such sequences are provided that have a tetraloop structure within a 3' extension of their sense strand, and two terminal overhang nucleotides at the 3' end of its antisense strand. In some embodiments, the two terminal overhang nucleotides are GG. Typically, one or both of the two terminal GG nucleotides of the antisense strand is or are not complementary to the target.

In some embodiments, oligonucleotides incorporating such sequences are provided that have sense and antisense strands that are both in the range of 21 to 23 nucleotides in length. In some embodiments, a 3' overhang is provided on the sense, antisense, or both sense and antisense strands that is 1 or 2 nucleotides in length. In some embodiments, an oligonucleotide has a guide strand of 23 nucleotides and a passenger strand of 21 nucleotides, in which the 3'-end of passenger strand and 5'-end of guide strand form a blunt end and where the guide strand has a two nucleotide 3' overhang.

In some embodiments, double-stranded oligonucleotides for reducing GYS2 expression engage RNA interference (RNAi). For example, RNAi oligonucleotides have been developed with each strand having sizes of 19-25 nucleotides with at least one 3' overhang of 1 to 5 nucleotides (see, e.g., U.S. Pat. No. 8,372,968). Longer oligonucleotides have also been developed that are processed by Dicer to generate active RNAi products (see, e.g., U.S. Pat. No. 8,883,996). Further work produced extended double-stranded oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, which are incorporated by reference herein for their disclosure of these oligonucleotides). Such structures may include single-stranded extensions (on one or both sides of the molecule) as well as double-stranded extensions.

In some embodiments, oligonucleotides may be in the range of 21 to 23 nucleotides in length. In some embodiments, oligonucleotides may have an overhang (e.g., of 1, 2, or 3 nucleotides in length) in the 3' end of the sense and/or antisense strands. In some embodiments, oligonucleotides (e.g., siRNAs) may comprise a 21 nucleotide guide strand that is antisense to a target RNA and a complementary passenger strand, in which both strands anneal to form a 19-bp duplex and 2 nucleotide overhangs at either or both 3' ends. See, for example, U.S. Pat. Nos. 9,012,138, 9,012,621, and 9,193,753, the contents of each of which are incorporated herein for their relevant disclosures.

In some embodiments, an oligonucleotide of the invention has a 36 nucleotide sense strand that comprises an region extending beyond the antisense-sense duplex, where the extension region has a stem-tetraloop structure where the stem is a six base pair duplex and where the tetraloop has four nucleotides. In some embodiments, the stem-tetraloop is set forth as: $S_1$-L-$S_2$, in which $S_1$ is complementary to $S_2$ so as to form a duplex, and in which L forms a tetraloop between $S_1$ and $S_2$.

In certain of those embodiments, three or four of the tetraloop nucleotides are each conjugated to a monovalent GalNac ligand.

In some embodiments, an oligonucleotide of the invention comprises a 25 nucleotide sense strand and a 27 nucleotide antisense strand that when acted upon by a dicer enzyme results in an antisense strand that is incorporated into the mature RISC.

Other oligonucleotides designs for use with the compositions and methods disclosed herein include: 16-mer siRNAs (see, e.g., Nucleic Acids in Chemistry and Biology. Blackburn (ed.), Royal Society of Chemistry, 2006), shRNAs (e.g., having 19 bp or shorter stems; see, e.g., Moore et al. Methods Mol. Biol. 2010; 629:141-158), blunt siRNAs (e.g., of 19 bps in length; see: e.g., Kraynack and Baker, RNA Vol. 12, p 163-176 (2006)), asymmetrical siRNAs (aiRNA; see, e.g., Sun et al., Nat. Biotechnol. 26, 1379-1382 (2008)), asymmetric shorter-duplex siRNA (see, e.g., Chang et al., Mol Ther. 2009 April; 17(4): 725-32), fork siRNAs (see, e.g., Hohjoh, FEBS Letters, Vol 557, issues 1-3; January 2004, p 193-198), single-stranded siRNAs (Elsner; Nature Biotechnology 30, 1063 (2012)), dumbbell-shaped circular siRNAs (see, e.g., Abe et al. J Am Chem Soc 129: 15108-15109 (2007)), and small internally segmented interfering RNA (sisiRNA; see, e.g., Bramsen et al., Nucleic Acids Res. 2007 September; 35(17): 5886-5897). Each of the foregoing references is incorporated by reference in its entirety for the related disclosures therein. Further non-limiting examples of an oligonucleotide structures that may be used in some embodiments to reduce or inhibit the expression of GYS2 are microRNA (miRNA), short hairpin RNA (shRNA), and short siRNA (see, e.g., Hamilton et al., Embo J., 2002, 21(17): 4671-4679; see also U.S. Application No. 20090099115).

a. Antisense Strands

In some embodiments, an oligonucleotide disclosed herein for targeting GYS2 comprises an antisense strand comprising or consisting of a sequence as set forth in any one of SEQ ID NOs: 193-384, 417-466, 518-568, 575-580, 586-598, or 620-627. In some embodiments, an oligonucleotide comprises an antisense strand comprising or consisting of at least 12 (e.g., at least 12, at least 13, at least 14, at least 15, at least 16, at least 17, at least 18, at least 19, at least 20, at least 21, at least 22, or at least 23) contiguous nucleotides of a sequence as set forth in any one of SEQ ID NOs: 193-384, 417-466, 518-568, 575-580, 586-598, or 620-627.

In some embodiments, a double-stranded oligonucleotide may have an antisense strand of up to 40 nucleotides in length (e.g., up to 40, up to 35, up to 30, up to 27, up to 25, up to 21, up to 19, up to 17, or up to 12 nucleotides in length). In some embodiments, an oligonucleotide may have an antisense strand of at least 12 nucleotides in length (e.g., at least 12, at least 15, at least 19, at least 21, at least 22, at least 25, at least 27, at least 30, at least 35, or at least 38 nucleotides in length). In some embodiments, an oligonucleotide may have an antisense strand in a range of 12 to 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40, or 32 to 40) nucleotides in length. In some embodiments, an oligonucleotide may have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, an antisense strand of an oligonucleotide may be referred to as a "guide strand." For example, if an antisense strand can engage with RNA-induced silencing complex (RISC) and bind to an Argonaut protein, or engage with or bind to one or more similar factors, and direct silencing of a target gene, it may be referred to as a guide strand. In some embodiments, a sense strand complementary to a guide strand may be referred to as a "passenger strand."

b. Sense Strands

In some embodiments, an oligonucleotide disclosed herein for targeting GYS2 comprises or consists of a sense strand sequence as set forth in in any one of SEQ ID NOs: 1-192, 385-416, 467-517, 569-574, 581-585, or 612-619. In some embodiments, an oligonucleotide has a sense strand that comprises or consists of at least 12 (e.g., at least 13, at least 14, at least 15, at least 16, at least 17, at least 18, at least 19, at least 20, at least 21, at least 22, or at least 23) contiguous nucleotides of a sequence as set forth in in any one of SEQ ID NOs: 1-192, 385-416, 467-517, 569-574, 581-585, or 612-619.

In some embodiments, an oligonucleotide may have a sense strand (or passenger strand) of up to 40 nucleotides in length (e.g., up to 40, up to 36, up to 30, up to 27, up to 25, up to 21, up to 19, up to 17, or up to 12 nucleotides in length). In some embodiments, an oligonucleotide may have a sense strand of at least 12 nucleotides in length (e.g., at least 12, at least 15, at least 19, at least 21, at least 25, at least 27, at least 30, at least 36, or at least 38 nucleotides in length). In some embodiments, an oligonucleotide may have a sense strand in a range of 12 to 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, a sense strand comprises a stem-loop structure at its 3'-end. In some embodiments, a sense strand comprises a stem-loop structure at its 5'-end. In some embodiments, a stem is a duplex of 2, 3, 4, 5, 6, 7, 8, 9, 10, 11, 12, 13, or 14 base pairs in length. In some embodiments, a stem-loop provides the molecule better protection against degradation (e.g., enzymatic degradation) and facilitates targeting characteristics for delivery to a target cell. For example, in some embodiments, a loop provides added nucleotides on which modification can be made without substantially affecting the gene expression inhibition activity of an oligonucleotide. In certain embodiments, an oligonucleotide is provided herein in which the sense strand comprises (e.g., at its 3'-end) a stem-loop set forth as: $S_1$-L-$S_2$, in which $S_1$ is complementary to $S_2$, and in which L forms a loop between $S_1$ and $S_2$ of up to 10 nucleotides in length (e.g., 3, 4, 5, 6, 7, 8, 9, or 10 nucleotides in length).

In some embodiments, a loop (L) of a stem-loop is a tetraloop (e.g., within a nicked tetraloop structure). A tetraloop may contain ribonucleotides, deoxyribonucleotides, modified nucleotides, and combinations thereof. Typically, a tetraloop has 4 to 5 nucleotides.

c. Duplex Length

In some embodiments, a duplex formed between a sense and antisense strand is at least 12 (e.g., at least 15, at least 16, at least 17, at least 18, at least 19, at least 20, or at least 21) nucleotides in length. In some embodiments, a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30, or 21 to 30 nucleotides in length). In some embodiments, a duplex formed between a sense and antisense strand is 12, 13, 14, 15, 16, 17, 18, 19, 20, 21, 22, 23, 24, 25, 26, 27, 28, 29, or 30 nucleotides in length. In some embodiments a duplex formed between a sense and antisense strand does not span the entire length of the sense strand and/or antisense strand. In some embodiments, a duplex between a sense and antisense strand spans the entire length of either the sense or antisense strands. In certain embodiments, a duplex between a sense and antisense strand spans the entire length of both the sense strand and the antisense strand.

d. Oligonucleotide Ends

In some embodiments, an oligonucleotide provided herein comprises sense and antisense strands, such that there is a 3'-overhang on either the sense strand or the antisense strand, or both the sense and antisense strand. In some embodiments, oligonucleotides provided herein have one 5'end that is thermodynamically less stable compared to the other 5' end. In some embodiments, an asymmetric oligonucleotide is provided that includes a blunt end at the 3' end of a sense strand and an overhang at the 3' end of an antisense strand. In some embodiments, a 3' overhang on an antisense strand is 1-8 nucleotides in length (e.g., 1, 2, 3, 4, 5, 6, 7, or 8 nucleotides in length).

Typically, an oligonucleotide for RNAi has a two nucleotide overhang on the 3' end of the antisense (guide) strand. However, other overhangs are possible. In some embodiments, an overhang is a 3' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. However, in some embodiments, the overhang is a 5' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

In some embodiments, one or more (e.g., 2, 3, 4) terminal nucleotides of the 3' end or 5' end of a sense and/or antisense strand are modified. For example, in some embodiments, one or two terminal nucleotides of the 3' end of an antisense strand are modified. In some embodiments, the last nucleotide at the 3' end of an antisense strand is modified, e.g., comprises 2'-modification, e.g., a 2'-O-methoxyethyl. In some embodiments, the last one or two terminal nucleotides at the 3' end of an antisense strand are complementary to the target. In some embodiments, the last one or two nucleotides at the 3' end of the antisense strand are not complementary to the target. In some embodiments, the 5' end and/or the 3' end of a sense or antisense strand has an inverted cap nucleotide.

e. Mismatches

In some embodiments, there is one or more (e.g., 1, 2, 3, or 4) mismatches between a sense and antisense strand. If there is more than one mismatch between a sense and antisense strand, they may be positioned consecutively (e.g., 2, 3 or more in a row), or interspersed throughout the region of complementarity. In some embodiments, the 3'-terminus of the sense strand contains one or more mismatches. In one embodiment, two mismatches are incorporated at the 3' terminus of the sense strand. In some embodiments, base mismatches or destabilization of segments at the 3'-end of the sense strand of the oligonucleotide improved the potency of synthetic duplexes in RNAi, possibly through facilitating processing by Dicer.

iii. Single-Stranded Oligonucleotides

In some embodiments, an oligonucleotide for reducing GYS2 expression as described herein is single-stranded. Such structures may include, but are not limited to single-stranded RNAi oligonucleotides. Recent efforts have demonstrated the activity of single-stranded RNAi oligonucleotides (see, e.g., Matsui et al. (May 2016), Molecular Therapy, Vol. 24(5), 946-955). However, in some embodiments, oligonucleotides provided herein are antisense oligonucleotides (ASOs). An antisense oligonucleotide is a single-stranded oligonucleotide that has a nucleobase sequence which, when written in the 5' to 3' direction, comprises the reverse complement of a targeted segment of a particular nucleic acid and is suitably modified (e.g., as a gapmer) so as to induce RNaseH mediated cleavage of its target RNA in cells or (e.g., as a mixmer) so as to inhibit translation of the target mRNA in cells. Antisense oligonucleotides for use in the instant disclosure may be modified in any suitable manner known in the art including, for example, as shown in U.S. Pat. No. 9,567,587, which is incorporated by reference herein for its disclosure regarding modification of antisense oligonucleotides (including, e.g., length, sugar moieties of the nucleobase (pyrimidine, purine), and alterations of the heterocyclic portion of the nucleobase). Further, antisense molecules have been used for decades to reduce expression of specific target genes (see, e.g., Bennett et al.; Pharmacology of Antisense Drugs, Annual Review of Pharmacology and Toxicology, Vol. 57: 81-105).

iv. Oligonucleotide Modifications

Oligonucleotides may be modified in various ways to improve or control specificity, stability, delivery, bioavailability, resistance from nuclease degradation, immunogenicity, base-paring properties, RNA distribution and cellular uptake and other features relevant to therapeutic or research use. See, e.g., Bramsen et al., Nucleic Acids Res., 2009, 37, 2867-2881; Bramsen and Kjems (Frontiers in Genetics, 3 (2012): 1-22). Accordingly, in some embodiments, oligonucleotides of the present disclosure may include one or more suitable modifications. In some embodiments, a modified nucleotide has a modification in its base (or nucleobase), the sugar (e.g., ribose, deoxyribose), or the phosphate group.

The number of modifications on an oligonucleotide and the positions of those nucleotide modifications may influence the properties of an oligonucleotide. For example, oligonucleotides may be delivered in vivo by conjugating them to or encompassing them in a lipid nanoparticle (LNP) or similar carrier. However, when an oligonucleotide is not protected by an LNP or similar carrier (e.g., "naked delivery"), it may be advantageous for at least some of the its nucleotides to be modified. Accordingly, in certain embodiments of any of the oligonucleotides provided herein, all or substantially all of the nucleotides of an oligonucleotide are modified. In certain embodiments, more than half of the nucleotides are modified. In certain embodiments, less than half of the nucleotides are modified. Typically, with naked delivery, every nucleotide is modified at the 2'-position of the sugar group of that nucleotide. These modifications may be reversible or irreversible. Typically, the 2'-position modification is 2'-fluoro, 2'-O-methyl, etc. In some embodiments, an oligonucleotide as disclosed herein has a number and type of modified nucleotides sufficient to cause the desired characteristic (e.g., protection from enzymatic degradation, capacity to target a desired cell after in vivo administration, and/or thermodynamic stability).

a. Sugar Modifications

In some embodiments, a modified sugar (also referred to herein as a sugar analog) includes a modified deoxyribose or ribose moiety, e.g., in which one or more modifications occur at the 2', 3', 4', and/or 5' carbon position of the sugar. In some embodiments, a modified sugar may also include non-natural alternative carbon structures such as those present in locked nucleic acids ("LNA") (see, e.g., Koshkin et al. (1998), Tetrahedron 54, 3607-3630), unlocked nucleic acids ("UNA") (see, e.g., Snead et al. (2013), Molecular Therapy—Nucleic Acids, 2, e103), and bridged nucleic acids ("BNA") (see, e.g., Imanishi and Obika (2002), The Royal Society of Chemistry, Chem. Commun., 1653-1659). Koshkin et al., Snead et al., and Imanishi and Obika are incorporated by reference herein for their disclosures relating to sugar modifications.

In some embodiments, a nucleotide modification in a sugar comprises a 2'-modification. In certain embodiments, the 2'-modification may be 2'-aminoethyl, 2'-fluoro, 2'-O-methyl, 2'-O-methoxyethyl, or 2'-deoxy-2'-fluoro-β-d-arabinonucleic acid. Typically, the modification is 2'-fluoro, 2'-O-methyl, or 2'-O-methoxyethyl. However, a large variety of 2' position modifications that have been developed for use in oligonucleotides can be employed in oligonucleotides disclosed herein. See, e.g., Bramsen et al., Nucleic Acids Res., 2009, 37, 2867-2881. In some embodiments, a modification in a sugar comprises a modification of the sugar ring, which may comprise modification of one or more carbons of the sugar ring. For example, a modification of a sugar of a nucleotide may comprise a linkage between the 2'-carbon and a 1'-carbon or 4'-carbon of the sugar. For example, the linkage may comprise an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the terminal 3'-end group (e.g., a 3'-hydroxyl) is a phosphate group or other group, which can be used, for example, to attach linkers, adapters or labels or for the direct ligation of an oligonucleotide to another nucleic acid.

b. 5' Terminal Phosphates

5'-terminal phosphate groups of oligonucleotides may or in some circumstances enhance the interaction with Argonaut 2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation. In some embodiments, a phosphate analog may be oxymethylphosphonate, vinylphosphonate, or malonylphosphonate. In certain embodiments, the 5' end of an oligonucleotide strand is attached to a chemical moiety that mimics the electrostatic and steric properties of a natural 5'-phosphate group ("phosphate mimic") (see, e.g., Prakash et al. (2015), Nucleic Acids Res., Nucleic Acids Res. 2015 Mar. 31; 43(6): 2993-3011, the contents of which relating to phosphate analogs are incorporated herein by reference). Many phosphate mimics have been developed that can be attached to the 5' end (see, e.g., U.S. Pat. No. 8,927,513, the contents of which relating to phosphate analogs are incorporated herein by reference). Other modifications have been developed for the 5' end of oligonucleotides (see, e.g., WO 2011/133871, the contents of which relating to phosphate analogs are incorporated herein by reference). In certain embodiments, a hydroxyl group is attached to the 5' end of the oligonucleotide.

In some embodiments, an oligonucleotide has a phosphate analog at a 4'-carbon position of the sugar (referred to as a "4'-phosphate analog"). See, for example, International Patent Application PCT/US2017/049909, filed on Sep. 1, 2017, U.S. Provisional Application Nos. 62/383,207, entitled 4'-Phosphate Analogs and Oligonucleotides Comprising the Same, filed on Sep. 2, 2016, and 62/393,401, filed on Sep. 12, 2016, entitled 4'-Phosphate Analogs and Oligonucleotides Comprising the Same, the contents of each of which relating to phosphate analogs are incorporated herein by reference. In some embodiments, an oligonucleotide provided herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the aminomethyl group is bound to the 4'-carbon of the sugar moiety or analog thereof. In certain embodiments, a 4'-phosphate analog is an oxymethylphosphonate. In some embodiments, an oxymethylphosphonate is represented by the formula $—O—CH_2—PO(OH)_2$ or $—O—CH_2—PO(OR)_2$, in which R is independently selected from H, $CH_3$, an alkyl group, $CH_2CH_2CN$, $CH_2OCOC(CH_3)_3$, $CH_2OCH_2CH_2Si(CH_3)_3$, or a protecting group. In certain embodiments, the alkyl group is $CH_2CH_3$. More typically, R is independently selected from H, $CH_3$, or $CH_2CH_3$.

c. Modified Internucleoside Linkages

In some embodiments, the oligonucleotide may comprise a modified internucleoside linkage. In some embodiments, phosphate modifications or substitutions may result in an oligonucleotide that comprises at least one (e.g., at least 1, at least 2, at least 3, at least 4, or at least 5) modified internucleotide linkage. In some embodiments, any one of the oligonucleotides disclosed herein comprises 1 to 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9, or 10 modified internucleotide linkages.

A modified internucleotide linkage may be a phosphorodithioate linkage, a phosphorothioate linkage, a phosphotriester linkage, a thionoalkylphosphonate linkage, a thionoalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

d. Base Modifications

In some embodiments, oligonucleotides provided herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain a nitrogen atom. See e.g., U.S. Published Patent Application No. 20080274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution that, when present in a duplex, can be positioned opposite more than one type of base without substantially altering the structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower $T_m$ than a duplex formed with the complementary nucleic acid. However, in some embodiments, compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43. Each of the foregoing is incorporated by reference herein for their disclosures relating to base modifications).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See U.S. Published Application No. 2011/0294869 originally assigned to Traversa Therapeutics, Inc. ("Traversa"), PCT Publication No. WO 2015/188197 to Solstice Biologics, Ltd. ("Solstice"), Meade et al., *Nature Biotechnology,* 2014, 32:1256-1263 ("Meade"), PCT Publication No. WO 2014/088920 to Merck Sharp & Dohme Corp, each of which are incorporated by reference for their disclosures of such modifications. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (Dellinger et al. *J. Am. Chem. Soc.* 2003, 125:940-950).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed and the result is a cleaved oligonucleotide. Using reversible, glutathione sensitive moieties, it is possible to introduce sterically larger chemical groups into the oligonucleotide of interest as compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity, and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of a sugar, particularly when the modified nucleotide is the 3'-terminal nucleotide of the oligonucleotide. In some embodiments, the glutathione-sensitive moiety comprises a sulfonyl group. See, e.g., International Patent Application PCT/US2017/048239, which published on Mar. 1, 2018 as International Patent Publication WO2018/039364, entitled Compositions Comprising Reversibly Modified Oligonucleotides and Uses Thereof, which was filed on Aug. 23, 2016, the contents of which are incorporated by reference herein for its relevant disclosures.

v. Targeting Ligands

In some embodiments, it may be desirable to target the oligonucleotides of the disclosure to one or more cells or one or more organs. Such a strategy may help to avoid undesirable effects in other organs, or may avoid undue loss of the oligonucleotide to cells, tissue or organs that would not benefit for the oligonucleotide. Accordingly, in some embodiments, oligonucleotides disclosed herein may be modified to facilitate targeting of a particular tissue, cell or organ, e.g., to facilitate delivery of the oligonucleotide to the liver. In certain embodiments, oligonucleotides disclosed herein may be modified to facilitate delivery of the oligonucleotide to the hepatocytes of the liver. In some embodiments, an oligonucleotide comprises a nucleotide that is conjugated to one or more targeting ligands.

A targeting ligand may comprise a carbohydrate, amino sugar, cholesterol, peptide, polypeptide, protein or part of a protein (e.g., an antibody or antibody fragment) or lipid. In some embodiments, a targeting ligand is an aptamer. For example, a targeting ligand may be an RGD peptide that is used to target tumor vasculature or glioma cells, CREKA peptide to target tumor vasculature or stoma, transferrin, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5, or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3, or 4 nucleotides of the loop of the stem may be individually conjugated to a targeting ligand, as described, for example, in International Patent Application Publication WO 2016/100401, which was published on Jun. 23, 2016, the relevant contents of which are incorporated herein by reference.

In some embodiments, it is desirable to target an oligonucleotide that reduces the expression of GYS2 to the hepatocytes of the liver of a subject. Any suitable hepatocyte targeting moiety may be used for this purpose.

GalNAc is a high affinity ligand for asialoglycoprotein receptor (ASGPR), which is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins). Conjugation (either indirect or direct) of GalNAc moieties to oligonucleotides of the instant disclosure may be used to target these oligonucleotides to the ASGPR expressed on these hepatocyte cells.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3, or 4 monovalent GalNAc moieties, and is typically conjugated to 3 or 4 monovalent GalNAc moieties). In some embodiments, an oligonucleotide of the instant disclosure is conjugated to one or more bivalent GalNAc, trivalent GalNAc, or tetravalent GalNAc moieties.

In some embodiments, 1 or more (e.g., 1, 2, 3, 4, 5, or 6) nucleotides of an oligonucleotide are each conjugated to a GalNAc moiety. In some embodiments, 2 to 4 nucleotides of the loop (L) of the stem-loop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. For example, an oligonucleotide may comprise a stem-loop at either the 5' or 3' end of the sense strand and 1, 2, 3, or 4 nucleotides of the loop of the stem may be individually conjugated to a GalNAc moiety. In some embodiments, GalNAc moieties are conjugated to a nucleotide of the sense strand. For example, four GalNAc moieties can be conjugated to nucleotides in the tetraloop of the sense strand, where each GalNAc moiety is conjugated to one nucleotide.

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in International Patent Application Publication Number WO2016100401 A1, which published on Jun. 23, 2016, and the contents of which relating to such linkers are incorporated herein by reference. In some embodiments, the linker is a labile linker. However, in other embodiments, the linker is fairly stable. In some embodiments, a duplex extension (up to 3, 4, 5, or 6 base pairs in length) is provided between a targeting ligand (e.g., a GalNAc moiety) and a double-stranded oligonucleotide.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., single-stranded or double-stranded oligonucleotides) to reduce the expression of GYS2. Such compositions can be suitably formulated such that when administered to a subject, either into the immediate environment of a target cell or systemically, a sufficient portion of the oligonucleotides enter the cell to reduce GYS2 expression. Any of a variety of suitable oligonucleotide formulations can be used to deliver oligonucleotides for the reduction of GYS2 as disclosed herein. In some embodiments, an oligonucleotide is formulated in buffer solutions such as phosphate-buffered saline solutions, liposomes, micellar structures, and capsids. In some embodiments, naked oligonucleotides or conjugates thereof are formulated in water or in an aqueous solution (e.g., water with pH adjustments). In some embodiments, naked oligonucleotides or conjugates thereof are formulated in basic buffered aqueous solutions (e.g., PBS)

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine) can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere, or a nanoparticle, or may be otherwise formulated for administration to the cells, tissues, organs, or body of a subject in need thereof (see, e.g., Remington: The Science and Practice of Pharmacy, 22nd edition, Pharmaceutical Press, 2013).

In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Typically. the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. For intravenous or subcutaneous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. In many cases, it will be preferable to include isotonic agents, for example, sugars, polyalcohols such as mannitol, sorbitol, and sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.10% of the therapeutic agent (e.g., an oligonucleotide for reducing GYS2 expression) or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though a number of embodiments are directed to liver-targeted delivery of any of the oligonucleotides disclosed herein, targeting of other tissues is also contemplated.

IV. Methods of Use i. Reducing GYS2 Expression in Cells

In some embodiments, methods are provided for delivering to a cell an effective amount any one of oligonucleotides disclosed herein for purposes of reducing expression of GYS2 in the cell. Methods provided herein are useful in any appropriate cell type. In some embodiments, a cell is any cell that expresses GYS2 (e.g., liver cells such as hepatocytes or adipose cells). In some embodiments, the cell is a primary cell that has been obtained from a subject and that may have undergone a limited number of a passages, such that the cell substantially maintains its natural phenotypic properties. In some embodiments, a cell to which the oligonucleotide is delivered is ex vivo or in vitro (i.e., can be delivered to a cell in culture or to an organism in which the cell resides). In specific embodiments, methods are provided for delivering to a cell an effective amount any one of the oligonucleotides disclosed herein for purposes of reducing expression of GYS2 solely or primarily in hepatocytes.

In some embodiments, oligonucleotides disclosed herein can be introduced using appropriate nucleic acid delivery methods including injection of a solution containing the oligonucleotides, bombardment by particles covered by the oligonucleotides, exposing the cell or organism to a solution containing the oligonucleotides, or electroporation of cell membranes in the presence of the oligonucleotides. Other appropriate methods for delivering oligonucleotides to cells may be used, such as lipid-mediated carrier transport, chemical-mediated transport, and cationic liposome transfection such as calcium phosphate, and others.

The consequences of inhibition can be confirmed by an appropriate assay to evaluate one or more properties of a cell or subject, or by biochemical techniques that evaluate molecules indicative of GYS2 expression (e.g., RNA, protein). In some embodiments, the extent to which an oligonucleotide provided herein reduces levels of expression of GYS2 is evaluated by comparing expression levels (e.g., mRNA or protein levels of GYS2 to an appropriate control (e.g., a level of GYS2 expression in a cell or population of cells to which an oligonucleotide has not been delivered or to which a negative control has been delivered). In some embodiments, an appropriate control level of GYS2 expression may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide as described herein results in a reduction in the level of GYS2 expression in a cell. In some embodiments, the reduction in levels of GYS2 expression may be a reduction to 1% or lower, 5% or lower, 10% or lower, 15% or lower, 20% or lower, 25% or lower, 30% or lower, 35% or lower, 40% or lower, 45% or lower, 50% or lower, 55% or lower, 60% or lower, 70% or lower, 80% or lower, or 90% or lower compared with an appropriate control level of GYS2. The appropriate control level may be a level of GYS2 expression in a cell or population of cells that has not been contacted with an oligonucleotide as described herein. In some embodiments, the effect of delivery of an oligonucleotide to a cell according to a method disclosed herein is assessed after a finite period of time. For example, levels of GYS2 may be analyzed in a cell at least 8 hours, 12 hours, 18 hours, 24 hours; or at least one, two, three, four, five, six, seven, or fourteen days after introduction of the oligonucleotide into the cell.

In some embodiments, an oligonucleotide is delivered in the form of a transgene that is engineered to express in a cell the oligonucleotides (e.g., its sense and antisense strands). In some embodiments, an oligonucleotide is delivered using a transgene that is engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Treatment Methods

Aspects of the disclosure relate to methods for reducing GYS2 expression for the treatment of a glycogen storage disease in a subject. In some embodiments, the methods may comprise administering to a subject in need thereof an effective amount of any one of the oligonucleotides disclosed herein. Such treatments could be used, for example, to decrease or prevent hepatomegaly, liver toxicity (e.g., lower or decrease levels of AST, ALT, and/or ALP), liver fibrosis, fatty acid deposition in the liver, hepatic hyperplasia, hepatocellular adenoma, and/or hepatocellular carcinoma. Such treatments could also be used, for example, to treat or prevent one or more symptoms associated with a glycogen storage disease selected from the list consisting of: GSDIa, GSDIII, GSDIV, GSDVI, and GSDIX, or to treat or prevent one or more symptoms of such a glycogen storage disease. The present disclosure provides for both prophylactic and therapeutic methods of treating a subject at risk of (or susceptible to) a glycogen storage disease (e.g., GSDIa, GSDIII, GSDIV, GSDVI, and GSDIX) and/or symptoms or conditions associated with a glycogen storage disease (e.g., GSDIa, GSDIII, GSDIV, GSDVI, and GSDIX).

In certain aspects, the disclosure provides a method for preventing in a subject, a disease, disorder, symptom, or condition as described herein by administering to the subject a therapeutic agent (e.g., an oligonucleotide or vector or transgene encoding same). In some embodiments, the subject to be treated is a subject who will benefit therapeutically from a reduction in the amount of GYS2 protein, e.g., in the liver.

Methods described herein typically involve administering to a subject an effective amount of an oligonucleotide, that is, an amount capable of producing a desirable therapeutic result. A therapeutically acceptable amount may be an amount that is capable of treating a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions disclosed herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intramuscular injection), topically (e.g., epicutaneous, inhalational, via eye drops, or through a mucous membrane), or by direct injection into a target organ (e.g., the liver of a subject). Typically, oligonucleotides disclosed herein are administered intravenously or subcutaneously.

In some embodiments, oligonucleotides are administered at a dose in a range of 0.1 mg/kg to 25 mg/kg (e.g., 1 mg/kg to 5 mg/kg). In some embodiments, oligonucleotides are administered at a dose in a range of 0.1 mg/kg to 5 mg/kg or in a range of 0.5 mg/kg to 5 mg/kg.

As a non-limiting set of examples, the oligonucleotides of the instant disclosure would typically be administered once per year, twice per year, quarterly (once every three months), bi-monthly (once every two months), monthly, or weekly.

In some embodiments, the subject to be treated is a human (e.g., a human patient) or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

EXAMPLES

Example 1: Development of GYS2 Oligonucleotide Inhibitors Using Human and Mouse Cell-Based Assays Human and mouse-based assays were used to develop candidate oligonucleotides for inhibition of GYS2 expression. First, a computer-based algorithm was used to generate candidate oligonucleotide sequences (25-27-mer) for GYS2 inhibition. Cell-based assays and PCR assays were then employed for evaluation of candidate oligonucleotides for their ability to reduce GYS2 expression.

The computer-based algorithm provided oligonucleotides that were complementary to the human GYS2 mRNA (SEQ ID NO: 609, Table 1), of which certain sequences were also complementary to the Rhesus macaque GYS2 mRNA (SEQ ID NO: 610, Table 1).

TABLE 1

Sequences of human and Rhesus macaque GYS2 mRNA

| Species | GenBank RefSeq # | SEQ ID NO. |
|---|---|---|
| Human | NM_021957.3 | 609 |
| Rhesus macaque | XM_001098578.2 | 610 |

Figure 1B:
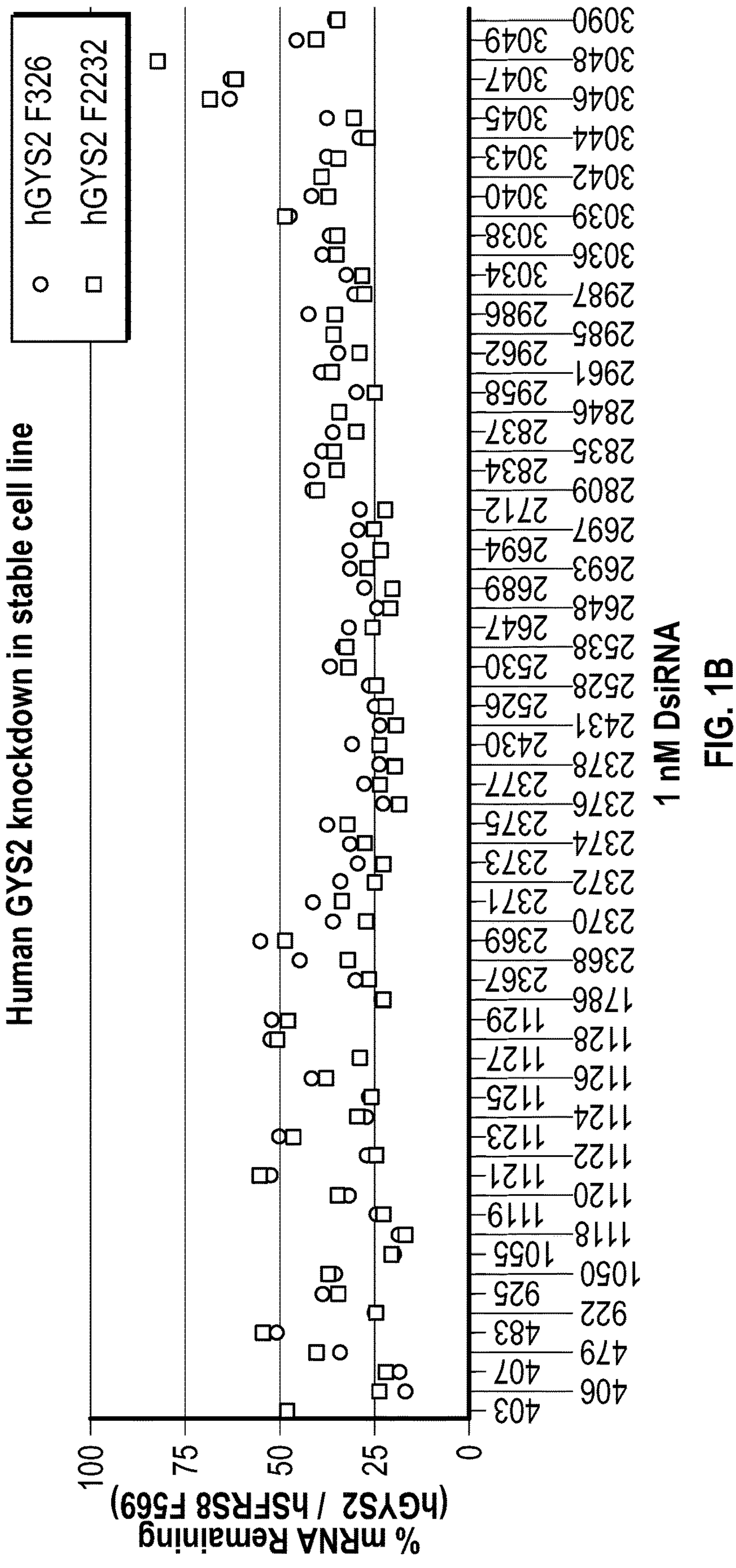

Of the oligonucleotides that the algorithm provided, 264 oligonucleotides were selected as candidates for experimental evaluation in a HEK-293 cell-based assay. In this assay, HEK-293 human embryonic kidney cells stably expressing GYS2 (referred to as HEK-GYS2 cells) were transfected with the oligonucleotides. Cells were maintained for a period of time following transfection and then levels of remaining GYS2 mRNA were interrogated using TAQMAN®-based qPCR assays. Two qPCR assays, a 3' assay and a 5' assay, were used to determine mRNA levels as measured by HEX and FAM probes, respectively. The results of the HEK-293 cell-based assay with the 264 oligonucleotides are shown in FIGS. 1A and 1B. The percent mRNA remaining is shown for each of the 3' assay (circle shapes) and the 5' assay (diamond shapes). Oligonucleotides with the lowest percentage of mRNA remaining compared to negative controls were considered hits. Oligonucleotides with low complementarity to the human genome were used as negative controls.

Based on the activity and locations of these oligonucleotides, hotspots on the human GYS2 mRNA were defined. A hotspot was identified as a stretch on the human GYS2 mRNA sequence associated with at least two oligonucleotides resulting in mRNA levels that were less than or equal to 35% in either assay compared with controls. Accordingly, the following hotspots within the human GYS2 mRNA sequence were identified: 579-618, 691-738, 1089-1125, 1175-1211, 1431-1486, 2341-2383, 2497-2543, 2660-2698, 2808-2851, and 3014-3050.

The sequences of the hotspots are outlined in Table 2.

TABLE 2

Sequences of Hotspots

| Hotspot Position In Human GYS2 mRNA | Sequence | SEQ ID NO. |
|---|---|---|
| 579-618 | GATAGAAGGAAGTCCTTATGTGGTACTTTTTGACATAGGC | 599 |
| 691-738 | GACCGAGAAGCCAATGATATGCTGATATTTGGATCTTTAACTGCCTGG | 600 |
| 1089-1125 | TCCAAACGGCTTGAATGTTAAGAAATTTTCAGCAGTG | 601 |
| 1175-1211 | TTGTTCGAGGTCATTTCTATGGICATCTCGACTTTGA | 602 |
| 1431-1486 | TGCACATTCTGTGAAGGAAAAGTTTGGAAAAAAACTCTATGATGCATTATTAAGAG | 603 |
| 2341-2383 | AAGCTGCATGGTGAATATAAGAACTGAATTCTACATGTGCTGC | 604 |
| 2497-2543 | GTGGAAGAAATTGAGTGAATGACAATTTTGTAATTTAGGATAAGATC | 605 |
| 2660-2698 | TTTCTCTTACTCTGTTTATTTTTAAATGATCATCATAAT | 606 |
| 2808-2851 | TAGCTAGGTTTTTACTGATTATTTTCATTTTTCACATGCATCAG | 607 |
| 3014-3050 | TCTTACTGTAACATTTTTCTATTGTTTAAATAGAAAG | 608 |

Dose Response Analysis

Of the 264 oligonucleotides evaluated in the initial HEK-293 cell-based assay, 71 particularly active oligonucleotides were selected as hits based on their ability to knock down GYS2 levels and were subjected to a secondary screen.

Figure 2A:
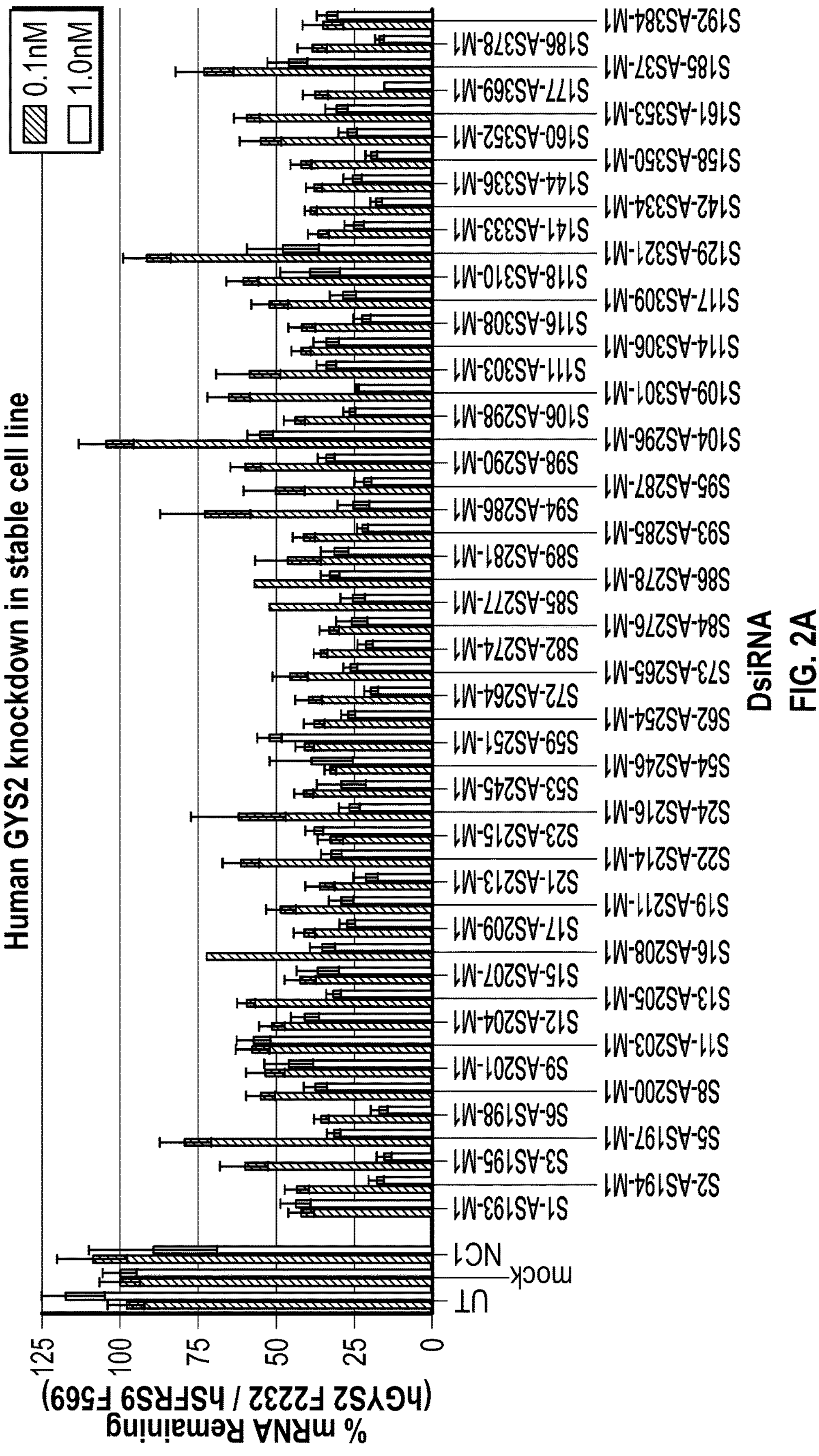
FIGS. 2A and 2B is a set of graphs showing the percentage of mRNA remaining after GYS2 oligonucleotide screening of 71 GYS2 oligonucleotides at two or three different concentrations (0.1 nM and 1.0 nM or 0.03 nM, 0.1 nM, and 1.0 nM) in HEK-293 cells.
Figure 2B:
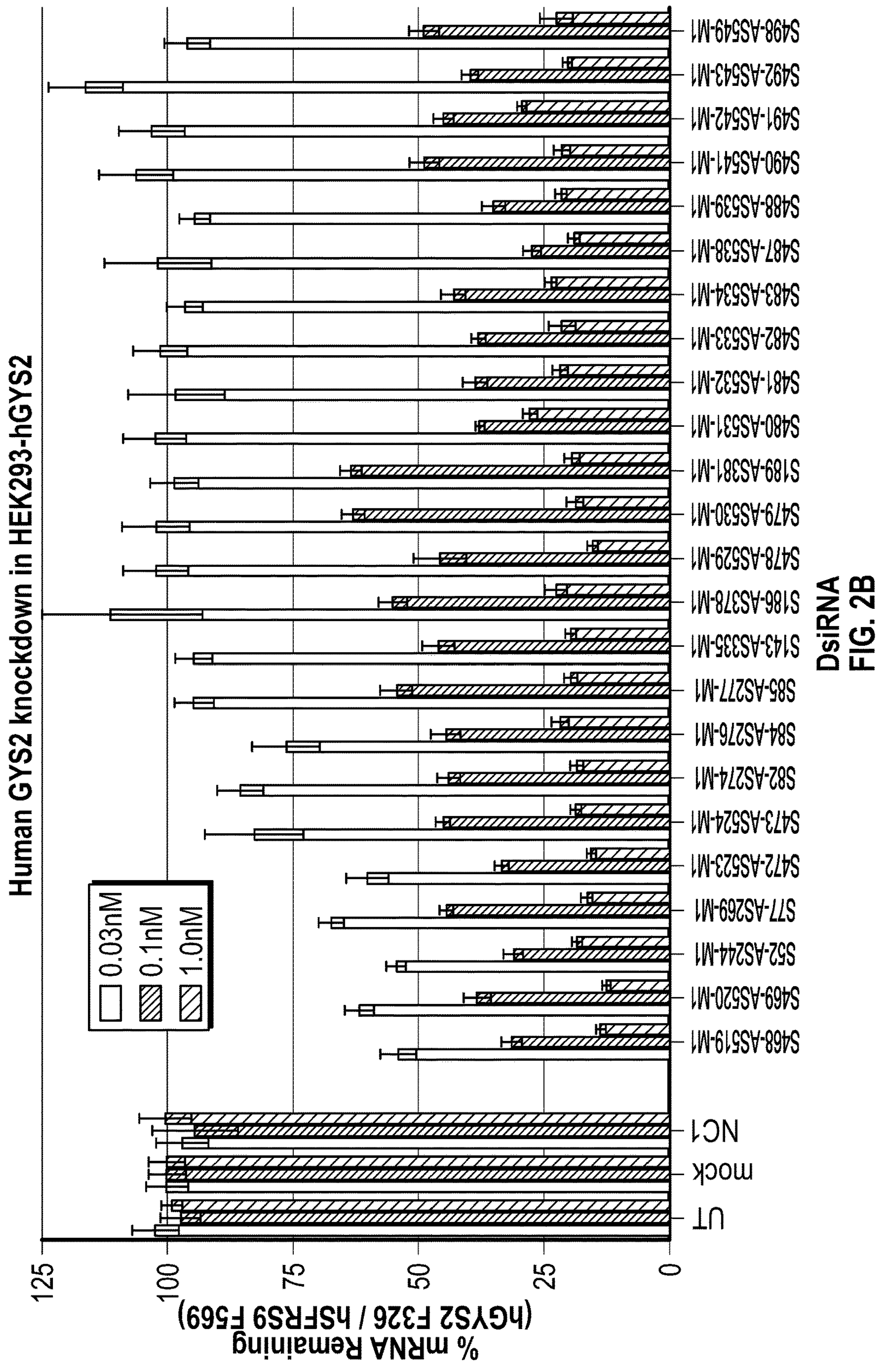

In this secondary screen, the candidate oligonucleotides were tested using the same assay as in the primary screen, but at two or three different concentrations (1 nM, 0.1 nM and 0.03 nM) (FIGS. 2A and 2B). The target mRNA levels were generally normalized based on splicing factor, arginine/serine-rich 9 (SFRS9), a housekeeping gene that provides a stable expression reference across samples, to generate the percent mRNA shown in FIGS. 2A and 2B. The tested oligonucleotides in each of FIGS. 2A and 2B are shown compared to negative control sequences (NC1) and mock transfection. All 71 oligonucleotides had the same modification pattern, designated M1, which contains a combination of ribonucleotides, deoxyribonucleotides and 2'-O-methyl modified nucleotides. The sequences of the 71 oligonucleotides tested are provided in Table 3.

TABLE 3

| Candidate oligonucleotide Sequences for HEK-293 Cell-Based Assay | | | |
|---|---|---|---|
| Hs | Rm | Sense SEQ ID NO. | Corresponding Antisense SEQ ID NO. |
| X | X | 1-3, 5, 6, 8, 9, 11-13, 15-17, 19, 21-24, 52-54, 59, 62, 72, 73, 77, 82, 84-86, 89, 93-95, 98, 104, 106, 109, 111, 114, 116-118, 129, 141-144, 158, 160, 161, 177, 185, 186, 189, 192, 468, 469, 472, 473, 478-480, 482, 483, 487, 488, 490-492, 498 | 193-195, 197, 198, 200, 201, 203-205, 207-209, 211, 213-216, 244-246, 251, 254, 264, 265, 269, 274, 276-278, 281, 285-287, 290, 296, 298, 301, 303, 306, 308-310, 321, 333-336, 350, 352, 353, 369, 377, 378, 381, 384, 519, 520, 523, 524, 529-531, 533, 534, 538, 539, 541-543, 549 |

Hs: human and Rm: Rhesus macaque; the sense and antisense SEQ ID NO. columns provide the sense strand and respective antisense strand, in relative order, that are hybridized to make each oligonucleotide. For example, sense strand of SEQ ID NO: 1 hybridizes with antisense strand of SEQ ID NO: 193.

Figure 3:
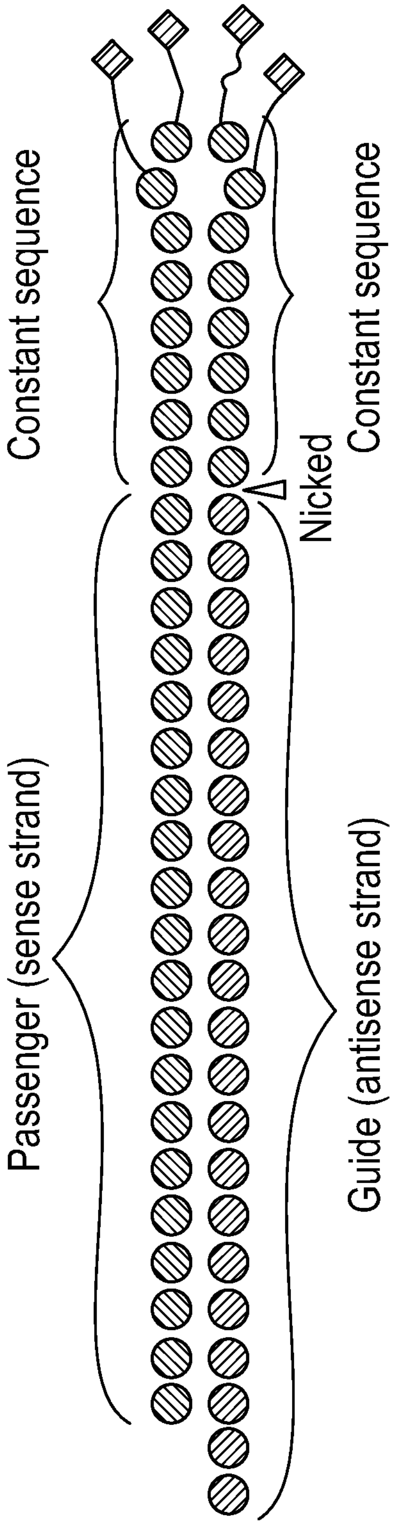
FIG. 3 is a schematic showing a non-limiting example of a double-stranded oligonucleotide with a nicked tetraloop structure that has been conjugated to four GalNAc moieties (diamond shapes).

At this stage, 36 of the most potent sequences from the testing were selected for further analysis. The selected sequences were converted to nicked tetraloop structure formats (a 36-mer passenger strand with a 22-mer guide strand). See FIG. 3 for a generic tetraloop structure. These oligonucleotides were then tested as before, evaluating each oligonucleotide at three concentrations for its ability to reduce GYS2 mRNA expression in HepG2 cells.

Figure 4:
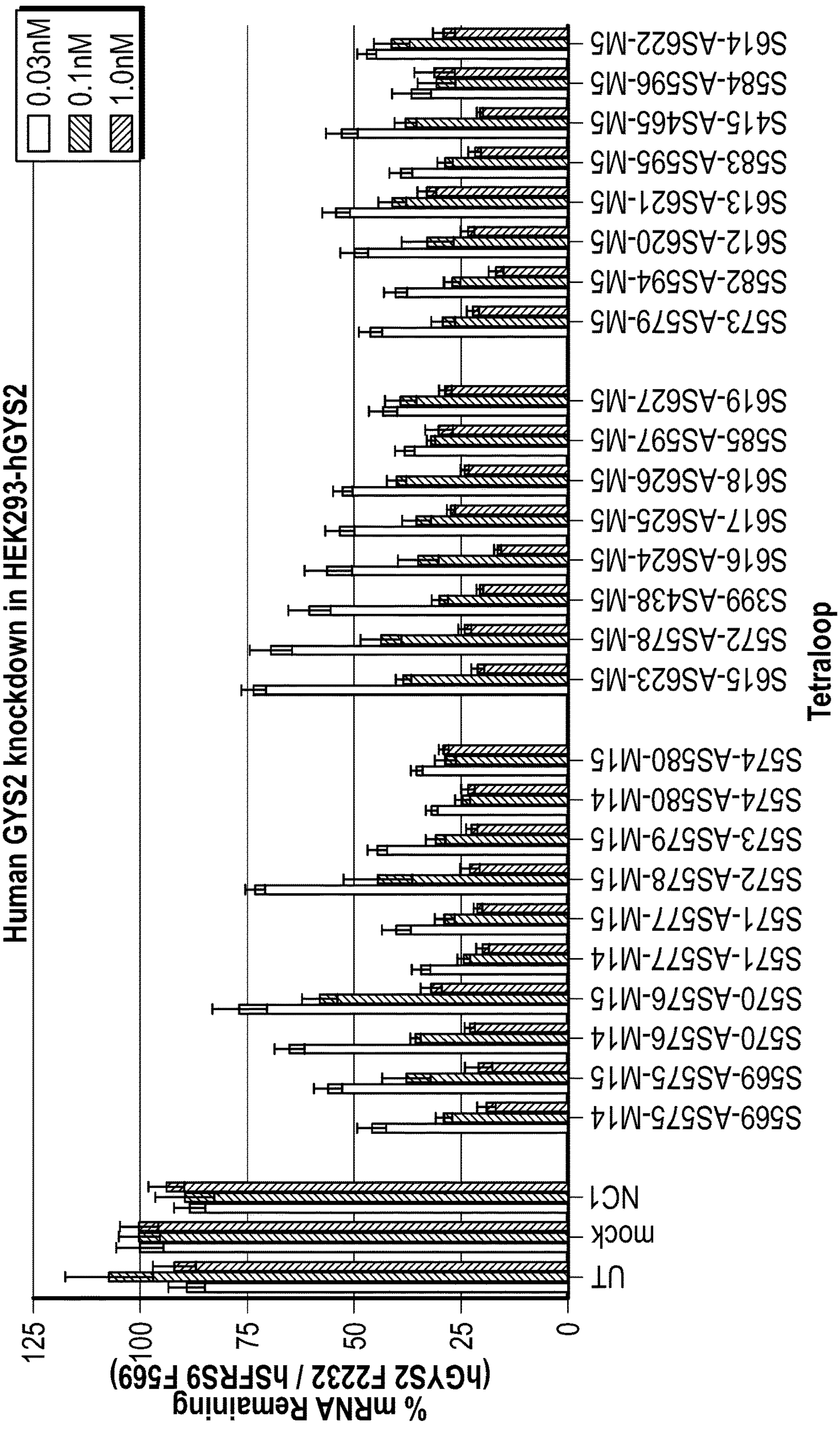
FIG. 4 is a graph showing the results of screening in HEK-293 cells using GYS2 oligonucleotides of different base sequences in one or two different modification patterns. The X-axis lists the 3' end of the sense strand targeted by the oligonucleotide evaluated. A negative control sequence (NC1), untransfected cells, and mock transfected cells are shown at left as controls.

FIG. 4 shows data for oligonucleotides made from different base sequences with nicked tetraloop structures, each adapted to one or two different modification patterns. The X-axis lists the 3' end of the sense strand targeted by the oligonucleotide evaluated. The target mRNA levels were normalized as described above to generate the percent mRNA shown in FIG. 4, and the tested oligonucleotides are shown compared to negative control sequences (NC1) and mock transfection.

Figure 5:
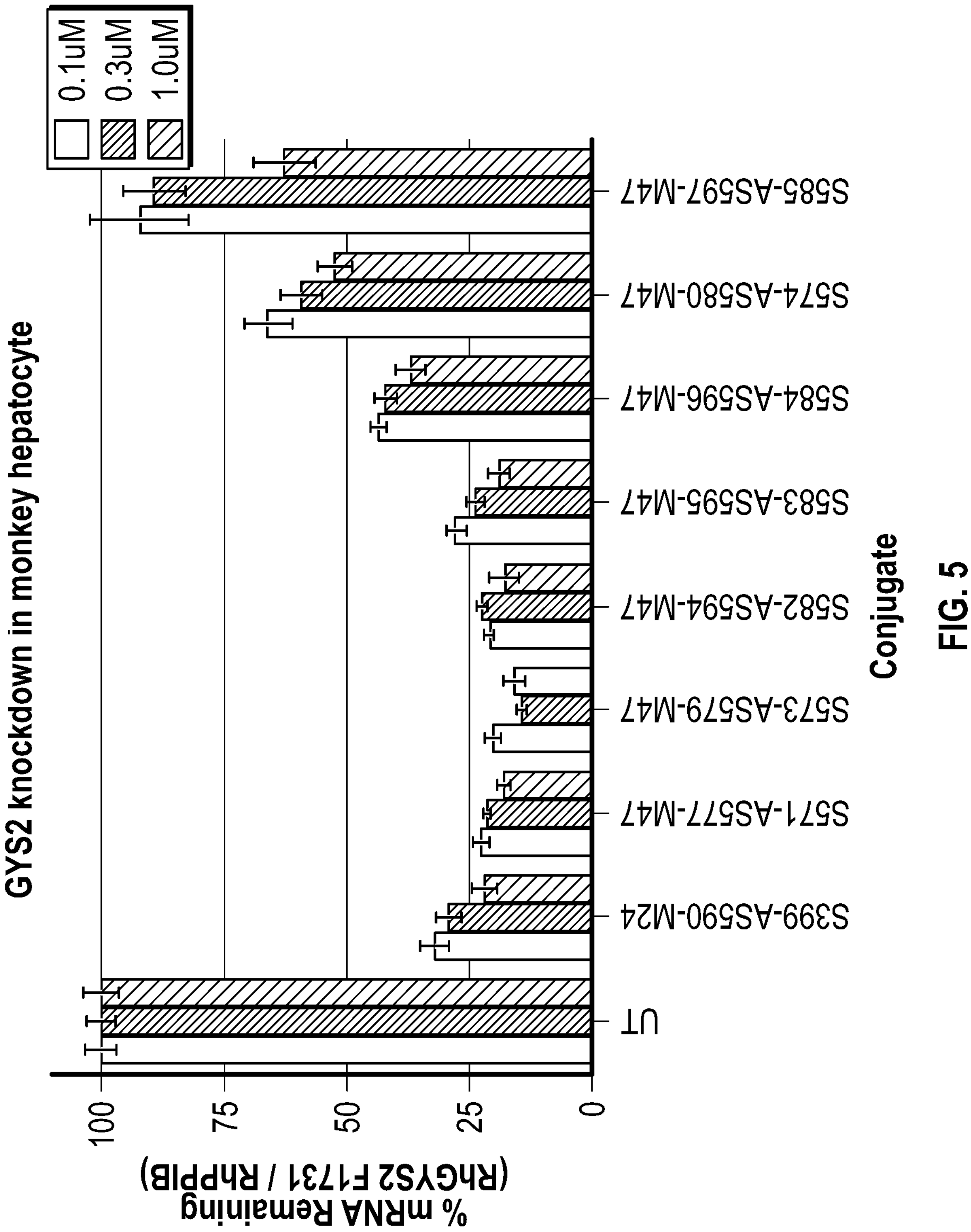
FIG. 5 is a graph showing the results of screening in monkey hepatocyte cells using GYS2 oligonucleotides of different base sequences in the nicked tetraloop structure. The same modification pattern was used, and the oligonucleotides were tested at three different concentrations (0.1 μM, 0.3 μM, and 1.0 μM). Untransfected cells are shown as a control at left.
Figure 6A:
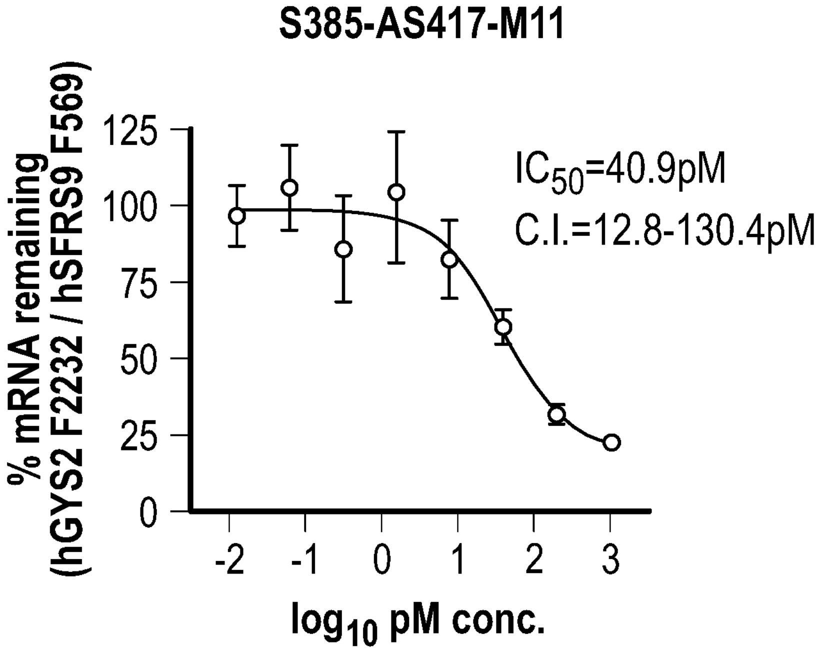
FIGS. 6A and 6B are a series of graphs showing the $IC_{50}$ results for GYS2 oligonucleotides selected from dose response curve screening in HEK-293 cells.
Figure 6A:
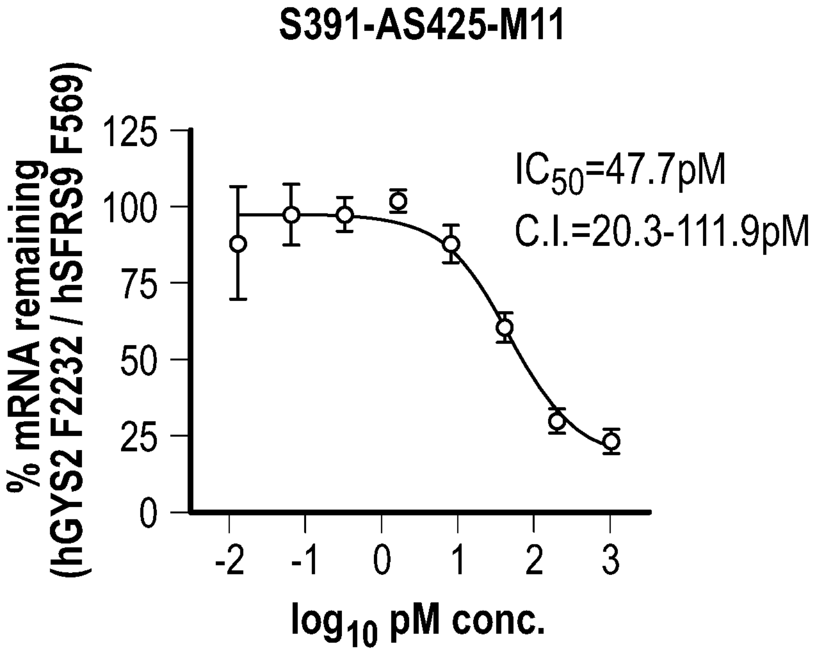
Figure 6A:
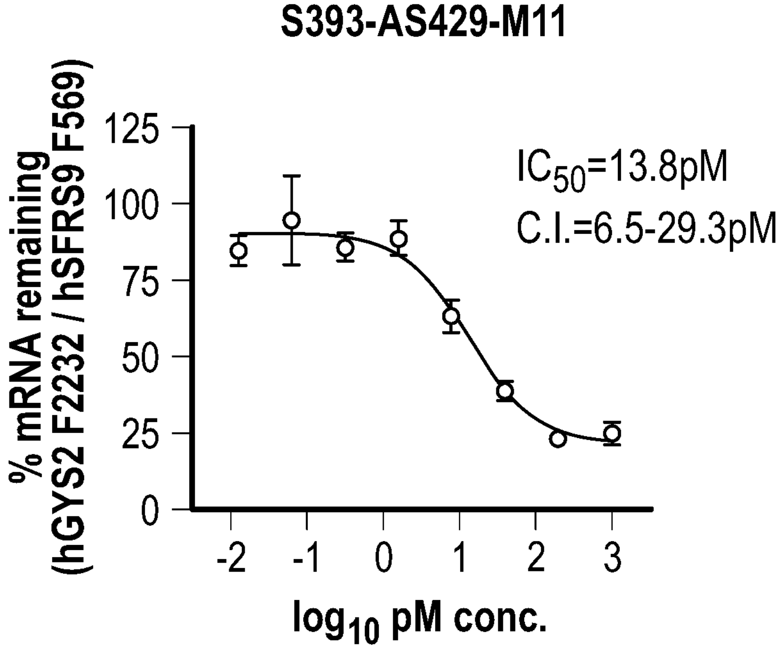
Figure 6A:
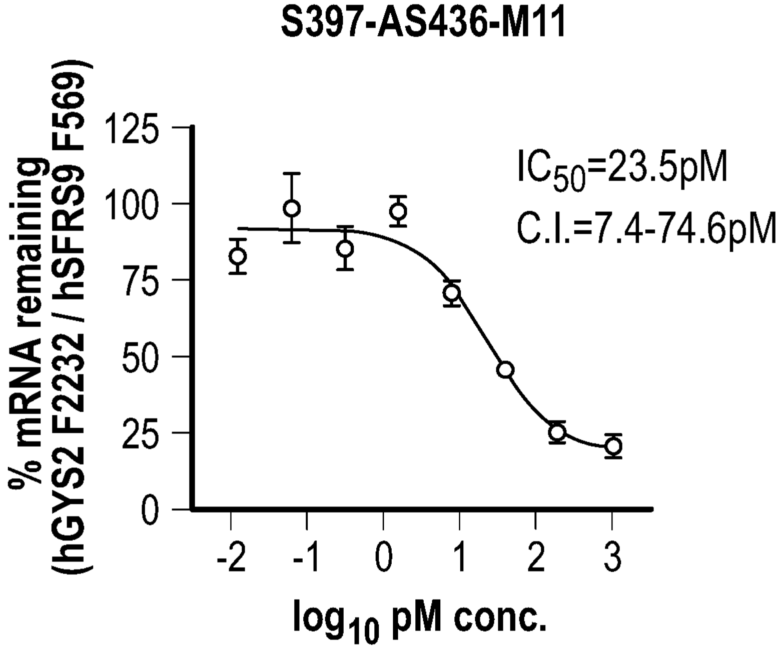
Figure 6A:
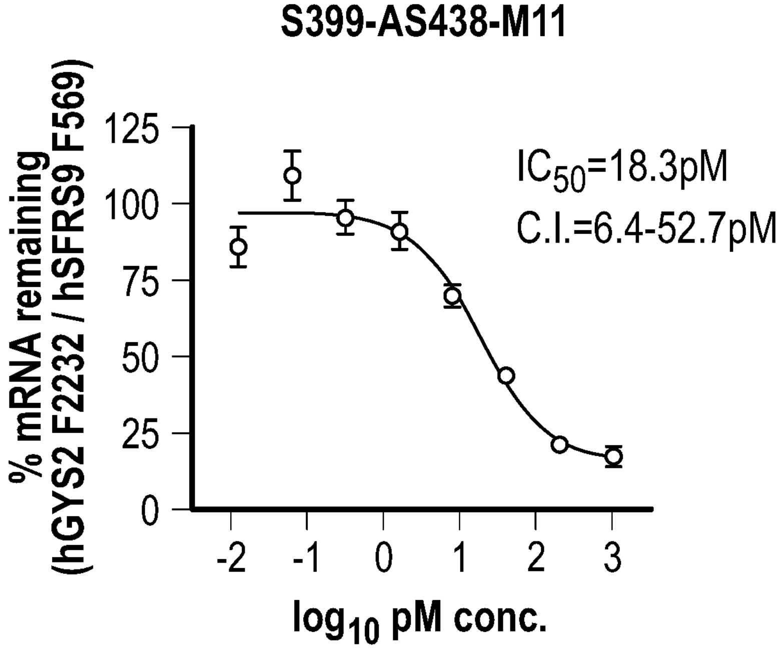
Figure 6A:
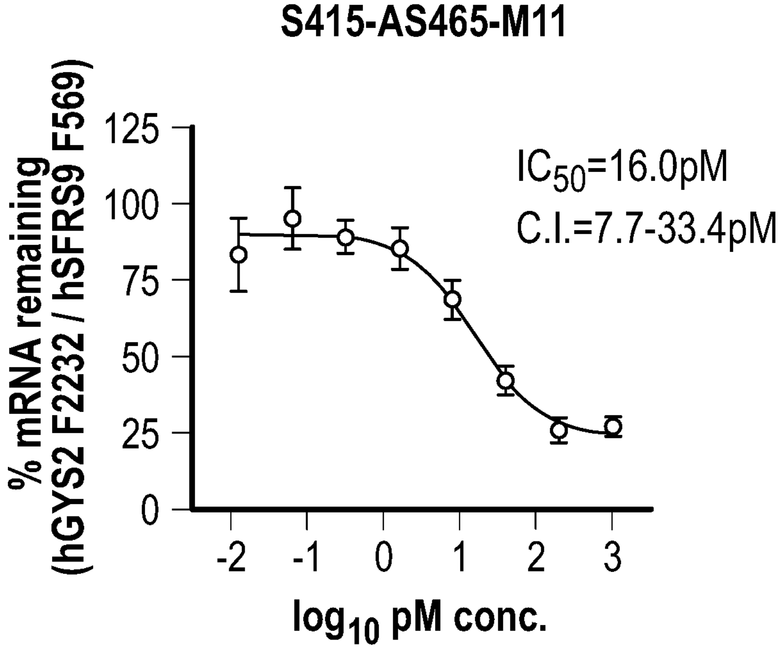
Figure 6B:
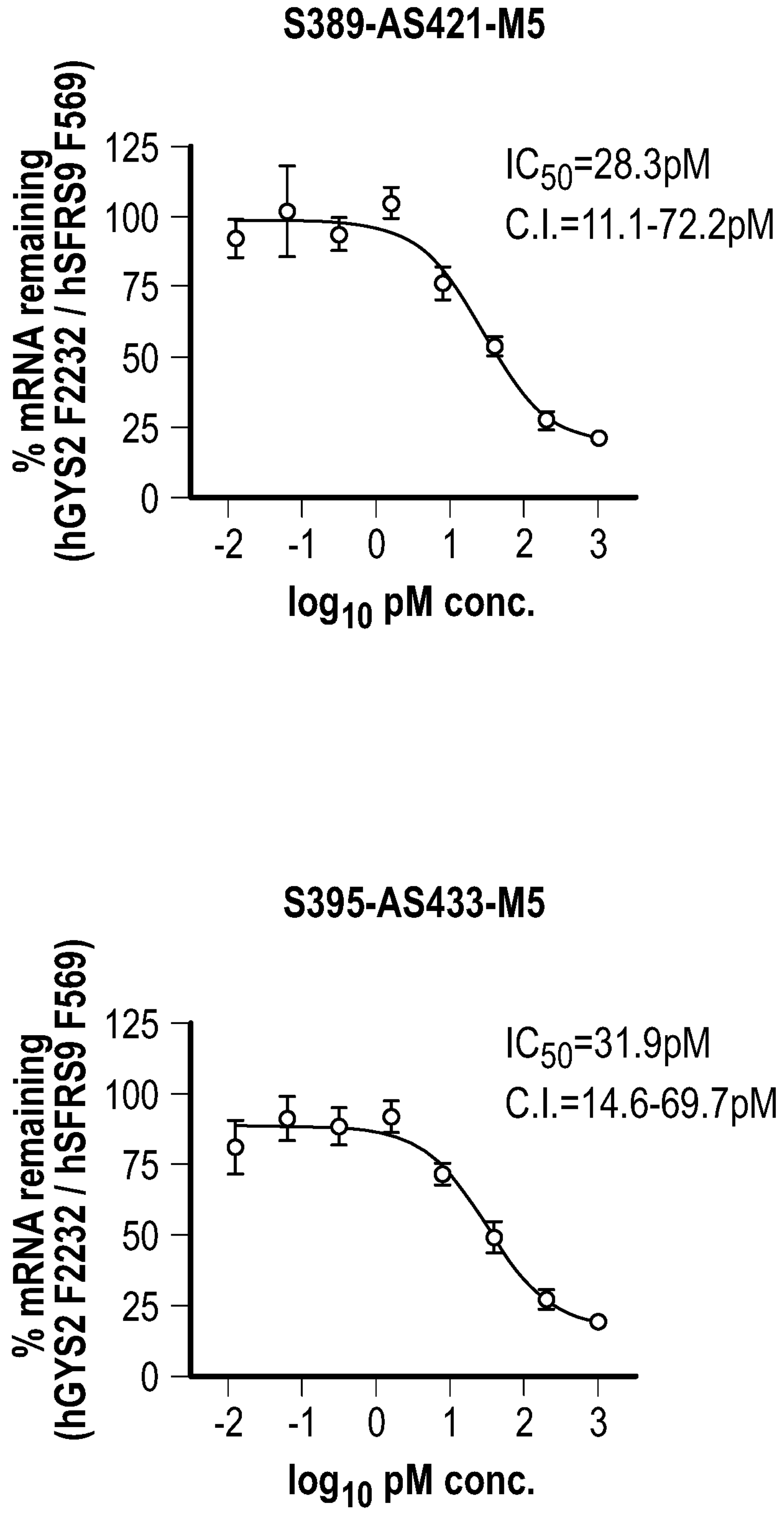
Figure 6B:
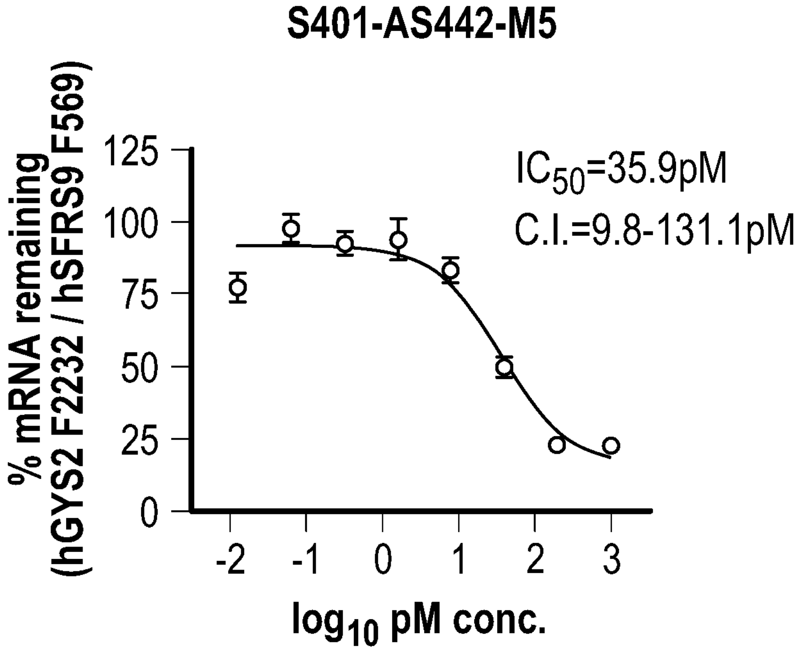
Figure 6B:
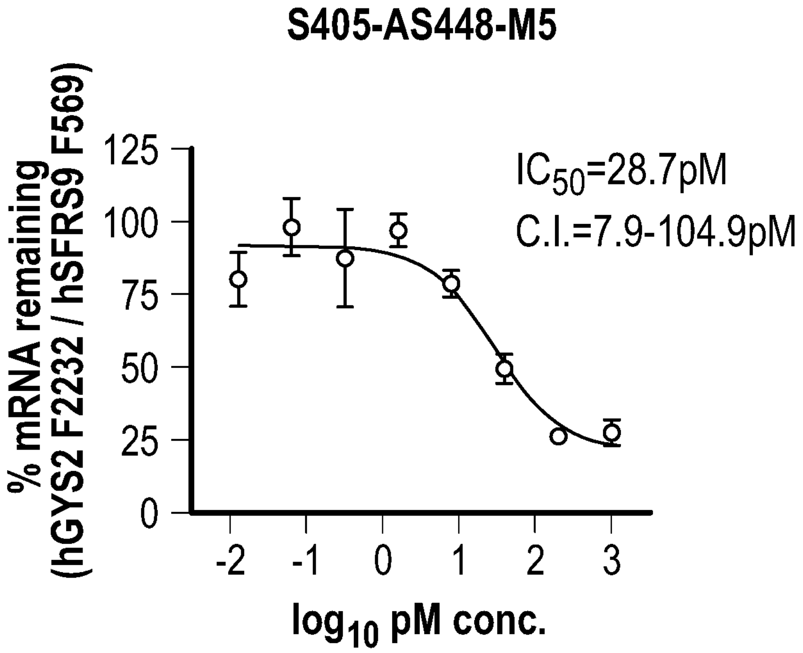
Figure 6B:
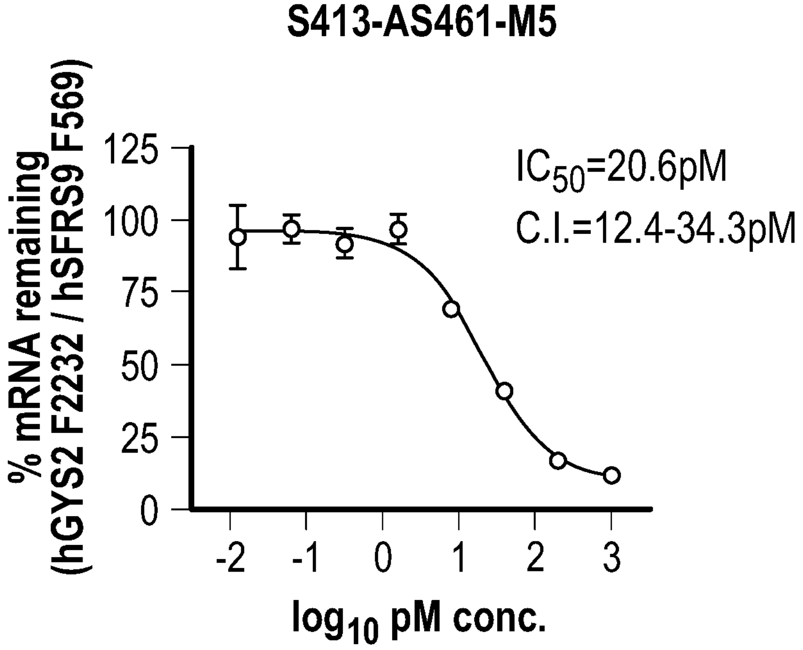
Figure 6B:
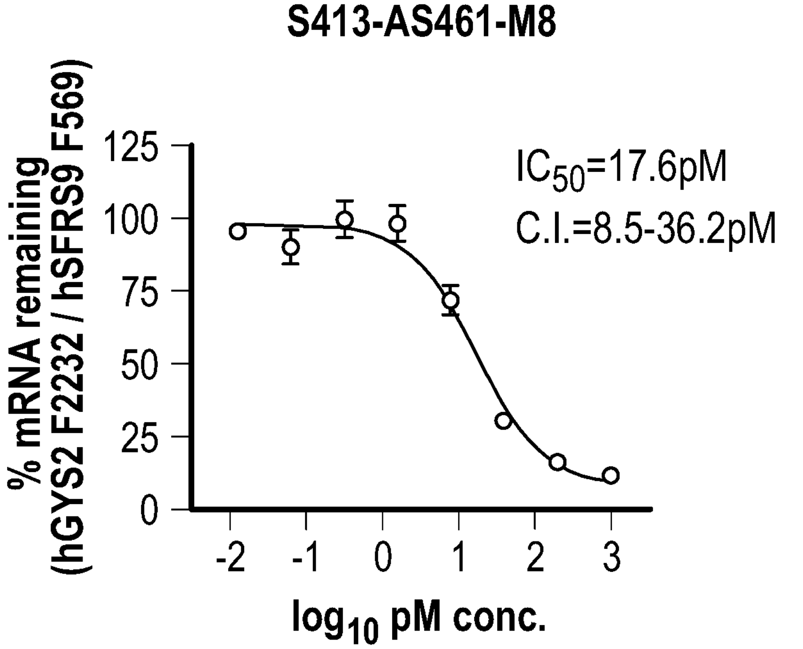

Certain tetraloop-modified oligonucleotides were further tested in monkey hepatocyte cells using the same modification patterns for each compound (FIG. 5) at 0.1 μM, 0.3 μM, and 1.0 μM. The tested oligonucleotides in FIG. 5 are shown compared untransfected cells. Certain oligonucleotides were further tested using a full dose response curve in HEK-293 cells in order to determine the half maximal inhibitory concentration ($IC_{50}$) for each compound (see FIGS. 6A and 6B).

In Vivo Murine Screening

Data from the above in vitro experiments were assessed to identify tetraloops and modification patterns that would improve delivery properties while maintaining activity for reduction of GYS2 expression in the mouse hepatocytes. Based on this analysis, select oligonucleotides were then conjugated to GalNAc moieties. Four GalNAc moieties were conjugated to nucleotides in the tetraloop of the sense strand. Conjugation was performed using a click linker. The GalNAc used was as shown below:

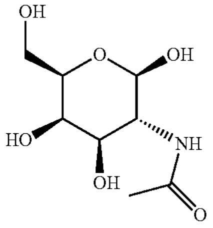

N-Acetyl-b-D-galactosamine
(CAS#: 14131-60-3)

A total of 65 potent GalNAc-conjugated GYS2 oligonucleotides from 18 different base sequences and having different modification patterns with nicked tetraloop structures were tested. Selected GYS2 oligonucleotide sequences were active against human and monkey mRNA sequences but not mouse Gys2. GYS2 oligonucleotides were subcutaneously administered to CD-1 mice transiently expressing human GYS2 mRNA by hydrodynamic injection of a human GYS2 expression plasmid at 0.5-5 mg/kg. Mice were euthanized on day 4 following administration. Liver samples were obtained and RNA was extracted to evaluate GYS2 mRNA levels by RT-qPCR. The percent GYS2 mRNA as compared to PBS control mRNA was determined based on these measurements.

Figure 7:
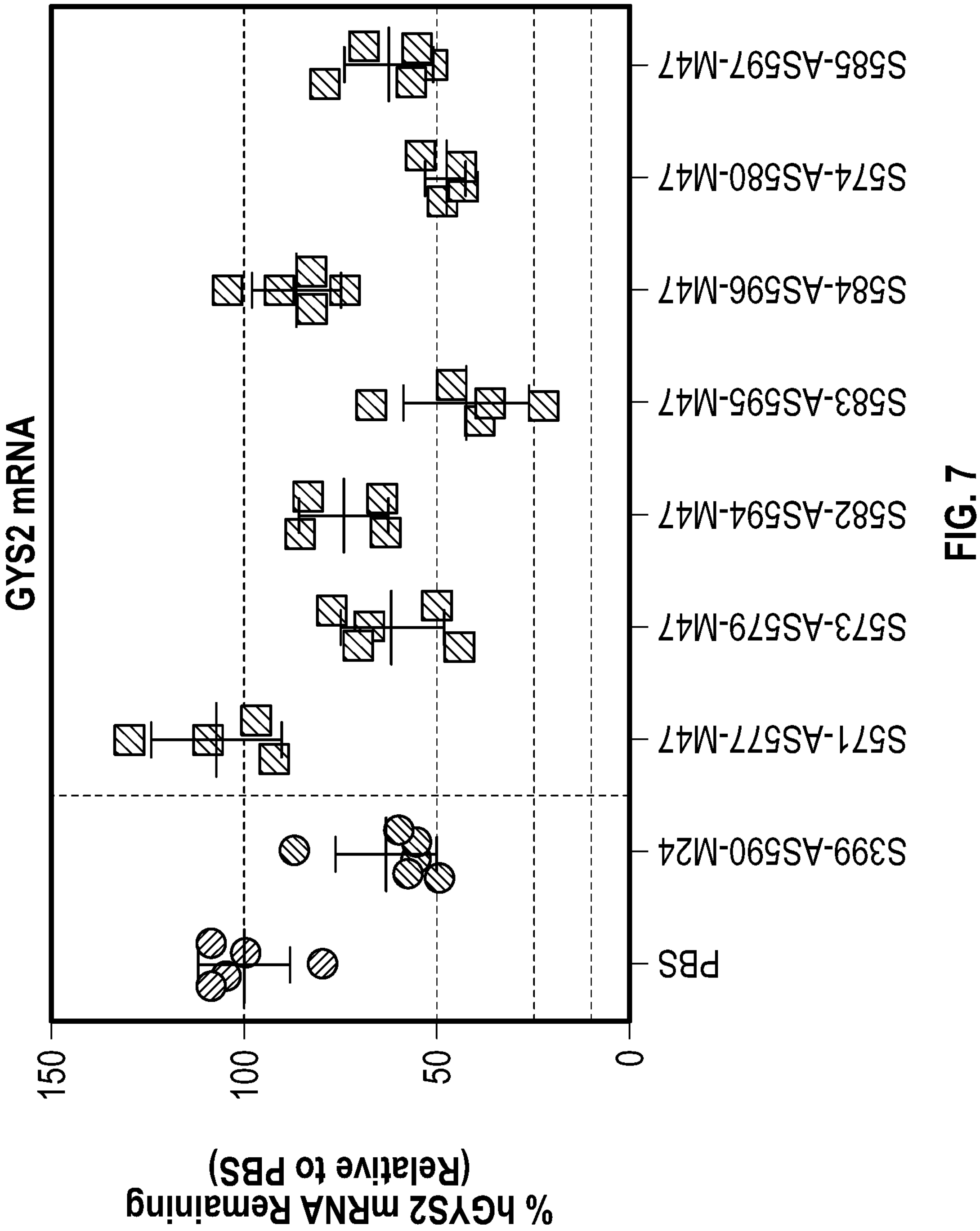
FIG. 7 is a graph showing an in vivo activity evaluation of GalNAc-conjugated GYS2 oligonucleotides in a nicked tetraloop structure. Eight different oligonucleotide sequences were tested. Oligonucleotides were subcutaneously administered to mice expressed human GYS2, at 0.5 mg/kg. The data show the amount of GYS2 mRNA remaining at day 4 following administration normalized to PBS control.

From the 65 conjugates tested, the eight most potent base sequences were identified and each tested with the same modification pattern by subcutaneous injection at 0.5 mg/kg to CD-1 mice transiently expressing human GYS2 mRNA. Mice were euthanized on day 4 following administration. Liver samples were obtained and RNA was extracted to evaluate GYS2 mRNA levels by RT-qPCR. The percent GYS2 mRNA as compared to PBS control mRNA was determined based on these measurements and is shown in FIG. 7.

Materials and Methods

Transfection

For the first screen, Lipofectamine RNAiMAX™ was used to complex the oligonucleotides for efficient transfection. Oligonucleotides, RNAiMAX and Opti-MEM incubated together at room temperature for 20 minutes and then 50 μL of this mix was added per well to plates prior to transfection. Media was aspirated from a flask of actively passaging cells and the cells were incubated at 37° C. in the presence of trypsin for 3-5 minutes. After cells no longer adhered to the flask, cell growth media (lacking penicillin and streptomycin) was added to neutralize the trypsin and to suspend the cells. A 10 μL aliquot was removed and counted with a hemocytometer to quantify the cells on a per milliliter basis. For cells, 10,000 or 25,000 cells/well were seeded per well in media (e.g., 100 μL of media). A diluted cell suspension was added to the 96-well transfection plates, which already contained the oligonucleotides in Opti-MEM. The transfection plates were then incubated for 24 hours at 37° C. After 24 hours of incubation, media was aspirated from each well. Cells were lysed using the lysis buffer from the Promega RNA Isolation kit. The lysis buffer was added to each well. The lysed cells were then transferred to the Corbett XtractorGENE (QIAxtractor) for RNA isolation or stored at −80° C.

For subsequent screens and experiments, e.g., the secondary screen, Lipofectamine RNAiMAx was used to complex the oligonucleotides for reverse transfection. The complexes were made by mixing RNAiMAX and siRNAs in OptiMEM medium for 15 minutes. The transfection mixture was transferred to multi-well plates and cell suspension was added to the wells. After 24 hours incubation the cells were washed once with PBS and then lysed using lysis buffer from the Promega SV96 kit. The RNA was purified using the SV96 plates in a vacuum manifold. Four microliters of the purified RNA was then heated at 65° C. for 5 minutes and cooled to 4° C. The RNA was then used for reverse transcription using the High Capacity Reverse Transcription kit (Life Technologies) in a 10 microliter reaction. The cDNA was then diluted to 50 μL with nuclease free water and used for quantitative PCR with multiplexed 5'-endonuclease assays and SSoFast qPCR mastermix (Bio-Rad laboratories).

cDNA Synthesis

RNA was isolated from mammalian cells in tissue culture using the Corbett X-tractor Gene™ (QIAxtractor). A modified SuperScript II protocol was used to synthesize cDNA from the isolated RNA. Isolated RNA (approximately 5 ng/μL) was heated to 65° C. for five minutes and incubated with dNPs, random hexamers, oligo dTs, and water. The mixture was cooled for 15 seconds. An "enzyme mix," consisting of water, 5× first strand buffer, DTT, SUPERase In™ (an RNA inhibitor), and SuperScript II RTase was added to the mixture. The contents were heated to 42° C. for one hour, then to 70° C. for 15 minutes, and then cooled to 4° C. using a thermocycler. The resulting cDNA was then subjected to SYBR®-based qPCR. The qPCR reactions were multiplexed, containing two 5' endonuclease assays per reaction.

qPCR Assays

Primer sets were initially screened using SYBR®-based qPCR. Assay specificity was verified by assessing melt curves as well as "minus RT" controls. Dilutions of cDNA template (10-fold serial dilutions from 20 ng and to 0.02 ng per reaction) from HeLa and Hepa1-6 cells were used to test human (Hs) and mouse (Mm) assays, respectively. qPCR assays were set up in 384-well plates, covered with MicroAmp film, and run on the 7900HT from Applied Biosystems. Reagent concentrations and cycling conditions included the following: 2×SYBR mix, 10 μM forward primer, 10 μM reverse primer, DD $H_2O$, and cDNA template up to a total volume of 10 μL.

Cloning

PCR amplicons that displayed a single melt-curve were ligated into the pGEM®-T Easy vector kit from Promega according to the manufacturer's instructions. Following the manufacturer's protocol, JM109 High Efficiency cells were transformed with the newly ligated vectors. The cells were then plated on LB plates containing ampicillin and incubated at 37° C. overnight for colony growth.

PCR Screening and Plasmid Mini-Prep

PCR was used to identify colonies of *E. coli* that had been transformed with a vector containing the ligated amplicon of interest. Vector-specific primers that flank the insert were used in the PCR reaction. All PCR products were then run on a 10% agarose gel and imaged by a transilluminator following staining. Gels were assessed qualitatively to determine which plasmids appeared to contain a ligated amplicon of the expected size (approximately 300 bp, including the amplicon and the flanking vector sequences specific to the primers used).

The colonies that were confirmed transformants by PCR screening were then incubated overnight in cultures consisting of 2 mL LB broth with ampicillin at 37° C. with shaking. *E. coli* cells were then lysed, and the plasmids of interest were isolated using Promega's Mini-Prep kit. Plasmid concentration was determined by UV absorbance at 260 nm.

Plasmid Sequencing and Quantification

Purified plasmids were sequenced using the BigDye® Terminator sequencing kit. The vector-specific primer, T7, was used to give read lengths that span the insert. The following reagents were used in the sequencing reactions: water, 5× sequencing buffer, BigDye terminator mix, T7 primer, and plasmid (100 ng/μL) to a volume of 10 μL. The mixture was held at 96° C. for one minute, then subjected to 15 cycles of 96° C. for 10 seconds, 50° C. for 5 seconds, 60° C. for 1 minute, 15 seconds; 5 cycles of 96° C. for 10 seconds, 50° C. for 5 seconds, 60° C. for 1 minute, 30 seconds; and 5 cycles of 96° C. for 10 seconds, 50° C. for 5 seconds, and 60° C. for 2 minutes. Dye termination reactions were then sequenced using Applied Biosystems' capillary electrophoresis sequencers.

Sequence-verified plasmids were then quantified. They were linearized using a single cutting restriction endonuclease. Linearity was confirmed using agarose gel electrophoresis. All plasmid dilutions were made in TE buffer (pH 7.5) with 100 μg of tRNA per mL buffer to reduce non-specific binding of plasmid to the polypropylene vials.

The linearized plasmids were then serially diluted from 1,000,000 to 01 copies per μL and subjected to qPCR. Assay efficiency was calculated and the assays were deemed acceptable if the efficiency was in the range of 90-110%.

Multi-Plexing Assays

For each target, mRNA levels were quantified by two 5' nuclease assays. In general, several assays are screened for each target. The two assays selected displayed a combination of good efficiency, low limit of detection, and broad 5'→3' coverage of the gene of interest (GOI). Both assays against one GOI could be combined in one reaction when different fluorophores were used on the respective probes. Thus, the final step in assay validation was to determine the efficiency of the selected assays when they were combined in the same qPCR or "multi-plexed."

Linearized plasmids for both assays in 10-fold dilutions were combined and qPCR was performed. The efficiency of each assay was determined as described above. The accepted efficiency rate was 90-110%. While validating multi-plexed reactions using linearized plasmid standards, $C_q$ values for the target of interest were also assessed using cDNA as the template. For human or mouse targets, HeLa and Hepa1-6 cDNA were used, respectively. The cDNA, in this case, was derived from RNA isolated on the Corbett (~5 ng/μl in water) from untransfected cells. In this way, the observed $C_q$ values from this sample cDNA were representative of the expected $C_q$ values from a 96-well plate transfection. In cases where $C_q$ values were greater than 30, other cell lines were sought that exhibit higher expression levels of the gene of interest. A library of total RNA isolated from via high-throughput methods on the Corbett from each human and mouse line was generated and used to screen for acceptable levels of target expression.

Description of Oligonucleotide Nomenclature

All oligonucleotides described herein are designated either $SN_1$-$ASN_2$-$MN_3$. The following designations apply:

$N_1$: sequence identifier number of the sense strand sequence $N_2$: sequence identifier number of the antisense strand sequence $N_3$: reference number of modification pattern, in which each number represents a pattern of modified nucleotides in the oligonucleotide.

For example, S27-AS219-M1 represents an oligonucleotide with a sense sequence that is set forth by SEQ ID NO: 27, an antisense sequence that is set forth by SEQ ID NO: 219, and which is adapted to a modification pattern identified as M1.

TABLE 4

GYS2 RNAi oligonucleotides

| App Name | Sense Sequence | S SEQ ID NO | Antisense Sequence | AS SEQ ID NO |
|---|---|---|---|---|
| S1-AS193-M1 | CAGGUGCAUUUUGGAAGAUGGCUGA | 1 | UCAGCCAUCUUCCAAAAUGCACCUGGC | 193 |
| S2-AS194-M1 | AGGUGCAUUUUGGAAGAUGGCUGAT | 2 | AUCAGCCAUCUUCCAAAAUGCACCUGG | 194 |
| S3-AS195-M1 | GGUGCAUUUUGGAAGAUGGCUGATA | 3 | UAUCAGCCAUCUUCCAAAAUGCACCUG | 195 |
| S4-AS196-M1 | GUGCAUUUUGGAAGAUGGCUGAUAG | 4 | CUAUCAGCCAUCUUCCAAAAUGCACCU | 196 |
| S5-AS197-M1 | UGCAUUUUGGAAGAUGGCUGAUAGA | 5 | UCUAUCAGCCAUCUUCCAAAAUGCACC | 197 |
| S6-AS198-M1 | AAGGAAGUCCUUAUGUGGUACUUTT | 6 | AAAAGUACCACAUAAGGACUUCCUUCU | 198 |
| S7-AS199-M1 | GAAGUCCUUAUGUGGUACUUUUUGA | 7 | UCAAAAAGUACCACAUAAGGACUUCCU | 199 |
| S8-AS200-M1 | AAGUCCUUAUGUGGUACUUUUUGAC | 8 | GUCAAAAAGUACCACAUAAGGACUUCC | 200 |
| S9-AS201-M1 | AGUCCUUAUGUGGUACUUUUUGACA | 9 | UGUCAAAAAGUACCACAUAAGGACUUC | 201 |
| S10-AS202-M1 | GUCCUUAUGUGGUACUUUUUGACAT | 10 | AUGUCAAAAAGUACCACAUAAGGACUU | 202 |
| S11-AS203-M1 | CCUUAUGUGGUACUUUUUGACAUAG | 11 | CUAUGUCAAAAAGUACCACAUAAGGAC | 203 |
| S12-AS204-M1 | GUACUUUUUGACAUAGGCUAUUCAG | 12 | CUGAAUAGCCUAUGUCAAAAAGUACCA | 204 |
| S13-AS205-M1 | CGAGAAGCCAAUGAUAUGCUGAUAT | 13 | AUAUCAGCAUAUCAUUGGCUUCUCGGU | 205 |
| S14-AS206-M1 | GAGAAGCCAAUGAUAUGCUGAUATT | 14 | AAUAUCAGCAUAUCAUUGGCUUCUCGG | 206 |
| S15-AS207-M1 | AGAAGCCAAUGAUAUGCUGAUAUTT | 15 | AAAUAUCAGCAUAUCAUUGGCUUCUCG | 207 |
| S16-AS208-M1 | GAAGCCAAUGAUAUGCUGAUAUUTG | 16 | CAAAUAUCAGCAUAUCAUUGGCUUCUC | 208 |
| S17-AS209-M1 | AGCCAAUGAUAUGCUGAUAUUUGGA | 17 | UCCAAAUAUCAGCAUAUCAUUGGCUUC | 209 |
| S18-AS210-M1 | GCCAAUGAUAUGCUGAUAUUUGGAT | 18 | AUCCAAAUAUCAGCAUAUCAUUGGCUU | 210 |
| S19-AS211-M1 | CCAAUGAUAUGCUGAUAUUUGGATC | 19 | GAUCCAAAUAUCAGCAUAUCAUUGGCU | 211 |
| S20-AS212-M1 | AAUGAUAUGCUGAUAUUUGGAUCTT | 20 | AAGAUCCAAAUAUCAGCAUAUCAUUGG | 212 |
| S21-AS213-M1 | AUGAUAUGCUGAUAUUUGGAUCUTT | 21 | AAAGAUCCAAAUAUCAGCAUAUCAUUG | 213 |
| S22-AS214-M1 | UGAUAUGCUGAUAUUUGGAUCUUTA | 22 | UAAAGAUCCAAAUAUCAGCAUAUCAUU | 214 |
| S23-AS215-M1 | AUAUGCUGAUAUUUGGAUCUUUAAC | 23 | GUUAAAGAUCCAAAUAUCAGCAUAUCA | 215 |
| S24-AS216-M1 | AUGCUGAUAUUUGGAUCUUUAACTG | 24 | CAGUUAAAGAUCCAAAUAUCAGCAUAU | 216 |
| S25-AS217-M1 | UCUUUAACUGCCUGGUUCUUAAAAG | 25 | CUUUUAAGAACCAGGCAGUUAAAGAUC | 217 |
| S26-AS218-M1 | CUUUAACUGCCUGGUUCUUAAAAGA | 26 | UCUUUUAAGAACCAGGCAGUUAAAGAU | 218 |
| S27-AS219-M1 | UUUAACUGCCUGGUUCUUAAAAGAG | 27 | CUCUUUUAAGAACCAGGCAGUUAAAGA | 219 |
| S28-AS220-M1 | UUAACUGCCUGGUUCUUAAAAGAGG | 28 | CCUCUUUUAAGAACCAGGCAGUUAAAG | 220 |
| S29-AS221-M1 | UAACUGCCUGGUUCUUAAAAGAGGT | 29 | ACCUCUUUUAAGAACCAGGCAGUUAAA | 221 |
| S30-AS222-M1 | UUGCCCAAUUCCAUGAAUGGCAGGC | 30 | GCCUGCCAUUCAUGGAAUUGGGCAACG | 222 |
| S31-AS223-M1 | UGCCCAAUUCCAUGAAUGGCAGGCT | 31 | AGCCUGCCAUUCAUGGAAUUGGGCAAC | 223 |

TABLE 4-continued

GYS2 RNAi oligonucleotides

| App Name | Sense Sequence | S SEQ ID NO | Antisense Sequence | AS SEQ ID NO |
|---|---|---|---|---|
| S32-AS224-M1 | GCCCAAUUCCAUGAAUGGCAGGCTG | 32 | CAGCCUGCCAUUCAUGGAAUUGGGCAA | 224 |
| S33-AS225-M1 | CCCAAUUCCAUGAAUGGCAGGCUGG | 33 | CCAGCCUGCCAUUCAUGGAAUUGGGCA | 225 |
| S34-AS226-M1 | CCAAUUCCAUGAAUGGCAGGCUGGA | 34 | UCCAGCCUGCCAUUCAUGGAAUUGGGC | 226 |
| S35-AS227-M1 | CAAUUCCAUGAAUGGCAGGCUGGAA | 35 | UUCCAGCCUGCCAUUCAUGGAAUUGGG | 227 |
| S36-AS228-M1 | AAUUCCAUGAAUGGCAGGCUGGAAT | 36 | AUUCCAGCCUGCCAUUCAUGGAAUUGG | 228 |
| S37-AS229-M1 | AUUCCAUGAAUGGCAGGCUGGAATT | 37 | AAUUCCAGCCUGCCAUUCAUGGAAUUG | 229 |
| S38-AS230-M1 | UUCCAUGAAUGGCAGGCUGGAAUTG | 38 | CAAUUCCAGCCUGCCAUUCAUGGAAUU | 230 |
| S39-AS231-M1 | UCCAUGAAUGGCAGGCUGGAAUUGG | 39 | CCAAUUCCAGCCUGCCAUUCAUGGAAU | 231 |
| S40-AS232-M1 | GGAAACUUCCUAUUGCCACAAUATT | 40 | AAUAUUGUGGCAAUAGGAAGUUUCCUG | 232 |
| S41-AS233-M1 | GGUAUCUCUGUGCAGCAAAUAUUGA | 41 | UCAAUAUUUGCUGCACAGAGAUACCUC | 233 |
| S42-AS234-M1 | GUAUCUCUGUGCAGCAAAUAUUGAT | 42 | AUCAAUAUUUGCUGCACAGAGAUACCU | 234 |
| S43-AS235-M1 | UAUCUCUGUGCAGCAAAUAUUGATT | 43 | AAUCAAUAUUUGCUGCACAGAGAUACC | 235 |
| S44-AS236-M1 | AUCUCUGUGCAGCAAAUAUUGAUTT | 44 | AAAUCAAUAUUUGCUGCACAGAGAUAC | 236 |
| S45-AS237-M1 | UCUCUGUGCAGCAAAUAUUGAUUTC | 45 | GAAAUCAAUAUUUGCUGCACAGAGAUA | 237 |
| S46-AS238-M1 | CUCUGUGCAGCAAAUAUUGAUUUCT | 46 | AGAAAUCAAUAUUUGCUGCACAGAGAU | 238 |
| S47-AS239-M1 | UCUGUGCAGCAAAUAUUGAUUUCTA | 47 | UAGAAAUCAAUAUUUGCUGCACAGAGA | 239 |
| S48-AS240-M1 | CUGUGCAGCAAAUAUUGAUUUCUAC | 48 | GUAGAAAUCAAUAUUUGCUGCACAGAG | 240 |
| S49-AS241-M1 | UGUGCAGCAAAUAUUGAUUUCUACA | 49 | UGUAGAAAUCAAUAUUUGCUGCACAGA | 241 |
| S50-AS242-M1 | GUGCAGCAAAUAUUGAUUUCUACAA | 50 | UUGUAGAAAUCAAUAUUUGCUGCACAG | 242 |
| S51-AS243-M1 | UGCAGCAAAUAUUGAUUUCUACAAC | 51 | GUUGUAGAAAUCAAUAUUUGCUGCACA | 243 |
| S52-AS244-M1 | GCAGCAAAUAUUGAUUUCUACAACC | 52 | GGUUGUAGAAAUCAAUAUUUGCUGCAC | 244 |
| S53-AS245-M1 | CAGCAAAUAUUGAUUUCUACAACCA | 53 | UGGUUGUAGAAAUCAAUAUUUGCUGCA | 245 |
| S54-AS246-M1 | AGCAAAUAUUGAUUUCUACAACCAT | 54 | AUGGUUGUAGAAAUCAAUAUUUGCUGC | 246 |
| S55-AS247-M1 | GCAAAUAUUGAUUUCUACAACCATC | 55 | GAUGGUUGUAGAAAUCAAUAUUUGCUG | 247 |
| S56-AS248-M1 | AUAUUGAUUUCUACAACCAUCUUGA | 56 | UCAAGAUGGUUGUAGAAAUCAAUAUUU | 248 |
| S57-AS249-M1 | UUGAUUUCUACAACCAUCUUGAUAA | 57 | UUAUCAAGAUGGUUGUAGAAAUCAAUA | 249 |
| S58-AS250-M1 | GAUUUCUACAACCAUCUUGAUAAGT | 58 | ACUUAUCAAGAUGGUUGUAGAAAUCAA | 250 |
| S59-AS251-M1 | AUUUCUACAACCAUCUUGAUAAGTT | 59 | AACUUAUCAAGAUGGUUGUAGAAAUCA | 251 |
| S60-AS252-M1 | UUCUACAACCAUCUUGAUAAGUUTA | 60 | UAAACUUAUCAAGAUGGUUGUAGAAAU | 252 |
| S61-AS253-M1 | CUACAACCAUCUUGAUAAGUUUAAC | 61 | GUUAAACUUAUCAAGAUGGUUGUAGAA | 253 |
| S62-AS254-M1 | UACAACCAUCUUGAUAAGUUUAACA | 62 | UGUUAAACUUAUCAAGAUGGUUGUAGA | 254 |
| S63-AS255-M1 | ACAACCAUCUUGAUAAGUUUAACAT | 63 | AUGUUAAACUUAUCAAGAUGGUUGUAG | 255 |
| S64-AS256-M1 | CAACCAUCUUGAUAAGUUUAACATT | 64 | AAUGUUAAACUUAUCAAGAUGGUUGUA | 256 |
| S65-AS257-M1 | AACCAUCUUGAUAAGUUUAACAUTG | 65 | CAAUGUUAAACUUAUCAAGAUGGUUGU | 257 |
| S66-AS258-M1 | ACCAUCUUGAUAAGUUUAACAUUGA | 66 | UCAAUGUUAAACUUAUCAAGAUGGUUG | 258 |
| S67-AS259-M1 | CCAUCUUGAUAAGUUUAACAUUGAC | 67 | GUCAAUGUUAAACUUAUCAAGAUGGUU | 259 |
| S68-AS260-M1 | CAUCUUGAUAAGUUUAACAUUGACA | 68 | UGUCAAUGUUAAACUUAUCAAGAUGGU | 260 |

TABLE 4-continued

GYS2 RNAi oligonucleotides

| App Name | Sense Sequence | S SEQ ID NO | Antisense Sequence | AS SEQ ID NO |
|---|---|---|---|---|
| S69-AS261-M1 | AUCUUGAUAAGUUUAACAUUGACAA | 69 | UUGUCAAUGUUAAACUUAUCAAGAUGG | 261 |
| S70-AS262-M1 | GUUCACCACGGUUUCUGAAAUAACA | 70 | UGUUAUUUCAGAAACCGUGGUGAACAC | 262 |
| S71-AS263-M1 | CACCACGGUUUCUGAAAUAACAGCA | 71 | UGCUGUUAUUUCAGAAACCGUGGUGAA | 263 |
| S72-AS264-M1 | CCACGGUUUCUGAAAUAACAGCAAT | 72 | AUUGCUGUUAUUUCAGAAACCGUGGUG | 264 |
| S73-AS265-M1 | CACGGUUUCUGAAAUAACAGCAATA | 73 | UAUUGCUGUUAUUUCAGAAACCGUGGU | 265 |
| S74-AS266-M1 | CGGUUUCUGAAAUAACAGCAAUAGA | 74 | UCUAUUGCUGUUAUUUCAGAAACCGUG | 266 |
| S75-AS267-M1 | GGUUUCUGAAAUAACAGCAAUAGAA | 75 | UUCUAUUGCUGUUAUUUCAGAAACCGU | 267 |
| S76-AS268-M1 | GUUUCUGAAAUAACAGCAAUAGAAG | 76 | CUUCUAUUGCUGUUAUUUCAGAAACCG | 268 |
| S77-AS269-M1 | CUGAAAUAACAGCAAUAGAAGCUGA | 77 | UCAGCUUCUAUUGCUGUUAUUUCAGAA | 269 |
| S78-AS270-M1 | AAGAGAAAGCCUGAUGUAGUUACTC | 78 | GAGUAACUACAUCAGGCUUUCUCUUCA | 270 |
| S79-AS271-M1 | AGAGAAAGCCUGAUGUAGUUACUCC | 79 | GGAGUAACUACAUCAGGCUUUCUCUUC | 271 |
| S80-AS272-M1 | GGCUUGAAUGUUAAGAAAUUUUCAG | 80 | CUGAAAAUUUCUUAACAUUCAAGCCGU | 272 |
| S81-AS273-M1 | GCUUGAAUGUUAAGAAAUUUUCAGC | 81 | GCUGAAAAUUUCUUAACAUUCAAGCCG | 273 |
| S82-AS274-M1 | CUUGAAUGUUAAGAAAUUUUCAGCA | 82 | UGCUGAAAAUUUCUUAACAUUCAAGCC | 274 |
| S83-AS275-M1 | UUGAAUGUUAAGAAAUUUUCAGCAG | 83 | CUGCUGAAAAUUUCUUAACAUUCAAGC | 275 |
| S84-AS276-M1 | UGAAUGUUAAGAAAUUUUCAGCAGT | 84 | ACUGCUGAAAAUUUCUUAACAUUCAAG | 276 |
| S85-AS277-M1 | GAAUGUUAAGAAAUUUUCAGCAGTG | 85 | CACUGCUGAAAAUUUCUUAACAUUCAA | 277 |
| S86-AS278-M1 | AUGUUAAGAAAUUUUCAGCAGUGCA | 86 | UGCACUGCUGAAAAUUUCUUAACAUUC | 278 |
| S87-AS279-M1 | AGAAAUUUUCAGCAGUGCAUGAGTT | 87 | AACUCAUGCACUGCUGAAAAUUUCUUA | 279 |
| S88-AS280-M1 | AGCAGUGCAUGAGUUUCAAAAUCTA | 88 | UAGAUUUUGAAACUCAUGCACUGCUGA | 280 |
| S89-AS281-M1 | AGAUUUUGUUCGAGGUCAUUUCUAT | 89 | AUAGAAAUGACCUCGAACAAAAUCUUG | 281 |
| S90-AS282-M1 | GUUCGAGGUCAUUUCUAUGGUCATC | 90 | GAUGACCAUAGAAAUGACCUCGAACAA | 282 |
| S91-AS283-M1 | UUCGAGGUCAUUUCUAUGGUCAUCT | 91 | AGAUGACCAUAGAAAUGACCUCGAACA | 283 |
| S92-AS284-M1 | UCGAGGUCAUUUCUAUGGUCAUCTC | 92 | GAGAUGACCAUAGAAAUGACCUCGAAC | 284 |
| S93-AS285-M1 | CGAGGUCAUUUCUAUGGUCAUCUCG | 93 | CGAGAUGACCAUAGAAAUGACCUCGAA | 285 |
| S94-AS286-M1 | GAGGUCAUUUCUAUGGUCAUCUCGA | 94 | UCGAGAUGACCAUAGAAAUGACCUCGA | 286 |
| S95-AS287-M1 | AGGUCAUUUCUAUGGUCAUCUCGAC | 95 | GUCGAGAUGACCAUAGAAAUGACCUCG | 287 |
| S96-AS288-M1 | GGUCAUUUCUAUGGUCAUCUCGACT | 96 | AGUCGAGAUGACCAUAGAAAUGACCUC | 288 |
| S97-AS289-M1 | GUCAUUUCUAUGGUCAUCUCGACTT | 97 | AAGUCGAGAUGACCAUAGAAAUGACCU | 289 |
| S98-AS290-M1 | UGAAAAGACUUUGUUCCUUUUCATT | 98 | AAUGAAAAGGAACAAAGUCUUUUCAAG | 290 |
| S99-AS291-M1 | GAAAAGACUUUGUUCCUUUUCAUTG | 99 | CAAUGAAAAGGAACAAAGUCUUUUCAA | 291 |
| S100-AS292-M1 | AAAGACUUUGUUCCUUUUCAUUGCT | 100 | AGCAAUGAAAAGGAACAAAGUCUUUUC | 292 |
| S101-AS293-M1 | CUGAGGAUGCAUAAAAGUGACAUCA | 101 | UGAUGUCACUUUUAUGCAUCCUCAGCA | 293 |
| S102-AS294-M1 | GAGGAUGCAUAAAAGUGACAUCACA | 102 | UGUGAUGUCACUUUUAUGCAUCCUCAG | 294 |
| S103-AS295-M1 | UUUUUCAUUAUGCCUGCCAAGACAA | 103 | UUGUCUUGGCAGGCAUAAUGAAAAACA | 295 |
| S104-AS296-M1 | UCAUUAUGCCUGCCAAGACAAAUAA | 104 | UUAUUUGUCUUGGCAGGCAUAAUGAAA | 296 |
| S105-AS297-M1 | CAUUAUGCCUGCCAAGACAAAUAAT | 105 | AUUAUUUGUCUUGGCAGGCAUAAUGAA | 297 |

TABLE 4-continued

GYS2 RNAi oligonucleotides

| App Name | Sense Sequence | S SEQ ID NO | Antisense Sequence | AS SEQ ID NO |
|---|---|---|---|---|
| S106-AS298-M1 | AUUAUGCCUGCCAAGACAAAUAATT | 106 | AAUUAUUUGUCUUGGCAGGCAUAAUGA | 298 |
| S107-AS299-M1 | AUGCCUGCCAAGACAAAUAAUUUCA | 107 | UGAAAUUAUUUGUCUUGGCAGGCAUAA | 299 |
| S108-AS300-M1 | AAUUUCAACGUGGAAACCCUGAAAG | 108 | CUUUCAGGGUUUCCACGUUGAAAUUAU | 300 |
| S109-AS301-M1 | AUUUCAACGUGGAAACCCUGAAAGG | 109 | CCUUUCAGGGUUUCCACGUUGAAAUUA | 301 |
| S110-AS302-M1 | UUUCAACGUGGAAACCCUGAAAGGA | 110 | UCCUUUCAGGGUUUCCACGUUGAAAUU | 302 |
| S111-AS303-M1 | UUCAACGUGGAAACCCUGAAAGGAC | 111 | GUCCUUUCAGGGUUUCCACGUUGAAAU | 303 |
| S112-AS304-M1 | UCAACGUGGAAACCCUGAAAGGACA | 112 | UGUCCUUUCAGGGUUUCCACGUUGAAA | 304 |
| S113-AS305-M1 | UUGCACAUUCUGUGAAGGAAAAGTT | 113 | AACUUUUCCUUCACAGAAUGUGCAACA | 305 |
| S114-AS306-M1 | UGCACAUUCUGUGAAGGAAAAGUTT | 114 | AAACUUUUCCUUCACAGAAUGUGCAAC | 306 |
| S115-AS307-M1 | GCACAUUCUGUGAAGGAAAAGUUTG | 115 | CAAACUUUUCCUUCACAGAAUGUGCAA | 307 |
| S116-AS308-M1 | AUUCUGUGAAGGAAAAGUUUGGAAA | 116 | UUUCCAAACUUUUCCUUCACAGAAUGU | 308 |
| S117-AS309-M1 | GUGAAGGAAAAGUUUGGAAAAAAAC | 117 | GUUUUUUUCCAAACUUUUCCUUCACAG | 309 |
| S118-AS310-M1 | GAAAAAAACUCUAUGAUGCAUUATT | 118 | AAUAAUGCAUCAUAGAGUUUUUUUCCA | 310 |
| S119-AS311-M1 | AAAAAAACUCUAUGAUGCAUUAUTA | 119 | UAAUAAUGCAUCAUAGAGUUUUUUUCC | 311 |
| S120-AS312-M1 | AAAAAACUCUAUGAUGCAUUAUUAA | 120 | UUAAUAAUGCAUCAUAGAGUUUUUUUC | 312 |
| S121-AS313-M1 | AAAAACUCUAUGAUGCAUUAUUAAG | 121 | CUUAAUAAUGCAUCAUAGAGUUUUUUU | 313 |
| S122-AS314-M1 | UUAUUAAGAGGAGAAAUUCCUGACC | 122 | GGUCAGGAAUUUCUCCUCUUAAUAAUG | 314 |
| S123-AS315-M1 | UAUUAAGAGGAGAAAUUCCUGACCT | 123 | AGGUCAGGAAUUUCUCCUCUUAAUAAU | 315 |
| S124-AS316-M1 | AUUAAGAGGAGAAAUUCCUGACCTG | 124 | CAGGUCAGGAAUUUCUCCUCUUAAUAA | 316 |
| S125-AS317-M1 | UUAAGAGGAGAAAUUCCUGACCUGA | 125 | UCAGGUCAGGAAUUUCUCCUCUUAAUA | 317 |
| S126-AS318-M1 | UAAGAGGAGAAAUUCCUGACCUGAA | 126 | UUCAGGUCAGGAAUUUCUCCUCUUAAU | 318 |
| S127-AS319-M1 | AAGAGGAGAAAUUCCUGACCUGAAC | 127 | GUUCAGGUCAGGAAUUUCUCCUCUUAA | 319 |
| S128-AS320-M1 | CGAGAUGAUCUAACAAUUAUGAAAA | 128 | UUUUCAUAAUUGUUAGAUCAUCUCGAU | 320 |
| S129-AS321-M1 | AGAUGAUCUAACAAUUAUGAAAAGA | 129 | UCUUUUCAUAAUUGUUAGAUCAUCUCG | 321 |
| S130-AS322-M1 | GAUGAUCUAACAAUUAUGAAAAGAG | 130 | CUCUUUUCAUAAUUGUUAGAUCAUCUC | 322 |
| S131-AS323-M1 | AUGAUCUAACAAUUAUGAAAAGAGC | 131 | GCUCUUUUCAUAAUUGUUAGAUCAUCU | 323 |
| S132-AS324-M1 | ACAAUUAUGAAAAGAGCCAUCUUTT | 132 | AAAAGAUGGCUCUUUUCAUAAUUGUUA | 324 |
| S133-AS325-M1 | GAAAAGAGCCAUCUUUUCAACUCAG | 133 | CUGAGUUGAAAAGAUGGCUCUUUUCAU | 325 |
| S134-AS326-M1 | CCCAUCCUCAGCACCAUUAGACGGA | 134 | UCCGUCUAAUGGUGCUGAGGAUGGGGU | 326 |
| S135-AS327-M1 | CCAUCCUCAGCACCAUUAGACGGAT | 135 | AUCCGUCUAAUGGUGCUGAGGAUGGGG | 327 |
| S136-AS328-M1 | CAUCCUCAGCACCAUUAGACGGATT | 136 | AAUCCGUCUAAUGGUGCUGAGGAUGGG | 328 |
| S137-AS329-M1 | AUCCUCAGCACCAUUAGACGGAUTG | 137 | CAAUCCGUCUAAUGGUGCUGAGGAUGG | 329 |
| S138-AS330-M1 | UCCUCAGCACCAUUAGACGGAUUGG | 138 | CCAAUCCGUCUAAUGGUGCUGAGGAUG | 330 |
| S139-AS331-M1 | CCCAUGGACUAUGAAGAGUUUGUTA | 139 | UAACAAACUCUUCAUAGUCCAUGGGUA | 331 |
| S140-AS332-M1 | CCAUGGACUAUGAAGAGUUUGUUAG | 140 | CUAACAAACUCUUCAUAGUCCAUGGGU | 332 |
| S141-AS333-M1 | CUUGGAGUAUUUCCAUCAUACUATG | 141 | CAUAGUAUGAUGGAAAUACUCCAAGAU | 333 |
| S142-AS334-M1 | UGGAGUAUUUCCAUCAUACUAUGAA | 142 | UUCAUAGUAUGAUGGAAAUACUCCAAG | 334 |
| S143- | GGAGUAUUUCCAUCAUACUAUGAAC | 143 | GUUCAUAGUAUGAUGGAA | 335 |

TABLE 4-continued

| GYS2 RNAi oligonucleotides | | | | |
|---|---|---|---|---|
| App Name | Sense Sequence | S SEQ ID NO | Antisense Sequence | AS SEQ ID NO |
| AS335-M1 | | | AUACUCCAA | |
| S144-AS336-M1 | GAGUAUUUCCAUCAUACUAUGAACC | 144 | GGUUCAUAGUAUGAUGGAAAUACUCCA | 336 |
| S145-AS337-M1 | UAUUUCCAUCAUACUAUGAACCCTG | 145 | CAGGGUUCAUAGUAUGAUGGAAAUACU | 337 |
| S146-AS338-M1 | AUACUCCAGCUGAAUGCACUGUGAT | 146 | AUCACAGUGCAUUCAGCUGGAGUAUAA | 338 |
| S147-AS339-M1 | GGCAGAUAUUACCAGCAUGCCAGAC | 147 | GUCUGGCAUGCUGGUAAUAUCUGCCUA | 339 |
| S148-AS340-M1 | GCAGAUAUUACCAGCAUGCCAGACA | 148 | UGUCUGGCAUGCUGGUAAUAUCUGCCU | 340 |
| S149-AS341-M1 | CAGAUAUUACCAGCAUGCCAGACAC | 149 | GUGUCUGGCAUGCUGGUAAUAUCUGCC | 341 |
| S150-AS342-M1 | AGAUAUUACCAGCAUGCCAGACACC | 150 | GGUGUCUGGCAUGCUGGUAAUAUCUGC | 342 |
| S151-AS343-M1 | GAUAUUACCAGCAUGCCAGACACCT | 151 | AGGUGUCUGGCAUGCUGGUAAUAUCUG | 343 |
| S152-AS344-M1 | AUAUUACCAGCAUGCCAGACACCTG | 152 | CAGGUGUCUGGCAUGCUGGUAAUAUCU | 344 |
| S153-AS345-M1 | UAUUACCAGCAUGCCAGACACCUGA | 153 | UCAGGUGUCUGGCAUGCUGGUAAUAUC | 345 |
| S154-AS346-M1 | AUUACCAGCAUGCCAGACACCUGAC | 154 | GUCAGGUGUCUGGCAUGCUGGUAAUAU | 346 |
| S155-AS347-M1 | UUACCAGCAUGCCAGACACCUGACA | 155 | UGUCAGGUGUCUGGCAUGCUGGUAAUA | 347 |
| S156-AS348-M1 | UACCAGCAUGCCAGACACCUGACAT | 156 | AUGUCAGGUGUCUGGCAUGCUGGUAAU | 348 |
| S157-AS349-M1 | ACCAGCAUGCCAGACACCUGACATT | 157 | AAUGUCAGGUGUCUGGCAUGCUGGUAA | 349 |
| S158-AS350-M1 | CCAGCAUGCCAGACACCUGACAUTA | 158 | UAAUGUCAGGUGUCUGGCAUGCUGGUA | 350 |
| S159-AS351-M1 | CAGCAUGCCAGACACCUGACAUUAA | 159 | UUAAUGUCAGGUGUCUGGCAUGCUGGU | 351 |
| S160-AS352-M1 | AGCAUGCCAGACACCUGACAUUAAG | 160 | CUUAAUGUCAGGUGUCUGGCAUGCUGG | 352 |
| S161-AS353-M1 | GCAUGCCAGACACCUGACAUUAAGC | 161 | GCUUAAUGUCAGGUGUCUGGCAUGCUG | 353 |
| S162-AS354-M1 | UGCCAGACACCUGACAUUAAGCAGA | 162 | UCUGCUUAAUGUCAGGUGUCUGGCAUG | 354 |
| S163-AS355-M1 | CCUGACAUUAAGCAGAGCUUUUCCA | 163 | UGGAAAAGCUCUGCUUAAUGUCAGGUG | 355 |
| S164-AS356-M1 | AAGCAGAGCUUUUCCAGAUAAAUTC | 164 | GAAUUUAUCUGGAAAAGCUCUGCUUAA | 356 |
| S165-AS357-M1 | GCAGAGCUUUUCCAGAUAAAUUCCA | 165 | UGGAAUUUAUCUGGAAAAGCUCUGCUU | 357 |
| S166-AS358-M1 | CCAGAUAAAUUCCAUGUGGAACUAA | 166 | UUAGUUCCACAUGGAAUUUAUCUGGAA | 358 |
| S167-AS359-M1 | CAGAUAAAUUCCAUGUGGAACUAAC | 167 | GUUAGUUCCACAUGGAAUUUAUCUGGA | 359 |
| S168-AS360-M1 | UCCUCAGUACCACCUUCUCCUUCAG | 168 | CUGAAGGAGAAGGUGGUACUGAGGAAG | 360 |
| S169-AS361-M1 | CCUCAGUACCACCUUCUCCUUCAGG | 169 | CCUGAAGGAGAAGGUGGUACUGAGGAA | 361 |
| S170-AS362-M1 | GAAAGGGAUCGGUUAAAUAUCAAGT | 170 | ACUUGAUAUUUAACCGAUCCCUUUCAG | 362 |
| S171-AS363-M1 | AGGGAUCGGUUAAAUAUCAAGUCAC | 171 | GUGACUUGAUAUUUAACCGAUCCCUUU | 363 |
| S172-AS364-M1 | AUCGGUUAAAUAUCAAGUCACCATT | 172 | AAUGGUGACUUGAUAUUUAACCGAUCC | 364 |
| S173-AS365-M1 | GGUUAAAUAUCAAGUCACCAUUUTC | 173 | GAAAAUGGUGACUUGAUAUUUAACCGA | 365 |
| S174-AS366-M1 | GUUAAAUAUCAAGUCACCAUUUUCA | 174 | UGAAAAUGGUGACUUGAUAUUUAACCG | 366 |
| S175-AS367-M1 | AAAUAUCAAGUCACCAUUUUCACTG | 175 | CAGUGAAAAUGGUGACUUGAUAUUUAA | 367 |
| S176-AS368-M1 | AAGAAAAAGCUGCAUGGUGAAUATA | 176 | UAUAUUCACCAUGCAGCUUUUUCUUCC | 368 |
| S177-AS369-M1 | AGAAAAAGCUGCAUGGUGAAUAUAA | 177 | UUAUAUUCACCAUGCAGCUUUUUCUUC | 369 |
| S178-AS370-M1 | AAAAAGCUGCAUGGUGAAUAUAAGA | 178 | UCUUAUAUUCACCAUGCAGCUUUUUCU | 370 |
| S179-AS371-M1 | AAAAGCUGCAUGGUGAAUAUAAGAA | 179 | UUCUUAUAUUCACCAUGCAGCUUUUUC | 371 |
| S180-AS372-M1 | AAGCUGCAUGGUGAAUAUAAGAACT | 180 | AGUUCUUAUAUUCACCAUGCAGCUUUU | 372 |

TABLE 4-continued

GYS2 RNAi oligonucleotides

| App Name | Sense Sequence | S SEQ ID NO | Antisense Sequence | AS SEQ ID NO |
|---|---|---|---|---|
| S181-AS373-M1 | GCUGCAUGGUGAAUAUAAGAACUGA | 181 | UCAGUUCUUAUAUUCACCAUGCAGCUU | 373 |
| S182-AS374-M1 | CUGCAUGGUGAAUAUAAGAACUGAA | 182 | UUCAGUUCUUAUAUUCACCAUGCAGCU | 374 |
| S183-AS375-M1 | GCAUGGUGAAUAUAAGAACUGAATT | 183 | AAUUCAGUUCUUAUAUUCACCAUGCAG | 375 |
| S184-AS376-M1 | CAUGGUGAAUAUAAGAACUGAAUTC | 184 | GAAUUCAGUUCUUAUAUUCACCAUGCA | 376 |
| S185-AS377-M1 | AUGGUGAAUAUAAGAACUGAAUUCT | 185 | AGAAUUCAGUUCUUAUAUUCACCAUGC | 377 |
| S186-AS378-M1 | UGGUGAAUAUAAGAACUGAAUUCTA | 186 | UAGAAUUCAGUUCUUAUAUUCACCAUG | 378 |
| S187-AS379-M1 | GGUGAAUAUAAGAACUGAAUUCUAC | 187 | GUAGAAUUCAGUUCUUAUAUUCACCAU | 379 |
| S188-AS380-M1 | GUGAAUAUAAGAACUGAAUUCUACA | 188 | UGUAGAAUUCAGUUCUUAUAUUCACCA | 380 |
| S189-AS381-M1 | AAUAUAAGAACUGAAUUCUACAUGT | 189 | ACAUGUAGAAUUCAGUUCUUAUAUUCA | 381 |
| S190-AS382-M1 | AUAUAAGAACUGAAUUCUACAUGTG | 190 | CACAUGUAGAAUUCAGUUCUUAUAUUC | 382 |
| S191-AS383-M1 | AUAAGAACUGAAUUCUACAUGUGCT | 191 | AGCACAUGUAGAAUUCAGUUCUUAUAU | 383 |
| S192-AS384-M1 | AAGAACUGAAUUCUACAUGUGCUGC | 192 | GCAGCACAUGUAGAAUUCAGUUCUUAU | 384 |
| S385-AS417-M2 | AGGUGCAUUUUGGAAGAUGGGCAGCCGAAAGGCUGC | 385 | CCAUCUUCCAAAAUGCACCUGG | 417 |
| S385-AS417-M3 | AGGUGCAUUUUGGAAGAUGGGCAGCCGAAAGGCUGC | 385 | CCAUCUUCCAAAAUGCACCUGG | 417 |
| S385-AS417-M4 | AGGUGCAUUUUGGAAGAUGGGCAGCCGAAAGGCUGC | 385 | CCAUCUUCCAAAAUGCACCUGG | 417 |
| S385-AS417-M5 | AGGUGCAUUUUGGAAGAUGGGCAGCCGAAAGGCUGC | 385 | CCAUCUUCCAAAAUGCACCUGG | 417 |
| S385-AS417-M6 | AGGUGCAUUUUGGAAGAUGGGCAGCCGAAAGGCUGC | 385 | CCAUCUUCCAAAAUGCACCUGG | 417 |
| S385-AS417-M7 | AGGUGCAUUUUGGAAGAUGGGCAGCCGAAAGGCUGC | 385 | CCAUCUUCCAAAAUGCACCUGG | 417 |
| S385-AS417-M8 | AGGUGCAUUUUGGAAGAUGGGCAGCCGAAAGGCUGC | 385 | CCAUCUUCCAAAAUGCACCUGG | 417 |
| S385-AS417-M9 | AGGUGCAUUUUGGAAGAUGGGCAGCCGAAAGGCUGC | 385 | CCAUCUUCCAAAAUGCACCUGG | 417 |
| S385-AS417-M10 | AGGUGCAUUUUGGAAGAUGGGCAGCCGAAAGGCUGC | 385 | CCAUCUUCCAAAAUGCACCUGG | 417 |
| S385-AS417-M11 | AGGUGCAUUUUGGAAGAUGGGCAGCCGAAAGGCUGC | 385 | CCAUCUUCCAAAAUGCACCUGG | 417 |
| S386-AS418-M12 | AGGUGCAUUUUGGAAGAUGGCAGCCGAAAGGCUGC | 386 | CAUCUUCCAAAAUGCACCUGG | 418 |
| S386-AS418-M13 | AGGUGCAUUUUGGAAGAUGGCAGCCGAAAGGCUGC | 386 | CAUCUUCCAAAAUGCACCUGG | 418 |
| S387-AS419-M2 | GGUGCAUUUUGGAAGAUGGCGCAGCCGAAAGGCUGC | 387 | GCCAUCUUCCAAAAUGCACCUG | 419 |
| S387-AS419-M3 | GGUGCAUUUUGGAAGAUGGCGCAGCCGAAAGGCUGC | 387 | GCCAUCUUCCAAAAUGCACCUG | 419 |
| S387-AS419-M4 | GGUGCAUUUUGGAAGAUGGCGCAGCCGAAAGGCUGC | 387 | GCCAUCUUCCAAAAUGCACCUG | 419 |
| S387-AS419-M5 | GGUGCAUUUUGGAAGAUGGCGCAGCCGAAAGGCUGC | 387 | GCCAUCUUCCAAAAUGCACCUG | 419 |
| S387-AS419-M6 | GGUGCAUUUUGGAAGAUGGCGCAGCCGAAAGGCUGC | 387 | GCCAUCUUCCAAAAUGCACCUG | 419 |
| S387-AS419-M7 | GGUGCAUUUUGGAAGAUGGCGCAGCCGAAAGGCUGC | 387 | GCCAUCUUCCAAAAUGCACCUG | 419 |
| S387-AS419-M8 | GGUGCAUUUUGGAAGAUGGCGCAGCCGAAAGGCUGC | 387 | GCCAUCUUCCAAAAUGCACCUG | 419 |
| S387-AS419-M9 | GGUGCAUUUUGGAAGAUGGCGCAGCCGAAAGGCUGC | 387 | GCCAUCUUCCAAAAUGCACCUG | 419 |
| S387-AS419-M10 | GGUGCAUUUUGGAAGAUGGCGCAGCCGAAAGGCUGC | 387 | GCCAUCUUCCAAAAUGCACCUG | 419 |
| S387-AS419-M11 | GGUGCAUUUUGGAAGAUGGCGCAGCCGAAAGGCUGC | 387 | GCCAUCUUCCAAAAUGCACCUG | 419 |
| S388-AS420-M12 | GGUGCAUUUUGGAAGAUGGGCAGCCGAAAGGCUGC | 388 | CCAUCUUCCAAAAUGCACCUG | 420 |
| S388-AS420-M13 | GGUGCAUUUUGGAAGAUGGGCAGCCGAAAGGCUGC | 388 | CCAUCUUCCAAAAUGCACCUG | 420 |
| S389-AS421-M2 | AAGGAAGUCCUUAUGUGGUAGCAGCCGAAAGGCUGC | 389 | UACCACAUAAGGACUUCCUUCU | 421 |
| S389- | AAGGAAGUCCUUAUGUGGUAGCAGCC | 389 | UACCACAUAAGGACUUCCU | 421 |

TABLE 4-continued

GYS2 RNAi oligonucleotides

| App Name | Sense Sequence | S SEQ ID NO | Antisense Sequence | AS SEQ ID NO |
|---|---|---|---|---|
| AS421-M3 | GAAAGGCUGC | | UCU | |
| S389-AS421-M4 | AAGGAAGUCCUUAUGUGGUAGCAGCCGAAAGGCUGC | 389 | UACCACAUAAGGACUUCCUUCU | 421 |
| S389-AS421-M5 | AAGGAAGUCCUUAUGUGGUAGCAGCCGAAAGGCUGC | 389 | UACCACAUAAGGACUUCCUUCU | 421 |
| S389-AS422-M6 | AAGGAAGUCCUUAUGUGGUAGCAGCCGAAAGGCUGC | 389 | UACCACAUAAGGACUUCCTUCU | 422 |
| S389-AS421-M7 | AAGGAAGUCCUUAUGUGGUAGCAGCCGAAAGGCUGC | 389 | UACCACAUAAGGACUUCCUUCU | 421 |
| S389-AS421-M8 | AAGGAAGUCCUUAUGUGGUAGCAGCCGAAAGGCUGC | 389 | UACCACAUAAGGACUUCCUUCU | 421 |
| S389-AS421-M9 | AAGGAAGUCCUUAUGUGGUAGCAGCCGAAAGGCUGC | 389 | UACCACAUAAGGACUUCCUUCU | 421 |
| S389-AS421-M10 | AAGGAAGUCCUUAUGUGGUAGCAGCCGAAAGGCUGC | 389 | UACCACAUAAGGACUUCCUUCU | 421 |
| S389-AS421-M11 | AAGGAAGUCCUUAUGUGGUAGCAGCCGAAAGGCUGC | 389 | UACCACAUAAGGACUUCCUUCU | 421 |
| S390-AS423-M12 | AAGGAAGUCCUUAUGUGGUGCAGCCGAAAGGCUGC | 390 | ACCACAUAAGGACUUCCTUCU | 423 |
| S390-AS424-M13 | AAGGAAGUCCUUAUGUGGUGCAGCCGAAAGGCUGC | 390 | ACCACAUAAGGACUUCCUUCU | 424 |
| S391-AS425-M2 | AUGAUAUGCUGAUAUUUGGAGCAGCCGAAAGGCUGC | 391 | UCCAAAUAUCAGCAUAUCAUUG | 425 |
| S391-AS425-M3 | AUGAUAUGCUGAUAUUUGGAGCAGCCGAAAGGCUGC | 391 | UCCAAAUAUCAGCAUAUCAUUG | 425 |
| S391-AS425-M4 | AUGAUAUGCUGAUAUUUGGAGCAGCCGAAAGGCUGC | 391 | UCCAAAUAUCAGCAUAUCAUUG | 425 |
| S391-AS425-M5 | AUGAUAUGCUGAUAUUUGGAGCAGCCGAAAGGCUGC | 391 | UCCAAAUAUCAGCAUAUCAUUG | 425 |
| S391-AS426-M6 | AUGAUAUGCUGAUAUUUGGAGCAGCCGAAAGGCUGC | 391 | UCCAAAUAUCAGCAUATCAUUG | 426 |
| S391-AS425-M7 | AUGAUAUGCUGAUAUUUGGAGCAGCCGAAAGGCUGC | 391 | UCCAAAUAUCAGCAUAUCAUUG | 425 |
| S391-AS425-M8 | AUGAUAUGCUGAUAUUUGGAGCAGCCGAAAGGCUGC | 391 | UCCAAAUAUCAGCAUAUCAUUG | 425 |
| S391-AS425-M9 | AUGAUAUGCUGAUAUUUGGAGCAGCCGAAAGGCUGC | 391 | UCCAAAUAUCAGCAUAUCAUUG | 425 |
| S391-AS425-M10 | AUGAUAUGCUGAUAUUUGGAGCAGCCGAAAGGCUGC | 391 | UCCAAAUAUCAGCAUAUCAUUG | 425 |
| S391-AS425-M11 | AUGAUAUGCUGAUAUUUGGAGCAGCCGAAAGGCUGC | 391 | UCCAAAUAUCAGCAUAUCAUUG | 425 |
| S392-AS427-M12 | AUGAUAUGCUGAUAUUUGGGCAGCCGAAAGGCUGC | 392 | CCAAAUAUCAGCAUATCAUUG | 427 |
| S392-AS428-M13 | AUGAUAUGCUGAUAUUUGGGCAGCCGAAAGGCUGC | 392 | CCAAAUAUCAGCAUAUCAUUG | 428 |
| S393-AS429-M2 | AGCAAAUAUUGAUUUCUACAGCAGCCGAAAGGCUGC | 393 | UGUAGAAAUCAAUAUUUGCUGC | 429 |
| S393-AS429-M3 | AGCAAAUAUUGAUUUCUACAGCAGCCGAAAGGCUGC | 393 | UGUAGAAAUCAAUAUUUGCUGC | 429 |
| S393-AS429-M4 | AGCAAAUAUUGAUUUCUACAGCAGCCGAAAGGCUGC | 393 | UGUAGAAAUCAAUAUUUGCUGC | 429 |
| S393-AS429-M5 | AGCAAAUAUUGAUUUCUACAGCAGCCGAAAGGCUGC | 393 | UGUAGAAAUCAAUAUUUGCUGC | 429 |
| S393-AS430-M6 | AGCAAAUAUUGAUUUCUACAGCAGCCGAAAGGCUGC | 393 | UGUAGAAAUCAATAUUTGCUGC | 430 |
| S393-AS429-M7 | AGCAAAUAUUGAUUUCUACAGCAGCCGAAAGGCUGC | 393 | UGUAGAAAUCAAUAUUUGCUGC | 429 |
| S393-AS429-M8 | AGCAAAUAUUGAUUUCUACAGCAGCCGAAAGGCUGC | 393 | UGUAGAAAUCAAUAUUUGCUGC | 429 |
| S393-AS429-M9 | AGCAAAUAUUGAUUUCUACAGCAGCCGAAAGGCUGC | 393 | UGUAGAAAUCAAUAUUUGCUGC | 429 |
| S393-AS429-M10 | AGCAAAUAUUGAUUUCUACAGCAGCCGAAAGGCUGC | 393 | UGUAGAAAUCAAUAUUUGCUGC | 429 |
| S393-AS429-M11 | AGCAAAUAUUGAUUUCUACAGCAGCCGAAAGGCUGC | 393 | UGUAGAAAUCAAUAUUUGCUGC | 429 |
| S394-AS431-M12 | AGCAAAUAUUGAUUUCUACGCAGCCGAAAGGCUGC | 394 | GTAGAAAUCAATAUUTGCUGC | 431 |
| S394-AS432-M13 | AGCAAAUAUUGAUUUCUACGCAGCCGAAAGGCUGC | 394 | GUAGAAAUCAAUAUUUGCUGC | 432 |
| S395-AS433-M2 | CCACGGUUUCUGAAAUAACAGCAGCCGAAAGGCUGC | 395 | UGUUAUUUCAGAAACCGUGGUG | 433 |
| S395-AS433-M3 | CCACGGUUUCUGAAAUAACAGCAGCCGAAAGGCUGC | 395 | UGUUAUUUCAGAAACCGUGGUG | 433 |
| S395-AS433-M4 | CCACGGUUUCUGAAAUAACAGCAGCCGAAAGGCUGC | 395 | UGUUAUUUCAGAAACCGUGGUG | 433 |

TABLE 4-continued

GYS2 RNAi oligonucleotides

| App Name | Sense Sequence | S SEQ ID NO | Antisense Sequence | AS SEQ ID NO |
|---|---|---|---|---|
| S395-AS433-M5 | CCACGGUUUCUGAAAUAACAGCAGCCGAAAGGCUGC | 395 | UGUUAUUUCAGAAACCGUGGUG | 433 |
| S395-AS433-M6 | CCACGGUUUCUGAAAUAACAGCAGCCGAAAGGCUGC | 395 | UGUUAUUUCAGAAACCGUGGUG | 433 |
| S395-AS433-M7 | CCACGGUUUCUGAAAUAACAGCAGCCGAAAGGCUGC | 395 | UGUUAUUUCAGAAACCGUGGUG | 433 |
| S395-AS433-M8 | CCACGGUUUCUGAAAUAACAGCAGCCGAAAGGCUGC | 395 | UGUUAUUUCAGAAACCGUGGUG | 433 |
| S395-AS433-M9 | CCACGGUUUCUGAAAUAACAGCAGCCGAAAGGCUGC | 395 | UGUUAUUUCAGAAACCGUGGUG | 433 |
| S395-AS433-M10 | CCACGGUUUCUGAAAUAACAGCAGCCGAAAGGCUGC | 395 | UGUUAUUUCAGAAACCGUGGUG | 433 |
| S395-AS433-M11 | CCACGGUUUCUGAAAUAACAGCAGCCGAAAGGCUGC | 395 | UGUUAUUUCAGAAACCGUGGUG | 433 |
| S396-AS434-M12 | CCACGGUUUCUGAAAUAACGCAGCCGAAAGGCUGC | 396 | GTUAUUUCAGAAACCGUGGUG | 434 |
| S396-AS435-M13 | CCACGGUUUCUGAAAUAACGCAGCCGAAAGGCUGC | 396 | GUUAUUUCAGAAACCGUGGUG | 435 |
| S397-AS436-M2 | CUUGAAUGUUAAGAAAUUUUGCAGCCGAAAGGCUGC | 397 | AAAAUUUCUUAACAUUCAAGCC | 436 |
| S397-AS436-M3 | CUUGAAUGUUAAGAAAUUUUGCAGCCGAAAGGCUGC | 397 | AAAAUUUCUUAACAUUCAAGCC | 436 |
| S397-AS436-M4 | CUUGAAUGUUAAGAAAUUUUGCAGCCGAAAGGCUGC | 397 | AAAAUUUCUUAACAUUCAAGCC | 436 |
| S397-AS436-M5 | CUUGAAUGUUAAGAAAUUUUGCAGCCGAAAGGCUGC | 397 | AAAAUUUCUUAACAUUCAAGCC | 436 |
| S397-AS436-M6 | CUUGAAUGUUAAGAAAUUUUGCAGCCGAAAGGCUGC | 397 | AAAAUUUCUUAACAUUCAAGCC | 436 |
| S397-AS436-M7 | CUUGAAUGUUAAGAAAUUUUGCAGCCGAAAGGCUGC | 397 | AAAAUUUCUUAACAUUCAAGCC | 436 |
| S397-AS436-M8 | CUUGAAUGUUAAGAAAUUUUGCAGCCGAAAGGCUGC | 397 | AAAAUUUCUUAACAUUCAAGCC | 436 |
| S397-AS436-M9 | CUUGAAUGUUAAGAAAUUUUGCAGCCGAAAGGCUGC | 397 | AAAAUUUCUUAACAUUCAAGCC | 436 |
| S397-AS436-M10 | CUUGAAUGUUAAGAAAUUUUGCAGCCGAAAGGCUGC | 397 | AAAAUUUCUUAACAUUCAAGCC | 436 |
| S397-AS436-M11 | CUUGAAUGUUAAGAAAUUUUGCAGCCGAAAGGCUGC | 397 | AAAAUUUCUUAACAUUCAAGCC | 436 |
| S398-AS437-M12 | CUUGAAUGUUAAGAAAUUUGCAGCCGAAAGGCUGC | 398 | AAAUUUCUUAACAUUCAAGCC | 437 |
| S398-AS437-M13 | CUUGAAUGUUAAGAAAUUUGCAGCCGAAAGGCUGC | 398 | AAAUUUCUUAACAUUCAAGCC | 437 |
| S399-AS438-M2 | UGAAUGUUAAGAAAUUUUCAGCAGCCGAAAGGCUGC | 399 | UGAAAAUUUCUUAACAUUCAAG | 438 |
| S399-AS438-M3 | UGAAUGUUAAGAAAUUUUCAGCAGCCGAAAGGCUGC | 399 | UGAAAAUUUCUUAACAUUCAAG | 438 |
| S399-AS438-M4 | UGAAUGUUAAGAAAUUUUCAGCAGCCGAAAGGCUGC | 399 | UGAAAAUUUCUUAACAUUCAAG | 438 |
| S399-AS438-M5 | UGAAUGUUAAGAAAUUUUCAGCAGCCGAAAGGCUGC | 399 | UGAAAAUUUCUUAACAUUCAAG | 438 |
| S399-AS439-M6 | UGAAUGUUAAGAAAUUUUCAGCAGCCGAAAGGCUGC | 399 | UGAAAAUUUCUUAACATUCAAG | 439 |
| S399-AS438-M7 | UGAAUGUUAAGAAAUUUUCAGCAGCCGAAAGGCUGC | 399 | UGAAAAUUUCUUAACAUUCAAG | 438 |
| S399-AS438-M8 | UGAAUGUUAAGAAAUUUUCAGCAGCCGAAAGGCUGC | 399 | UGAAAAUUUCUUAACAUUCAAG | 438 |
| S399-AS438-M9 | UGAAUGUUAAGAAAUUUUCAGCAGCCGAAAGGCUGC | 399 | UGAAAAUUUCUUAACAUUCAAG | 438 |
| S399-AS438-M10 | UGAAUGUUAAGAAAUUUUCAGCAGCCGAAAGGCUGC | 399 | UGAAAAUUUCUUAACAUUCAAG | 438 |
| S399-AS438-M11 | UGAAUGUUAAGAAAUUUUCAGCAGCCGAAAGGCUGC | 399 | UGAAAAUUUCUUAACAUUCAAG | 438 |
| S400-AS440-M12 | UGAAUGUUAAGAAAUUUUCGCAGCCGAAAGGCUGC | 400 | GAAAAUUUCUUAACATUCAAG | 440 |
| S400-AS441-M13 | UGAAUGUUAAGAAAUUUUCGCAGCCGAAAGGCUGC | 400 | GAAAAUUUCUUAACAUUCAAG | 441 |
| S401-AS442-M2 | CGAGGUCAUUUCUAUGGUCAGCAGCCGAAAGGCUGC | 401 | UGACCAUAGAAAUGACCUCGAA | 442 |
| S401-AS442-M3 | CGAGGUCAUUUCUAUGGUCAGCAGCCGAAAGGCUGC | 401 | UGACCAUAGAAAUGACCUCGAA | 442 |
| S401-AS442-M4 | CGAGGUCAUUUCUAUGGUCAGCAGCCGAAAGGCUGC | 401 | UGACCAUAGAAAUGACCUCGAA | 442 |
| S401-AS442-M5 | CGAGGUCAUUUCUAUGGUCAGCAGCCGAAAGGCUGC | 401 | UGACCAUAGAAAUGACCUCGAA | 442 |
| S401- | CGAGGUCAUUUCUAUGGUCAGCAGCC | 401 | UGACCAUAGAAATGACCUC | 443 |

TABLE 4-continued

GYS2 RNAi oligonucleotides

| App Name | Sense Sequence | S SEQ ID NO | Antisense Sequence | AS SEQ ID NO |
|---|---|---|---|---|
| AS443-M6 | GAAAGGCUGC | | GAA | |
| S401-AS442-M7 | CGAGGUCAUUUCUAUGGUCAGCAGCCGAAAGGCUGC | 401 | UGACCAUAGAAAUGACCUCGAA | 442 |
| S401-AS442-M8 | CGAGGUCAUUUCUAUGGUCAGCAGCCGAAAGGCUGC | 401 | UGACCAUAGAAAUGACCUCGAA | 442 |
| S401-AS442-M9 | CGAGGUCAUUUCUAUGGUCAGCAGCCGAAAGGCUGC | 401 | UGACCAUAGAAAUGACCUCGAA | 442 |
| S401-AS442-M10 | CGAGGUCAUUUCUAUGGUCAGCAGCCGAAAGGCUGC | 401 | UGACCAUAGAAAUGACCUCGAA | 442 |
| S401-AS442-M11 | CGAGGUCAUUUCUAUGGUCAGCAGCCGAAAGGCUGC | 401 | UGACCAUAGAAAUGACCUCGAA | 442 |
| S402-AS444-M12 | CGAGGUCAUUUCUAUGGUCGCAGCCGAAAGGCUGC | 402 | GACCAUAGAAATGACCUCGAA | 444 |
| S402-AS445-M13 | CGAGGUCAUUUCUAUGGUCGCAGCCGAAAGGCUGC | 402 | GACCAUAGAAAUGACCUCGAA | 445 |
| S403-AS446-M2 | AUUCUGUGAAGGAAAAGUUUGCAGCCGAAAGGCUGC | 403 | AAACUUUUCCUUCACAGAAUGU | 446 |
| S403-AS446-M3 | AUUCUGUGAAGGAAAAGUUUGCAGCCGAAAGGCUGC | 403 | AAACUUUUCCUUCACAGAAUGU | 446 |
| S403-AS446-M4 | AUUCUGUGAAGGAAAAGUUUGCAGCCGAAAGGCUGC | 403 | AAACUUUUCCUUCACAGAAUGU | 446 |
| S403-AS446-M5 | AUUCUGUGAAGGAAAAGUUUGCAGCCGAAAGGCUGC | 403 | AAACUUUUCCUUCACAGAAUGU | 446 |
| S403-AS446-M6 | AUUCUGUGAAGGAAAAGUUUGCAGCCGAAAGGCUGC | 403 | AAACUUUUCCUUCACAGAAUGU | 446 |
| S403-AS446-M7 | AUUCUGUGAAGGAAAAGUUUGCAGCCGAAAGGCUGC | 403 | AAACUUUUCCUUCACAGAAUGU | 446 |
| S403-AS446-M8 | AUUCUGUGAAGGAAAAGUUUGCAGCCGAAAGGCUGC | 403 | AAACUUUUCCUUCACAGAAUGU | 446 |
| S403-AS446-M9 | AUUCUGUGAAGGAAAAGUUUGCAGCCGAAAGGCUGC | 403 | AAACUUUUCCUUCACAGAAUGU | 446 |
| S403-AS446-M10 | AUUCUGUGAAGGAAAAGUUUGCAGCCGAAAGGCUGC | 403 | AAACUUUUCCUUCACAGAAUGU | 446 |
| S403-AS446-M11 | AUUCUGUGAAGGAAAAGUUUGCAGCCGAAAGGCUGC | 403 | AAACUUUUCCUUCACAGAAUGU | 446 |
| S404-AS447-M12 | AUUCUGUGAAGGAAAAGUUGCAGCCGAAAGGCUGC | 404 | AACUUUUCCUUCACAGAAUGU | 447 |
| S404-AS447-M13 | AUUCUGUGAAGGAAAAGUUGCAGCCGAAAGGCUGC | 404 | AACUUUUCCUUCACAGAAUGU | 447 |
| S405-AS448-M2 | CUUGGAGUAUUUCCAUCAUAGCAGCCGAAAGGCUGC | 405 | UAUGAUGGAAAUACUCCAAGAU | 448 |
| S405-AS448-M3 | CUUGGAGUAUUUCCAUCAUAGCAGCCGAAAGGCUGC | 405 | UAUGAUGGAAAUACUCCAAGAU | 448 |
| S405-AS448-M4 | CUUGGAGUAUUUCCAUCAUAGCAGCCGAAAGGCUGC | 405 | UAUGAUGGAAAUACUCCAAGAU | 448 |
| S405-AS448-M5 | CUUGGAGUAUUUCCAUCAUAGCAGCCGAAAGGCUGC | 405 | UAUGAUGGAAAUACUCCAAGAU | 448 |
| S405-AS448-M6 | CUUGGAGUAUUUCCAUCAUAGCAGCCGAAAGGCUGC | 405 | UAUGAUGGAAAUACUCCAAGAU | 448 |
| S405-AS448-M7 | CUUGGAGUAUUUCCAUCAUAGCAGCCGAAAGGCUGC | 405 | UAUGAUGGAAAUACUCCAAGAU | 448 |
| S405-AS448-M8 | CUUGGAGUAUUUCCAUCAUAGCAGCCGAAAGGCUGC | 405 | UAUGAUGGAAAUACUCCAAGAU | 448 |
| S405-AS448-M9 | CUUGGAGUAUUUCCAUCAUAGCAGCCGAAAGGCUGC | 405 | UAUGAUGGAAAUACUCCAAGAU | 448 |
| S405-AS448-M10 | CUUGGAGUAUUUCCAUCAUAGCAGCCGAAAGGCUGC | 405 | UAUGAUGGAAAUACUCCAAGAU | 448 |
| S405-AS448-M11 | CUUGGAGUAUUUCCAUCAUAGCAGCCGAAAGGCUGC | 405 | UAUGAUGGAAAUACUCCAAGAU | 448 |
| S406-AS449-M12 | CUUGGAGUAUUUCCAUCAUGCAGCCGAAAGGCUGC | 406 | ATGAUGGAAAUACUCCAAGAU | 449 |
| S406-AS450-M13 | CUUGGAGUAUUUCCAUCAUGCAGCCGAAAGGCUGC | 406 | AUGAUGGAAAUACUCCAAGAU | 450 |
| S407-AS451-M2 | UGGAGUAUUUCCAUCAUACUGCAGCCGAAAGGCUGC | 407 | AGUAUGAUGGAAAUACUCCAAG | 451 |
| S407-AS451-M3 | UGGAGUAUUUCCAUCAUACUGCAGCCGAAAGGCUGC | 407 | AGUAUGAUGGAAAUACUCCAAG | 451 |
| S407-AS451-M4 | UGGAGUAUUUCCAUCAUACUGCAGCCGAAAGGCUGC | 407 | AGUAUGAUGGAAAUACUCCAAG | 451 |
| S407-AS451-M5 | UGGAGUAUUUCCAUCAUACUGCAGCCGAAAGGCUGC | 407 | AGUAUGAUGGAAAUACUCCAAG | 451 |
| S407-AS452-M6 | UGGAGUAUUUCCAUCAUACUGCAGCCGAAAGGCUGC | 407 | AGUAUGAUGGAAAUACTCCAAG | 452 |
| S407-AS451-M7 | UGGAGUAUUUCCAUCAUACUGCAGCCGAAAGGCUGC | 407 | AGUAUGAUGGAAAUACUCCAAG | 451 |

TABLE 4-continued

GYS2 RNAi oligonucleotides

| App Name | Sense Sequence | S SEQ ID NO | Antisense Sequence | AS SEQ ID NO |
|---|---|---|---|---|
| S407-AS451-M8 | UGGAGUAUUUCCAUCAUACUGCAGCCGAAAGGCUGC | 407 | AGUAUGAUGGAAAUACUCCAAG | 451 |
| S407-AS451-M9 | UGGAGUAUUUCCAUCAUACUGCAGCCGAAAGGCUGC | 407 | AGUAUGAUGGAAAUACUCCAAG | 451 |
| S407-AS451-M10 | UGGAGUAUUUCCAUCAUACUGCAGCCGAAAGGCUGC | 407 | AGUAUGAUGGAAAUACUCCAAG | 451 |
| S407-AS451-M11 | UGGAGUAUUUCCAUCAUACUGCAGCCGAAAGGCUGC | 407 | AGUAUGAUGGAAAUACUCCAAG | 451 |
| S408-AS453-M12 | UGGAGUAUUUCCAUCAUACGCAGCCGAAAGGCUGC | 408 | GTAUGAUGGAAAUACTCCAAG | 453 |
| S408-AS454-M13 | UGGAGUAUUUCCAUCAUACGCAGCCGAAAGGCUGC | 408 | GUAUGAUGGAAAUACUCCAAG | 454 |
| S409-AS455-M2 | GAGUAUUUCCAUCAUACUAUGCAGCCGAAAGGCUGC | 409 | AUAGUAUGAUGGAAAUACUCCA | 455 |
| S409-AS455-M3 | GAGUAUUUCCAUCAUACUAUGCAGCCGAAAGGCUGC | 409 | AUAGUAUGAUGGAAAUACUCCA | 455 |
| S409-AS455-M4 | GAGUAUUUCCAUCAUACUAUGCAGCCGAAAGGCUGC | 409 | AUAGUAUGAUGGAAAUACUCCA | 455 |
| S409-AS455-M5 | GAGUAUUUCCAUCAUACUAUGCAGCCGAAAGGCUGC | 409 | AUAGUAUGAUGGAAAUACUCCA | 455 |
| S409-AS456-M6 | GAGUAUUUCCAUCAUACUAUGCAGCCGAAAGGCUGC | 409 | ATAGUAUGAUGGAAAUACTCCA | 456 |
| S409-AS455-M7 | GAGUAUUUCCAUCAUACUAUGCAGCCGAAAGGCUGC | 409 | AUAGUAUGAUGGAAAUACUCCA | 455 |
| S409-AS455-M8 | GAGUAUUUCCAUCAUACUAUGCAGCCGAAAGGCUGC | 409 | AUAGUAUGAUGGAAAUACUCCA | 455 |
| S409-AS455-M9 | GAGUAUUUCCAUCAUACUAUGCAGCCGAAAGGCUGC | 409 | AUAGUAUGAUGGAAAUACUCCA | 455 |
| S409-AS455-M10 | GAGUAUUUCCAUCAUACUAUGCAGCCGAAAGGCUGC | 409 | AUAGUAUGAUGGAAAUACUCCA | 455 |
| S409-AS455-M11 | GAGUAUUUCCAUCAUACUAUGCAGCCGAAAGGCUGC | 409 | AUAGUAUGAUGGAAAUACUCCA | 455 |
| S410-AS457-M12 | GAGUAUUUCCAUCAUACUAGCAGCCGAAAGGCUGC | 410 | UAGUAUGAUGGAAAUACTCCA | 457 |
| S410-AS458-M13 | GAGUAUUUCCAUCAUACUAGCAGCCGAAAGGCUGC | 410 | UAGUAUGAUGGAAAUACUCCA | 458 |
| S411-AS459-M2 | CCAGCAUGCCAGACACCUGAGCAGCCGAAAGGCUGC | 411 | UCAGGUGUCUGGCAUGCUGGUA | 459 |
| S411-AS459-M3 | CCAGCAUGCCAGACACCUGAGCAGCCGAAAGGCUGC | 411 | UCAGGUGUCUGGCAUGCUGGUA | 459 |
| S411-AS459-M4 | CCAGCAUGCCAGACACCUGAGCAGCCGAAAGGCUGC | 411 | UCAGGUGUCUGGCAUGCUGGUA | 459 |
| S411-AS459-M5 | CCAGCAUGCCAGACACCUGAGCAGCCGAAAGGCUGC | 411 | UCAGGUGUCUGGCAUGCUGGUA | 459 |
| S411-AS459-M6 | CCAGCAUGCCAGACACCUGAGCAGCCGAAAGGCUGC | 411 | UCAGGUGUCUGGCAUGCUGGUA | 459 |
| S411-AS459-M7 | CCAGCAUGCCAGACACCUGAGCAGCCGAAAGGCUGC | 411 | UCAGGUGUCUGGCAUGCUGGUA | 459 |
| S411-AS459-M8 | CCAGCAUGCCAGACACCUGAGCAGCCGAAAGGCUGC | 411 | UCAGGUGUCUGGCAUGCUGGUA | 459 |
| S411-AS459-M9 | CCAGCAUGCCAGACACCUGAGCAGCCGAAAGGCUGC | 411 | UCAGGUGUCUGGCAUGCUGGUA | 459 |
| S411-AS459-M10 | CCAGCAUGCCAGACACCUGAGCAGCCGAAAGGCUGC | 411 | UCAGGUGUCUGGCAUGCUGGUA | 459 |
| S411-AS459-M11 | CCAGCAUGCCAGACACCUGAGCAGCCGAAAGGCUGC | 411 | UCAGGUGUCUGGCAUGCUGGUA | 459 |
| S412-AS460-M12 | CCAGCAUGCCAGACACCUGGCAGCCGAAAGGCUGC | 412 | CAGGUGUCUGGCAUGCUGGUA | 460 |
| S412-AS460-M13 | CCAGCAUGCCAGACACCUGGCAGCCGAAAGGCUGC | 412 | CAGGUGUCUGGCAUGCUGGUA | 460 |
| S413-AS461-M2 | AGAAAAAGCUGCAUGGUGAAGCAGCCGAAAGGCUGC | 413 | UUCACCAUGCAGCUUUUUCUUC | 461 |
| S413-AS461-M3 | AGAAAAAGCUGCAUGGUGAAGCAGCCGAAAGGCUGC | 413 | UUCACCAUGCAGCUUUUUCUUC | 461 |
| S413-AS461-M4 | AGAAAAAGCUGCAUGGUGAAGCAGCCGAAAGGCUGC | 413 | UUCACCAUGCAGCUUUUUCUUC | 461 |
| S413-AS461-M5 | AGAAAAAGCUGCAUGGUGAAGCAGCCGAAAGGCUGC | 413 | UUCACCAUGCAGCUUUUUCUUC | 461 |
| S413-AS462-M6 | AGAAAAAGCUGCAUGGUGAAGCAGCCGAAAGGCUGC | 413 | UTCACCAUGCAGCUUUTUCUUC | 462 |
| S413-AS461-M7 | AGAAAAAGCUGCAUGGUGAAGCAGCCGAAAGGCUGC | 413 | UUCACCAUGCAGCUUUUUCUUC | 461 |
| S413-AS461-M8 | AGAAAAAGCUGCAUGGUGAAGCAGCCGAAAGGCUGC | 413 | UUCACCAUGCAGCUUUUUCUUC | 461 |
| S413- | AGAAAAAGCUGCAUGGUGAAGCAGCC | 413 | UUCACCAUGCAGCUUUUU | 461 |

TABLE 4-continued

GYS2 RNAi oligonucleotides

| App Name | Sense Sequence | S SEQ ID NO | Antisense Sequence | AS SEQ ID NO |
|---|---|---|---|---|
| AS461-M9 | GAAAGGCUGC | | CUUC | |
| S413-AS461-M10 | AGAAAAAGCUGCAUGGUGAAGCAGCCGAAAGGCUGC | 413 | UUCACCAUGCAGCUUUUUCUUC | 461 |
| S413-AS461-M11 | AGAAAAAGCUGCAUGGUGAAGCAGCCGAAAGGCUGC | 413 | UUCACCAUGCAGCUUUUUCUUC | 461 |
| S414-AS463-M12 | AGAAAAAGCUGCAUGGUGAGCAGCCGAAAGGCUGC | 414 | UCACCAUGCAGCUUUTUCUUC | 463 |
| S414-AS464-M13 | AGAAAAAGCUGCAUGGUGAGCAGCCGAAAGGCUGC | 414 | UCACCAUGCAGCUUUUUCUUC | 464 |
| S415-AS465-M2 | UGGUGAAUAUAAGAACUGAAGCAGCCGAAAGGCUGC | 415 | UUCAGUUCUUAUAUUCACCAUG | 465 |
| S415-AS465-M3 | UGGUGAAUAUAAGAACUGAAGCAGCCGAAAGGCUGC | 415 | UUCAGUUCUUAUAUUCACCAUG | 465 |
| S415-AS465-M4 | UGGUGAAUAUAAGAACUGAAGCAGCCGAAAGGCUGC | 415 | UUCAGUUCUUAUAUUCACCAUG | 465 |
| S415-AS465-M5 | UGGUGAAUAUAAGAACUGAAGCAGCCGAAAGGCUGC | 415 | UUCAGUUCUUAUAUUCACCAUG | 465 |
| S415-AS598-M6 | UGGUGAAUAUAAGAACUGAAGCAGCCGAAAGGCUGC | 415 | UTCAGUUCUUAUAUUCACCAUG | 598 |
| S415-AS465-M7 | UGGUGAAUAUAAGAACUGAAGCAGCCGAAAGGCUGC | 415 | UUCAGUUCUUAUAUUCACCAUG | 465 |
| S415-AS465-M8 | UGGUGAAUAUAAGAACUGAAGCAGCCGAAAGGCUGC | 415 | UUCAGUUCUUAUAUUCACCAUG | 465 |
| S415-AS465-M9 | UGGUGAAUAUAAGAACUGAAGCAGCCGAAAGGCUGC | 415 | UUCAGUUCUUAUAUUCACCAUG | 465 |
| S415-AS465-M10 | UGGUGAAUAUAAGAACUGAAGCAGCCGAAAGGCUGC | 415 | UUCAGUUCUUAUAUUCACCAUG | 465 |
| S415-AS465-M11 | UGGUGAAUAUAAGAACUGAAGCAGCCGAAAGGCUGC | 415 | UUCAGUUCUUAUAUUCACCAUG | 465 |
| S416-AS466-M12 | UGGUGAAUAUAAGAACUGAGCAGCCGAAAGGCUGC | 416 | UCAGUUCUUAUAUUCACCAUG | 466 |
| S416-AS466-M13 | UGGUGAAUAUAAGAACUGAGCAGCCGAAAGGCUGC | 416 | UCAGUUCUUAUAUUCACCAUG | 466 |
| S467-AS518-M1 | GGAGGCAUCUAUACUGUGAUUCAGA | 467 | UCUGAAUCACAGUAUAGAUGCCUCCAA | 518 |
| S468-AS519-M1 | GGCAUCUAUACUGUGAUUCAGACAA | 468 | UUGUCUGAAUCACAGUAUAGAUGCCUC | 519 |
| S469-AS520-M1 | GCAUCUAUACUGUGAUUCAGACAAA | 469 | UUUGUCUGAAUCACAGUAUAGAUGCCU | 520 |
| S470-AS521-M1 | GUCCAUAUUUUGAGCAUAAUAUGAA | 470 | UUCAUAUUAUGCUCAAAAUAUGGACCU | 521 |
| S471-AS522-M1 | AUAUUUUGAGCAUAAUAUGAAGACT | 471 | AGUCUUCAUAUUAUGCUCAAAAUAUGG | 522 |
| S52-AS244-M1 | GCAGCAAAUAUUGAUUUCUACAACC | 52 | GGUUGUAGAAAUCAAUAUUUGCUGCAC | 244 |
| S55-AS247-M1 | GCAAAUAUUGAUUUCUACAACCAUC | 55 | GAUGGUUGUAGAAAUCAAUAUUUGCUG | 247 |
| S75-AS267-M1 | GGUUUCUGAAAUAACAGCAAUAGAA | 75 | UUCUAUUGCUGUUAUUUCAGAAACCGU | 267 |
| S77-AS269-M1 | CUGAAAUAACAGCAAUAGAAGCUGA | 77 | UCAGCUUCUAUUGCUGUUAUUUCAGAA | 269 |
| S472-AS523-M1 | ACGGCUUGAAUGUUAAGAAAUUUTC | 472 | GAAAAUUUCUUAACAUUCAAGCCGUUU | 523 |
| S473-AS524-M1 | CGGCUUGAAUGUUAAGAAAUUUUCA | 473 | UGAAAAUUUCUUAACAUUCAAGCCGUU | 524 |
| S80-AS272-M1 | GGCUUGAAUGUUAAGAAAUUUUCAG | 80 | CUGAAAAUUUCUUAACAUUCAAGCCGU | 272 |
| S81-AS273-M1 | GCUUGAAUGUUAAGAAAUUUUCAGC | 81 | GCUGAAAAUUUCUUAACAUUCAAGCCG | 273 |
| S82-AS274-M1 | CUUGAAUGUUAAGAAAUUUUCAGCA | 82 | UGCUGAAAAUUUCUUAACAUUCAAGCC | 274 |
| S83-AS275-M1 | UUGAAUGUUAAGAAAUUUUCAGCAG | 83 | CUGCUGAAAAUUUCUUAACAUUCAAGC | 275 |
| S84-AS276-M1 | UGAAUGUUAAGAAAUUUUCAGCAGT | 84 | ACUGCUGAAAAUUUCUUAACAUUCAAG | 276 |
| S85-AS277-M1 | GAAUGUUAAGAAAUUUUCAGCAGTG | 85 | CACUGCUGAAAAUUUCUUAACAUUCAA | 277 |
| S474-AS525-M1 | AAUGUUAAGAAAUUUUCAGCAGUGC | 474 | GCACUGCUGAAAAUUUCUUAACAUUCA | 525 |
| S86-AS278-M1 | AUGUUAAGAAAUUUUCAGCAGUGCA | 86 | UGCACUGCUGAAAAUUUCUUAACAUUC | 278 |
| S475-AS526-M1 | UGUUAAGAAAUUUUCAGCAGUGCAT | 475 | AUGCACUGCUGAAAAUUUCUUAACAUU | 526 |
| S476-AS527-M1 | GUUAAGAAAUUUUCAGCAGUGCATG | 476 | CAUGCACUGCUGAAAAUUUCUUAACAU | 527 |

TABLE 4-continued

GYS2 RNAi oligonucleotides

| App Name | Sense Sequence | S SEQ ID NO | Antisense Sequence | AS SEQ ID NO |
|---|---|---|---|---|
| S143-AS335-M1 | GGAGUAUUUCCAUCAUACUAUGAAC | 143 | GUUCAUAGUAUGAUGGAAAUACUCCAA | 335 |
| S181-AS373-M1 | GCUGCAUGGUGAAUAUAAGAACUGA | 181 | UCAGUUCUUAUAUUCACCAUGCAGCUU | 373 |
| S182-AS374-M1 | CUGCAUGGUGAAUAUAAGAACUGAA | 182 | UUCAGUUCUUAUAUUCACCAUGCAGCU | 374 |
| S477-AS528-M1 | UGCAUGGUGAAUAUAAGAACUGAAT | 477 | AUUCAGUUCUUAUAUUCACCAUGCAGC | 528 |
| S183-AS375-M1 | GCAUGGUGAAUAUAAGAACUGAATT | 183 | AAUUCAGUUCUUAUAUUCACCAUGCAG | 375 |
| S184-AS376-M1 | CAUGGUGAAUAUAAGAACUGAAUTC | 184 | GAAUUCAGUUCUUAUAUUCACCAUGCA | 376 |
| S185-AS377-M1 | AUGGUGAAUAUAAGAACUGAAUUCT | 185 | AGAAUUCAGUUCUUAUAUUCACCAUGC | 377 |
| S186-AS378-M1 | UGGUGAAUAUAAGAACUGAAUUCTA | 186 | UAGAAUUCAGUUCUUAUAUUCACCAUG | 378 |
| S187-AS379-M1 | GGUGAAUAUAAGAACUGAAUUCUAC | 187 | GUAGAAUUCAGUUCUUAUAUUCACCAU | 379 |
| S188-AS380-M1 | GUGAAUAUAAGAACUGAAUUCUACA | 188 | UGUAGAAUUCAGUUCUUAUAUUCACCA | 380 |
| S478-AS529-M1 | UGAAUAUAAGAACUGAAUUCUACAT | 478 | AUGUAGAAUUCAGUUCUUAUAUUCACC | 529 |
| S479-AS530-M1 | GAAUAUAAGAACUGAAUUCUACATG | 479 | CAUGUAGAAUUCAGUUCUUAUAUUCAC | 530 |
| S189-AS381-M1 | AAUAUAAGAACUGAAUUCUACAUGT | 189 | ACAUGUAGAAUUCAGUUCUUAUAUUCA | 381 |
| S480-AS531-M1 | CAAAGUAAGACUAAUUAUUUAAAAT | 480 | AUUUUAAAUAAUUAGUCUUACUUUGCU | 531 |
| S481-AS532-M1 | AAAGUAAGACUAAUUAUUUAAAATA | 481 | UAUUUUAAAUAAUUAGUCUUACUUUGC | 532 |
| S482-AS533-M1 | AGAAAUUGAGUGAAUGACAAUUUTG | 482 | CAAAAUUGUCAUUCACUCAAUUUCUUC | 533 |
| S483-AS534-M1 | AAAUUGAGUGAAUGACAAUUUUGTA | 483 | UACAAAAUUGUCAUUCACUCAAUUUCU | 534 |
| S484-AS535-M1 | AUUGAGUGAAUGACAAUUUUGUAAT | 484 | AUUACAAAAUUGUCAUUCACUCAAUUU | 535 |
| S485-AS536-M1 | AAUGACAAUUUUGUAAUUUAGGATA | 485 | UAUCCUAAAUUACAAAAUUGUCAUUCA | 536 |
| S486-AS537-M1 | AAGUGUUUUUAAAAUGGUGAAUUTA | 486 | UAAAUUCACCAUUUUAAAAACACUUUU | 537 |
| S487-AS538-M1 | AGUGUUUUUAAAAUGGUGAAUUUAA | 487 | UUAAAUUCACCAUUUUAAAAACACUUU | 538 |
| S488-AS539-M1 | CUUACUCUGUUUAUUUUUAAAUGAT | 488 | AUCAUUUAAAAAUAAACAGAGUAAGAG | 539 |
| S489-AS540-M1 | CUCUGUUUAUUUUUAAAUGAUCATC | 489 | GAUGAUCAUUUAAAAAUAAACAGAGUA | 540 |
| S490-AS541-M1 | UCUGUUUAUUUUUAAAUGAUCAUCA | 490 | UGAUGAUCAUUUAAAAAUAAACAGAGU | 541 |
| S491-AS542-M1 | GUUUAUUUUUAAAUGAUCAUCAUAA | 491 | UUAUGAUGAUCAUUUAAAAAUAAACAG | 542 |
| S492-AS543-M1 | AUCAUCAUAAUCCUUUGCUUACUAT | 492 | AUAGUAAGCAAAGGAUUAUGAUGAUCA | 543 |
| S493-AS544-M1 | GUGCACUACCUACAUUUUUUAAATA | 493 | UAUUUAAAAAAUGUAGGUAGUGCACAU | 544 |
| S494-AS545-M1 | GCUAGGUUUUUACUGAUUAUUUUCA | 494 | UGAAAAUAAUCAGUAAAAACCUAGCUA | 545 |
| S495-AS546-M1 | CUAGGUUUUUACUGAUUAUUUUCAT | 495 | AUGAAAAUAAUCAGUAAAAACCUAGCU | 546 |
| S496-AS547-M1 | AGGUUUUUACUGAUUAUUUUCAUTT | 496 | AAAUGAAAAUAAUCAGUAAAAACCUAG | 547 |
| S497-AS548-M1 | CUGAUUAUUUUCAUUUUUCACAUGC | 497 | GCAUGUGAAAAAUGAAAAUAAUCAGUA | 548 |
| S498-AS549-M1 | AUGGACAUUUAUGUCACUUUUGAAA | 498 | UUUCAAAAGUGACAUAAAUGUCCAUUA | 549 |
| S499-AS550-M1 | GACAUUUAUGUCACUUUUGAAAUCT | 499 | AGAUUUCAAAAGUGACAUAAAUGUCCA | 550 |
| S500-AS551-M1 | ACAUUUAUGUCACUUUUGAAAUCTA | 500 | UAGAUUUCAAAAGUGACAUAAAUGUCC | 551 |
| S501-AS552-M1 | UAGAAUUGAUGUUGUAAUUAAUGCA | 501 | UGCAUUAAUUACAACAUCAAUUCUAGA | 552 |
| S502-AS553-M1 | AGAAUUGAUGUUGUAAUUAAUGCAA | 502 | UUGCAUUAAUUACAACAUCAAUUCUAG | 553 |
| S503-AS554-M1 | GAAUUGAUGUUGUAAUUAAUGCAAG | 503 | CUUGCAUUAAUUACAACAUCAAUUCUA | 554 |
| S504- | ACCAUCUUACUGUAACAUUUUUCTA | 504 | UAGAAAAAUGUUACAGUA | 555 |

TABLE 4-continued

GYS2 RNAi oligonucleotides

| App Name | Sense Sequence | S SEQ ID NO | Antisense Sequence | AS SEQ ID NO |
|---|---|---|---|---|
| AS555-M1 | | | AGAUGGUGG | |
| S505-AS556-M1 | CAUCUUACUGUAACAUUUUUCUATT | 505 | AAUAGAAAAAUGUUACAGUAAGAUGGU | 556 |
| S506-AS557-M1 | UCUUACUGUAACAUUUUUCUAUUGT | 506 | ACAAUAGAAAAAUGUUACAGUAAGAUG | 557 |
| S507-AS558-M1 | CUUACUGUAACAUUUUUCUAUUGTT | 507 | AACAAUAGAAAAAUGUUACAGUAAGAU | 558 |
| S508-AS559-M1 | UUACUGUAACAUUUUUCUAUUGUTT | 508 | AAACAAUAGAAAAAUGUUACAGUAAGA | 559 |
| S509-AS560-M1 | ACUGUAACAUUUUUCUAUUGUUUAA | 509 | UUAAACAAUAGAAAAAUGUUACAGUAA | 560 |
| S510-AS561-M1 | CUGUAACAUUUUUCUAUUGUUUAAA | 510 | UUUAAACAAUAGAAAAAUGUUACAGUA | 561 |
| S511-AS562-M1 | UGUAACAUUUUUCUAUUGUUUAAAT | 511 | AUUUAAACAAUAGAAAAAUGUUACAGU | 562 |
| S512-AS563-M1 | GUAACAUUUUUCUAUUGUUUAAATA | 512 | UAUUUAAACAAUAGAAAAAUGUUACAG | 563 |
| S513-AS564-M1 | UAACAUUUUUCUAUUGUUUAAAUAG | 513 | CUAUUUAAACAAUAGAAAAAUGUUACA | 564 |
| S514-AS565-M1 | AACAUUUUUCUAUUGUUUAAAUAGA | 514 | UCUAUUUAAACAAUAGAAAAAUGUUAC | 565 |
| S515-AS566-M1 | ACAUUUUUCUAUUGUUUAAAUAGAA | 515 | UUCUAUUUAAACAAUAGAAAAAUGUUA | 566 |
| S516-AS567-M1 | CAUUUUUCUAUUGUUUAAAUAGAAA | 516 | UUUCUAUUUAAACAAUAGAAAAAUGUU | 567 |
| S517-AS568-M1 | GUCAAUCUUCAUAGAUGAUAACUTG | 517 | CAAGUUAUCAUCUAUGAAGAUUGACCA | 568 |
| S569-AS575-M14 | GGCAUCUAUACUGUGAUUCAGCAGCCGAAAGGCUGC | 569 | UGAAUCACAGUAUAGAUGCCGG | 575 |
| S569-AS575-M15 | GGCAUCUAUACUGUGAUUCAGCAGCCGAAAGGCUGC | 569 | UGAAUCACAGUAUAGAUGCCGG | 575 |
| S570-AS576-M14 | GCAUCUAUACUGUGAUUCAGGCAGCCGAAAGGCUGC | 570 | CUGAAUCACAGUAUAGAUGCGG | 576 |
| S570-AS576-M15 | GCAUCUAUACUGUGAUUCAGGCAGCCGAAAGGCUGC | 570 | CUGAAUCACAGUAUAGAUGCGG | 576 |
| S571-AS577-M14 | GCAGCAAAUAUUGAUUUCUAGCAGCCGAAAGGCUGC | 571 | UAGAAAUCAAUAUUUGCUGCGG | 577 |
| S571-AS577-M15 | GCAGCAAAUAUUGAUUUCUAGCAGCCGAAAGGCUGC | 571 | UAGAAAUCAAUAUUUGCUGCGG | 577 |
| S572-AS578-M15 | CUGAAAUAACAGCAAUAGAAGCAGCCGAAAGGCUGC | 572 | UUCUAUUGCUGUUAUUUCAGGG | 578 |
| S573-AS579-M15 | ACGGCUUGAAUGUUAAGAAAGCAGCCGAAAGGCUGC | 573 | UUUCUUAACAUUCAAGCCGUGG | 579 |
| S574-AS580-M14 | AGUGUUUUUAAAAUGGUGAAGCAGCCGAAAGGCUGC | 574 | UUCACCAUUUUAAAAACACUGG | 580 |
| S574-AS580-M15 | AGUGUUUUUAAAAUGGUGAAGCAGCCGAAAGGCUGC | 574 | UUCACCAUUUUAAAAACACUGG | 580 |
| S385-AS417-M16 | AGGUGCAUUUUGGAAGAUGGGCAGCCGAAAGGCUGC | 385 | CCAUCUUCCAAAAUGCACCUGG | 417 |
| S389-AS421-M17 | AAGGAAGUCCUUAUGUGGUAGCAGCCGAAAGGCUGC | 389 | UACCACAUAAGGACUUCCUUCU | 421 |
| S391-AS425-M16 | AUGAUAUGCUGAUAUUUGGAGCAGCCGAAAGGCUGC | 391 | UCCAAAUAUCAGCAUAUCAUUG | 425 |
| S393-AS429-M16 | AGCAAAUAUUGAUUUCUACAGCAGCCGAAAGGCUGC | 393 | UGUAGAAAUCAAUAUUUGCUGC | 429 |
| S397-AS436-M16 | CUUGAAUGUUAAGAAAUUUUGCAGCCGAAAGGCUGC | 397 | AAAAUUUCUUAACAUUCAAGCC | 436 |
| S397-AS586-M18 | CUUGAAUGUUAAGAAAUUUAGCAGCCGAAAGGCUGC | 397 | UAAAUUUCUUAACAUUCAAGGG | 586 |
| S397-AS587-M19 | CUUGAAUGUUAAGAAAUUUUGCAGCCGAAAGGCUGC | 397 | AAAUUUCUUAACAUUCAAGGG | 587 |
| S395-AS433-M17 | CCACGGUUUCUGAAAUAACAGCAGCCGAAAGGCUGC | 395 | UGUUAUUUCAGAAACCGUGGUG | 433 |
| S399-AS438-M16 | UGAAUGUUAAGAAAUUUUCAGCAGCCGAAAGGCUGC | 399 | UGAAAAUUUCUUAACAUUCAAG | 438 |
| S401-AS442-M17 | CGAGGUCAUUUCUAUGGUCAGCAGCCGAAAGGCUGC | 401 | UGACCAUAGAAAUGACCUCGAA | 442 |
| S405-AS448-M17 | CUUGGAGUAUUUCCAUCAUAGCAGCCGAAAGGCUGC | 405 | UAUGAUGGAAAUACUCCAAGAU | 448 |
| S413-AS461-M17 | AGAAAAAGCUGCAUGGUGAAGCAGCCGAAAGGCUGC | 413 | UUCACCAUGCAGCUUUUUCUUC | 461 |
| S413-AS588-M20 | AGAAAAAGCUGCAUGGUGAAGCAGCCGAAAGGCUGC | 413 | UUCACCAUGCAGCUUUUUCUGG | 588 |
| S413-AS589-M21 | AGAAAAAGCUGCAUGGUGAAGCAGCCGAAAGGCUGC | 413 | UCACCAUGCAGCUUUUUCUGG | 589 |

TABLE 4-continued

GYS2 RNAi oligonucleotides

| App Name | Sense Sequence | S SEQ ID NO | Antisense Sequence | AS SEQ ID NO |
|---|---|---|---|---|
| S413-AS461-M22 | AGAAAAAGCUGCAUGGUGAAGCAGCCGAAAGGCUGC | 413 | UUCACCAUGCAGCUUUUUCUUC | 461 |
| S415-AS465-M16 | UGGUGAAUAUAAGAACUGAAGCAGCCGAAAGGCUGC | 415 | UUCAGUUCUUAUAUUCACCAUG | 465 |
| S393-AS589-M18 | AGCAAAUAUUGAUUUCUACAGCAGCCGAAAGGCUGC | 393 | UGUAGAAAUCAAUAUUUGCUGG | 589 |
| S397-AS586-M23 | CUUGAAUGUUAAGAAAUUUAGCAGCCGAAAGGCUGC | 397 | UAAAUUUCUUAACAUUCAAGGG | 586 |
| S399-AS590-M18 | UGAAUGUUAAGAAAUUUUCAGCAGCCGAAAGGCUGC | 399 | UGAAAAUUUCUUAACAUUCAGG | 590 |
| S413-AS588-M20 | AGAAAAAGCUGCAUGGUGAAGCAGCCGAAAGGCUGC | 413 | UUCACCAUGCAGCUUUUUCUGG | 588 |
| S415-AS591-M18 | UGGUGAAUAUAAGAACUGAAGCAGCCGAAAGGCUGC | 415 | UUCAGUUCUUAUAUUCACCAGG | 591 |
| S415-AS591-M23 | UGGUGAAUAUAAGAACUGAAGCAGCCGAAAGGCUGC | 415 | UUCAGUUCUUAUAUUCACCAGG | 591 |
| S397-AS592-M24 | CUUGAAUGUUAAGAAAUUUUGCAGCCGAAAGGCUGC | 397 | AAAAUUUCUUAACAUUCAAGGG | 592 |
| S397-AS592-M25 | CUUGAAUGUUAAGAAAUUUUGCAGCCGAAAGGCUGC | 397 | AAAAUUUCUUAACAUUCAAGGG | 592 |
| S397-AS592-M26 | CUUGAAUGUUAAGAAAUUUUGCAGCCGAAAGGCUGC | 397 | AAAAUUUCUUAACAUUCAAGGG | 592 |
| S397-AS592-M27 | CUUGAAUGUUAAGAAAUUUUGCAGCCGAAAGGCUGC | 397 | AAAAUUUCUUAACAUUCAAGGG | 592 |
| S399-AS590-M24 | UGAAUGUUAAGAAAUUUUCAGCAGCCGAAAGGCUGC | 399 | UGAAAAUUUCUUAACAUUCAGG | 590 |
| S399-AS590-M25 | UGAAUGUUAAGAAAUUUUCAGCAGCCGAAAGGCUGC | 399 | UGAAAAUUUCUUAACAUUCAGG | 590 |
| S399-AS590-M26 | UGAAUGUUAAGAAAUUUUCAGCAGCCGAAAGGCUGC | 399 | UGAAAAUUUCUUAACAUUCAGG | 590 |
| S399-AS590-M27 | UGAAUGUUAAGAAAUUUUCAGCAGCCGAAAGGCUGC | 399 | UGAAAAUUUCUUAACAUUCAGG | 590 |
| S415-AS591-M28 | UGGUGAAUAUAAGAACUGAAGCAGCCGAAAGGCUGC | 415 | UUCAGUUCUUAUAUUCACCAGG | 591 |
| S415-AS591-M29 | UGGUGAAUAUAAGAACUGAAGCAGCCGAAAGGCUGC | 415 | UUCAGUUCUUAUAUUCACCAGG | 591 |
| S415-AS591-M30 | UGGUGAAUAUAAGAACUGAAGCAGCCGAAAGGCUGC | 415 | UUCAGUUCUUAUAUUCACCAGG | 591 |
| S415-AS591-M31 | UGGUGAAUAUAAGAACUGAAGCAGCCGAAAGGCUGC | 415 | UUCAGUUCUUAUAUUCACCAGG | 591 |
| S397-AS592-M32 | CUUGAAUGUUAAGAAAUUUUGCAGCCGAAAGGCUGC | 397 | AAAAUUUCUUAACAUUCAAGGG | 592 |
| S399-AS590-M32 | UGAAUGUUAAGAAAUUUUCAGCAGCCGAAAGGCUGC | 399 | UGAAAAUUUCUUAACAUUCAGG | 590 |
| S415-AS591-M33 | UGGUGAAUAUAAGAACUGAAGCAGCCGAAAGGCUGC | 415 | UUCAGUUCUUAUAUUCACCAGG | 591 |
| S399-AS590-M34 | UGAAUGUUAAGAAAUUUUCAGCAGCCGAAAGGCUGC | 399 | UGAAAAUUUCUUAACAUUCAGG | 590 |
| S399-AS590-M35 | UGAAUGUUAAGAAAUUUUCAGCAGCCGAAAGGCUGC | 399 | UGAAAAUUUCUUAACAUUCAGG | 590 |
| S399-AS590-M28 | UGAAUGUUAAGAAAUUUUCAGCAGCCGAAAGGCUGC | 399 | UGAAAAUUUCUUAACAUUCAGG | 590 |
| S399-AS590-M36 | UGAAUGUUAAGAAAUUUUCAGCAGCCGAAAGGCUGC | 399 | UGAAAAUUUCUUAACAUUCAGG | 590 |
| S581-AS593-M37 | GAAUGUUAAGAAAUUUUCAGCAGCCGAAAGGCUGC | 581 | UGAAAAUUUCUUAACAUUCGG | 593 |
| S399-AS590-M38 | UGAAUGUUAAGAAAUUUUCAGCAGCCGAAAGGCUGC | 399 | UGAAAAUUUCUUAACAUUCAGG | 590 |
| S399-AS590-M39 | UGAAUGUUAAGAAAUUUUCAGCAGCCGAAAGGCUGC | 399 | UGAAAAUUUCUUAACAUUCAGG | 590 |
| S399-AS590-M40 | UGAAUGUUAAGAAAUUUUCAGCAGCCGAAAGGCUGC | 399 | UGAAAAUUUCUUAACAUUCAGG | 590 |
| S399-AS590-M41 | UGAAUGUUAAGAAAUUUUCAGCAGCCGAAAGGCUGC | 399 | UGAAAAUUUCUUAACAUUCAGG | 590 |
| S399-AS590-M42 | UGAAUGUUAAGAAAUUUUCAGCAGCCGAAAGGCUGC | 399 | UGAAAAUUUCUUAACAUUCAGG | 590 |
| S399-AS590-M43 | UGAAUGUUAAGAAAUUUUCAGCAGCCGAAAGGCUGC | 399 | UGAAAAUUUCUUAACAUUCAGG | 590 |
| S399-AS590-M24 | UGAAUGUUAAGAAAUUUUCAGCAGCCGAAAGGCUGC | 399 | UGAAAAUUUCUUAACAUUCAGG | 590 |
| S399-AS590-M44 | UGAAUGUUAAGAAAUUUUCAGCAGCCGAAAGGCUGC | 399 | UGAAAAUUUCUUAACAUUCAGG | 590 |
| S399-AS590-M28 | UGAAUGUUAAGAAAUUUUCAGCAGCCGAAAGGCUGC | 399 | UGAAAAUUUCUUAACAUUCAGG | 590 |
| S399- | UGAAUGUUAAGAAAUUUUCAGCAGCC | 399 | UGAAAAUUUCUUAACAUU | 590 |

TABLE 4-continued

| GYS2 RNAi oligonucleotides | | | | |
|---|---|---|---|---|
| App Name | Sense Sequence | S SEQ ID NO | Antisense Sequence | AS SEQ ID NO |
| AS590-M45 | GAAAGGCUGC | | CAGG | |
| S399-AS590-M40 | UGAAUGUUAAGAAAUUUUCAGCAGCCGAAAGGCUGC | 399 | UGAAAAUUUCUUAACAUUCAGG | 590 |
| S399-AS590-M46 | UGAAUGUUAAGAAAUUUUCAGCAGCCGAAAGGCUGC | 399 | UGAAAAUUUCUUAACAUUCAGG | 590 |
| S399-AS590-M38 | UGAAUGUUAAGAAAUUUUCAGCAGCCGAAAGGCUGC | 399 | UGAAAAUUUCUUAACAUUCAGG | 590 |
| S399-AS590-M46 | UGAAUGUUAAGAAAUUUUCAGCAGCCGAAAGGCUGC | 399 | UGAAAAUUUCUUAACAUUCAGG | 590 |
| S571-AS577-M47 | GCAGCAAAUAUUGAUUUCUAGCAGCCGAAAGGCUGC | 571 | UAGAAAUCAAUAUUUGCUGCGG | 577 |
| S573-AS579-M47 | ACGGCUUGAAUGUUAAGAAAGCAGCCGAAAGGCUGC | 573 | UUUCUUAACAUUCAAGCCGUGG | 579 |
| S582-AS594-M47 | UGCAUGAGUUUCAAAAUCUAGCAGCCGAAAGGCUGC | 582 | UAGAUUUUGAAACUCAUGCAGG | 594 |
| S583-AS595-M47 | UCGAGAUGAUCUAACAAUUAGCAGCCGAAAGGCUGC | 583 | UAAUUGUUAGAUCAUCUCGAGG | 595 |
| S584-AS596-M47 | AGACUAAUUAUUUAAAAUAAGCAGCCGAAAGGCUGC | 584 | UUAUUUUAAAUAAUUAGUCUGG | 596 |
| S574-AS580-M47 | AGUGUUUUUAAAAUGGUGAAGCAGCCGAAAGGCUGC | 574 | UUCACCAUUUUAAAAACACUGG | 580 |
| S585-AS597-M47 | AGAAUUGAUGUUGUAAUUAAGCAGCCGAAAGGCUGC | 585 | UUAAUUACAACAUCAAUUCUGG | 597 |
| S399-AS590-M48 | UGAAUGUUAAGAAAUUUUCAGCAGCCGAAAGGCUGC | 399 | UGAAAAUUUCUUAACAUUCAGG | 590 |
| S399-AS590-M49 | UGAAUGUUAAGAAAUUUUCAGCAGCCGAAAGGCUGC | 399 | UGAAAAUUUCUUAACAUUCAGG | 590 |
| S399-AS590-M50 | UGAAUGUUAAGAAAUUUUCAGCAGCCGAAAGGCUGC | 399 | UGAAAAUUUCUUAACAUUCAGG | 590 |
| S399-AS590-M51 | UGAAUGUUAAGAAAUUUUCAGCAGCCGAAAGGCUGC | 399 | UGAAAAUUUCUUAACAUUCAGG | 590 |
| S399-AS590-M52 | UGAAUGUUAAGAAAUUUUCAGCAGCCGAAAGGCUGC | 399 | UGAAAAUUUCUUAACAUUCAGG | 590 |
| S399-AS590-M53 | UGAAUGUUAAGAAAUUUUCAGCAGCCGAAAGGCUGC | 399 | UGAAAAUUUCUUAACAUUCAGG | 590 |
| S399-AS590-M54 | UGAAUGUUAAGAAAUUUUCAGCAGCCGAAAGGCUGC | 399 | UGAAAAUUUCUUAACAUUCAGG | 590 |
| S399-AS590-M55 | UGAAUGUUAAGAAAUUUUCAGCAGCCGAAAGGCUGC | 399 | UGAAAAUUUCUUAACAUUCAGG | 590 |
| S573-AS579-M56 | ACGGCUUGAAUGUUAAGAAAGCAGCCGAAAGGCUGC | 573 | UUUCUUAACAUUCAAGCCGUGG | 579 |
| S573-AS579-M57 | ACGGCUUGAAUGUUAAGAAAGCAGCCGAAAGGCUGC | 573 | UUUCUUAACAUUCAAGCCGUGG | 579 |
| S573-AS579-M50 | ACGGCUUGAAUGUUAAGAAAGCAGCCGAAAGGCUGC | 573 | UUUCUUAACAUUCAAGCCGUGG | 579 |
| S573-AS579-M51 | ACGGCUUGAAUGUUAAGAAAGCAGCCGAAAGGCUGC | 573 | UUUCUUAACAUUCAAGCCGUGG | 579 |
| S573-AS579-M52 | ACGGCUUGAAUGUUAAGAAAGCAGCCGAAAGGCUGC | 573 | UUUCUUAACAUUCAAGCCGUGG | 579 |
| S573-AS579-M53 | ACGGCUUGAAUGUUAAGAAAGCAGCCGAAAGGCUGC | 573 | UUUCUUAACAUUCAAGCCGUGG | 579 |
| S573-AS579-M54 | ACGGCUUGAAUGUUAAGAAAGCAGCCGAAAGGCUGC | 573 | UUUCUUAACAUUCAAGCCGUGG | 579 |
| S573-AS579-M55 | ACGGCUUGAAUGUUAAGAAAGCAGCCGAAAGGCUGC | 573 | UUUCUUAACAUUCAAGCCGUGG | 579 |
| S583-AS595-M56 | UCGAGAUGAUCUAACAAUUAGCAGCCGAAAGGCUGC | 583 | UAAUUGUUAGAUCAUCUCGAGG | 595 |
| S583-AS595-M58 | UCGAGAUGAUCUAACAAUUAGCAGCCGAAAGGCUGC | 583 | UAAUUGUUAGAUCAUCUCGAGG | 595 |
| S583-AS595-M50 | UCGAGAUGAUCUAACAAUUAGCAGCCGAAAGGCUGC | 583 | UAAUUGUUAGAUCAUCUCGAGG | 595 |
| S583-AS595-M51 | UCGAGAUGAUCUAACAAUUAGCAGCCGAAAGGCUGC | 583 | UAAUUGUUAGAUCAUCUCGAGG | 595 |
| S583-AS595-M52 | UCGAGAUGAUCUAACAAUUAGCAGCCGAAAGGCUGC | 583 | UAAUUGUUAGAUCAUCUCGAGG | 595 |
| S583-AS595-M53 | UCGAGAUGAUCUAACAAUUAGCAGCCGAAAGGCUGC | 583 | UAAUUGUUAGAUCAUCUCGAGG | 595 |
| S583-AS595-M54 | UCGAGAUGAUCUAACAAUUAGCAGCCGAAAGGCUGC | 583 | UAAUUGUUAGAUCAUCUCGAGG | 595 |
| S583-AS595-M55 | UCGAGAUGAUCUAACAAUUAGCAGCCGAAAGGCUGC | 583 | UAAUUGUUAGAUCAUCUCGAGG | 595 |
| S583-AS595-M59 | UCGAGAUGAUCUAACAAUUAGCAGCCGAAAGGCUGC | 583 | UAAUUGUUAGAUCAUCUCGAGG | 595 |
| S583-AS595-M60 | UCGAGAUGAUCUAACAAUUAGCAGCCGAAAGGCUGC | 583 | UAAUUGUUAGAUCAUCUCGAGG | 595 |

TABLE 4-continued

GYS2 RNAi oligonucleotides

| App Name | Sense Sequence | S SEQ ID NO | Antisense Sequence | AS SEQ ID NO |
|---|---|---|---|---|
| S583-AS595-M61 | UCGAGAUGAUCUAACAAUUAGCAGCCGAAAGGCUGC | 583 | UAAUUGUUAGAUCAUCUCGAGG | 595 |
| S583-AS595-M62 | UCGAGAUGAUCUAACAAUUAGCAGCCGAAAGGCUGC | 583 | UAAUUGUUAGAUCAUCUCGAGG | 599 |
| S583-AS595-M63 | UCGAGAUGAUCUAACAAUUAGCAGCCGAAAGGCUGC | 583 | UAAUUGUUAGAUCAUCUCGAGG | 595 |
| S583-AS595-M64 | UCGAGAUGAUCUAACAAUUAGCAGCCGAAAGGCUGC | 583 | UAAUUGUUAGAUCAUCUCGAGG | 595 |
| S583-AS595-M65 | UCGAGAUGAUCUAACAAUUAGCAGCCGAAAGGCUGC | 583 | UAAUUGUUAGAUCAUCUCGAGG | 595 |
| S583-AS595-M66 | UCGAGAUGAUCUAACAAUUAGCAGCCGAAAGGCUGC | 583 | UAAUUGUUAGAUCAUCUCGAGG | 595 |
| S574-AS580-M56 | AGUGUUUUUAAAAUGGUGAAGCAGCCGAAAGGCUGC | 574 | UUCACCAUUUUAAAAACACUGG | 580 |
| S574-AS580-M58 | AGUGUUUUUAAAAUGGUGAAGCAGCCGAAAGGCUGC | 574 | UUCACCAUUUUAAAAACACUGG | 580 |
| S574-AS580-M50 | AGUGUUUUUAAAAUGGUGAAGCAGCCGAAAGGCUGC | 574 | UUCACCAUUUUAAAAACACUGG | 580 |
| S574-AS580-M51 | AGUGUUUUUAAAAUGGUGAAGCAGCCGAAAGGCUGC | 574 | UUCACCAUUUUAAAAACACUGG | 580 |
| S574-AS580-M52 | AGUGUUUUUAAAAUGGUGAAGCAGCCGAAAGGCUGC | 574 | UUCACCAUUUUAAAAACACUGG | 580 |
| S574-AS580-M53 | AGUGUUUUUAAAAUGGUGAAGCAGCCGAAAGGCUGC | 574 | UUCACCAUUUUAAAAACACUGG | 580 |
| S574-AS580-M54 | AGUGUUUUUAAAAUGGUGAAGCAGCCGAAAGGCUGC | 574 | UUCACCAUUUUAAAAACACUGG | 580 |
| S574-AS580-M55 | AGUGUUUUUAAAAUGGUGAAGCAGCCGAAAGGCUGC | 574 | UUCACCAUUUUAAAAACACUGG | 580 |
| S612-AS620-M5 | UGGGAGGUAUGAGUUUUCAAGCAGCCGAAAGGCUGC | 612 | UUGAAAACUCAUACCUCCCAGG | 620 |
| S613-AS621-M5 | AGGAAAAGUUUGGAAAAAAAGCAGCCGAAAGGCUGC | 613 | UUUUUUUCCAAACUUUUCCUGG | 621 |
| S614-AS622-M5 | UGGUCAAUCUUCAUAGAUGAGCAGCCGAAAGGCUGC | 614 | UCAUCUAUGAAGAUUGACCAGG | 622 |
| S615-AS623-M5 | GGUUUCUGAAAUAACAGCAAGCAGCCGAAAGGCUGC | 615 | UUGCUGUUAUUUCAGAAACCGG | 623 |
| S572-AS578-M5 | CUGAAAUAACAGCAAUAGAAGCAGCCGAAAGGCUGC | 572 | UUCUAUUGCUGUUAUUUCAGGG | 578 |
| S616-AS624-M5 | GUGAAUAUAAGAACUGAAUUGCAGCCGAAAGGCUGC | 616 | AAUUCAGUUCUUAUAUUCACGG | 624 |
| S617-AS625-M5 | AUUGAGUGAAUGACAAUUUUGCAGCCGAAAGGCUGC | 617 | AAAAUUGUCAUUCACUCAAUGG | 625 |
| S618-AS626-M5 | AAUGACAAUUUUGUAAUUUAGCAGCCGAAAGGCUGC | 618 | UAAAUUACAAAAUUGUCAUUGG | 626 |
| S585-AS597-M5 | AGAAUUGAUGUUGUAAUUAAGCAGCCGAAAGGCUGC | 585 | UUAAUUACAACAUCAAUUCUGG | 597 |
| S619-AS627-M5 | GAAUUGAUGUUGUAAUUAAUGCAGCCGAAAGGCUGC | 619 | AUUAAUUACAACAUCAAUUCGG | 627 |
| S573-AS579-M5 | ACGGCUUGAAUGUUAAGAAAGCAGCCGAAAGGCUGC | 573 | UUUCUUAACAUUCAAGCCGUGG | 579 |
| S582-AS594-M5 | UGCAUGAGUUUCAAAAUCUAGCAGCCGAAAGGCUGC | 582 | UAGAUUUUGAAACUCAUGCAGG | 594 |
| S583-AS595-M5 | UCGAGAUGAUCUAACAAUUAGCAGCCGAAAGGCUGC | 583 | UAAUUGUUAGAUCAUCUCGAGG | 595 |
| S584-AS596-M5 | AGACUAAUUAUUUAAAAUAAGCAGCCGAAAGGCUGC | 584 | UUAUUUUAAAUAAUUAGUCUGG | 596 |

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms “a” and “an” and “the” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligonucleotide comprising an antisense strand and a sense strand, wherein the antisense strand comprises a sequence set forth in any one of SEQ ID NOs: 595, 577, 579, 580, 590, 594, 596 and 597, and wherein the sense strand comprises a sequence set forth in any one of SEQ ID NOs: 583, 399, 571, 573, 574, 582, 584 and 585.

2. The oligonucleotide of claim 1, wherein the sense strand and antisense strand sequences are selected from the group consisting of:

a) SEQ ID NO: 583 and SEQ ID NO: 595, respectively;
b) SEQ ID NO: 571 and SEQ ID NO: 577, respectively;
c) SEQ ID NO: 399 and SEQ ID NO: 590, respectively;
d) SEQ ID NO: 573 and SEQ ID NO: 579, respectively;
e) SEQ ID NO: 574 and SEQ ID NO: 580, respectively;
f) SEQ ID NO: 585 and SEQ ID NO: 597, respectively;
g) SEQ ID NO: 582 and SEQ ID NO: 594, respectively; and,
h) SEQ ID NO: 584 and SEQ ID NO: 596, respectively.

3. The oligonucleotide of claim 1, wherein the sense strand comprises SEQ ID NO: 583 and the antisense strand comprises SEQ ID NO: 595.

4. The oligonucleotide of claim 3, wherein the sense strand comprises modified nucleotides and internucleotide linkages, and wherein 1, 2, 3 or 4 nucleotides of GAAA are conjugated to a monovalent GalNAc moiety.

5. The oligonucleotide of claim 3, wherein the 4'-carbon of the sugar of the 5'-nucleotide of the antisense strand comprises a phosphate analog, and wherein the phosphate analog is oxymethylphosphonate, vinylphosphonate, or malonylphosphonate.

6. The oligonucleotide of claim 3, wherein at least one nucleotide of the oligonucleotide is conjugated to one or more targeting ligands, wherein each targeting ligand comprises a N-acetylgalactosamine (GalNAc) moiety.

7. The oligonucleotide of claim 6, wherein the GalNAc moiety is a monovalent GalNAc moiety, a bivalent GalNAc moiety, a trivalent GalNAc moiety, or a tetravalent GalNAc moiety.

8. The oligonucleotide of claim 1, wherein the 4'-carbon of the sugar of the 5'-nucleotide of the antisense strand comprises a phosphate analog, and wherein the phosphate analog is oxymethylphosphonate, vinylphosphonate, or malonylphosphonate.

9. The oligonucleotide of claim 1, wherein at least one nucleotide of the oligonucleotide is conjugated to one or more targeting ligands, wherein each targeting ligand comprises a N-acetylgalactosamine (GalNAc) moiety.

10. The oligonucleotide of claim 9, wherein the GalNAc moiety is a monovalent GalNAc moiety, a bivalent GalNAc moiety, a trivalent GalNAc moiety, or a tetravalent GalNAc moiety.

11. The oligonucleotide of claim 1, wherein the sense strand comprises modified nucleotides and internucleotide linkages, and wherein 1, 2, 3 or 4 nucleotides of GAAA are conjugated to a monovalent GalNAc moiety.

12. A composition comprising the oligonucleotide of claim 1 and an excipient.

13. A composition comprising the oligonucleotide of claim 3 and an excipient.

* * * * *

SEQUENCE LISTING

```
Sequence total quantity: 627
SEQ ID NO: 1            moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 1
caggtgcatt ttggaagatg gctga                                        25

SEQ ID NO: 2            moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 2
aggtgcattt tggaagatgg ctgat                                        25

SEQ ID NO: 3            moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 3
ggtgcatttt ggaagatggc tgata                                        25

SEQ ID NO: 4            moltype = RNA  length = 25
FEATURE                 Location/Qualifiers
misc_feature            1..25
                        note = Synthetic Polynucleotide
source                  1..25
```

```
                        mol_type = other RNA
                        organism = synthetic construct
SEQUENCE: 4
gtgcattttg gaagatggct gatag                                          25

SEQ ID NO: 5            moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 5
tgcattttgg aagatggctg ataga                                          25

SEQ ID NO: 6            moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 6
aaggaagtcc ttatgtggta ctttt                                          25

SEQ ID NO: 7            moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 7
gaagtcctta tgtggtactt tttga                                          25

SEQ ID NO: 8            moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 8
aagtccttat gtggtacttt ttgac                                          25

SEQ ID NO: 9            moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 9
agtccttatg tggtactttt tgaca                                          25

SEQ ID NO: 10           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 10
gtccttatgt ggtacttttt gacat                                          25

SEQ ID NO: 11           moltype = RNA  length = 25
FEATURE                 Location/Qualifiers
misc_feature            1..25
                        note = Synthetic Polynucleotide
source                  1..25
                        mol_type = other RNA
```

-continued

```
                        organism = synthetic construct
SEQUENCE: 11
ccttatgtgg tactttttga catag                                        25

SEQ ID NO: 12           moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 12
gtactttttg acataggcta ttcag                                        25

SEQ ID NO: 13           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 13
cgagaagcca atgatatgct gatat                                        25

SEQ ID NO: 14           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 14
gagaagccaa tgatatgctg atatt                                        25

SEQ ID NO: 15           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 15
agaagccaat gatatgctga tattt                                        25

SEQ ID NO: 16           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 16
gaagccaatg atatgctgat atttg                                        25

SEQ ID NO: 17           moltype = RNA  length = 25
FEATURE                 Location/Qualifiers
misc_feature            1..25
                        note = Synthetic Polynucleotide
source                  1..25
                        mol_type = other RNA
                        organism = synthetic construct
```

```
SEQUENCE: 17
agccaatgat atgctgatat ttgga                                       25

SEQ ID NO: 18          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 18
gccaatgata tgctgatatt tggat                                       25

SEQ ID NO: 19          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 19
ccaatgatat gctgatattt ggatc                                       25

SEQ ID NO: 20          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24..25
                       note = DNA
SEQUENCE: 20
aatgatatgc tgatatttgg atctt                                       25

SEQ ID NO: 21          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24..25
                       note = DNA
SEQUENCE: 21
atgatatgct gatatttgga tcttt                                       25

SEQ ID NO: 22          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 22
tgatatgctg atatttggat cttta                                       25

SEQ ID NO: 23          moltype = RNA  length = 25
FEATURE                Location/Qualifiers
```

-continued

```
misc_feature          1..25
                      note = Synthetic Polynucleotide
source                1..25
                      mol_type = other RNA
                      organism = synthetic construct
SEQUENCE: 23
atatgctgat atttggatct ttaac                                          25

SEQ ID NO: 24         moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..23
                      note = RNA
misc_feature          24
                      note = DNA
misc_feature          25
                      note = RNA
SEQUENCE: 24
atgctgatat ttggatcttt aactg                                          25

SEQ ID NO: 25         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 25
tctttaactg cctggttctt aaaag                                          25

SEQ ID NO: 26         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 26
ctttaactgc ctggttctta aaaga                                          25

SEQ ID NO: 27         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 27
tttaactgcc tggttcttaa aagag                                          25

SEQ ID NO: 28         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 28
ttaactgcct ggttcttaaa agagg                                          25

SEQ ID NO: 29         moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..24
                      note = RNA
misc_feature          25
                      note = DNA
SEQUENCE: 29
taactgcctg gttcttaaaa gaggt                                          25

SEQ ID NO: 30         moltype = RNA  length = 25
```

-continued

```
FEATURE                Location/Qualifiers
misc_feature           1..25
                       note = Synthetic Polynucleotide
source                 1..25
                       mol_type = other RNA
                       organism = synthetic construct
SEQUENCE: 30
ttgcccaatt ccatgaatgg caggc                                        25

SEQ ID NO: 31          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 31
tgcccaattc catgaatggc aggct                                        25

SEQ ID NO: 32          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 32
gcccaattcc atgaatggca ggctg                                        25

SEQ ID NO: 33          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 33
cccaattcca tgaatggcag gctgg                                        25

SEQ ID NO: 34          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 34
ccaattccat gaatggcagg ctgga                                        25

SEQ ID NO: 35          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 35
caattccatg aatggcaggc tggaa                                        25

SEQ ID NO: 36          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
```

```
                        note = DNA
SEQUENCE: 36
aattccatga atggcaggct ggaat                                             25

SEQ ID NO: 37           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 37
attccatgaa tggcaggctg gaatt                                             25

SEQ ID NO: 38           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 38
ttccatgaat ggcaggctgg aattg                                             25

SEQ ID NO: 39           moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 39
tccatgaatg gcaggctgga attgg                                             25

SEQ ID NO: 40           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 40
ggaaacttcc tattgccaca atatt                                             25

SEQ ID NO: 41           moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 41
ggtatctctg tgcagcaaat attga                                             25

SEQ ID NO: 42           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
```

-continued

```
SEQUENCE: 42
gtatctctgt gcagcaaata ttgat                                     25

SEQ ID NO: 43          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24..25
                       note = DNA
SEQUENCE: 43
tatctctgtg cagcaaatat tgatt                                     25

SEQ ID NO: 44          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24..25
                       note = DNA
SEQUENCE: 44
atctctgtgc agcaaatatt gattt                                     25

SEQ ID NO: 45          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 45
tctctgtgca gcaaatattg atttc                                     25

SEQ ID NO: 46          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 46
ctctgtgcag caaatattga tttct                                     25

SEQ ID NO: 47          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 47
tctgtgcagc aaatattgat ttcta                                     25

SEQ ID NO: 48          moltype = RNA  length = 25
FEATURE                Location/Qualifiers
```

```
misc_feature          1..25
                      note = Synthetic Polynucleotide
source                1..25
                      mol_type = other RNA
                      organism = synthetic construct
SEQUENCE: 48
ctgtgcagca aatattgatt tctac                                         25

SEQ ID NO: 49         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 49
tgtgcagcaa atattgattt ctaca                                         25

SEQ ID NO: 50         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 50
gtgcagcaaa tattgatttc tacaa                                         25

SEQ ID NO: 51         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 51
tgcagcaaat attgatttct acaac                                         25

SEQ ID NO: 52         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 52
gcagcaaata ttgatttcta caacc                                         25

SEQ ID NO: 53         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 53
cagcaaatat tgatttctac aacca                                         25

SEQ ID NO: 54         moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..24
                      note = RNA
misc_feature          25
                      note = DNA
SEQUENCE: 54
agcaaatatt gatttctaca accat                                         25

SEQ ID NO: 55         moltype = DNA  length = 25
FEATURE               Location/Qualifiers
misc_feature          1..25
                      note = Synthetic Polynucleotide
source                1..25
                      mol_type = other DNA
                      organism = synthetic construct
```

```
misc_feature          1..23
                      note = RNA
misc_feature          24
                      note = DNA
misc_feature          25
                      note = RNA
SEQUENCE: 55
gcaaatattg atttctacaa ccatc                                       25

SEQ ID NO: 56         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 56
atattgattt ctacaaccat cttga                                       25

SEQ ID NO: 57         moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 57
ttgatttcta caaccatctt gataa                                       25

SEQ ID NO: 58         moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..24
                      note = RNA
misc_feature          25
                      note = DNA
SEQUENCE: 58
gatttctaca accatcttga taagt                                       25

SEQ ID NO: 59         moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..23
                      note = RNA
misc_feature          24..25
                      note = DNA
SEQUENCE: 59
atttctacaa ccatcttgat aagtt                                       25

SEQ ID NO: 60         moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..23
                      note = RNA
misc_feature          24
                      note = DNA
misc_feature          25
                      note = RNA
SEQUENCE: 60
ttctacaacc atcttgataa gttta                                       25

SEQ ID NO: 61         moltype = RNA  length = 25
FEATURE               Location/Qualifiers
misc_feature          1..25
                      note = Synthetic Polynucleotide
source                1..25
                      mol_type = other RNA
```

```
                         organism = synthetic construct
SEQUENCE: 61
ctacaaccat cttgataagt ttaac                                           25

SEQ ID NO: 62            moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 62
tacaaccatc ttgataagtt taaca                                           25

SEQ ID NO: 63            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..24
                         note = RNA
misc_feature             25
                         note = DNA
SEQUENCE: 63
acaaccatct tgataagttt aacat                                           25

SEQ ID NO: 64            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24..25
                         note = DNA
SEQUENCE: 64
caaccatctt gataagttta acatt                                           25

SEQ ID NO: 65            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24
                         note = DNA
misc_feature             25
                         note = RNA
SEQUENCE: 65
aaccatcttg ataagtttaa cattg                                           25

SEQ ID NO: 66            moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 66
accatcttga taagtttaac attga                                           25

SEQ ID NO: 67            moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 67
ccatcttgat aagtttaaca ttgac                                           25

SEQ ID NO: 68            moltype = RNA  length = 25
```

```
FEATURE                Location/Qualifiers
misc_feature           1..25
                       note = Synthetic Polynucleotide
source                 1..25
                       mol_type = other RNA
                       organism = synthetic construct
SEQUENCE: 68
catcttgata agtttaacat tgaca                                        25

SEQ ID NO: 69          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 69
atcttgataa gtttaacatt gacaa                                        25

SEQ ID NO: 70          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 70
gttcaccacg gtttctgaaa taaca                                        25

SEQ ID NO: 71          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 71
caccacggtt tctgaaataa cagca                                        25

SEQ ID NO: 72          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 72
ccacggtttc tgaaataaca gcaat                                        25

SEQ ID NO: 73          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 73
cacggtttct gaaataacag caata                                        25

SEQ ID NO: 74          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 74
cggtttctga aataacagca ataga                                        25
```

-continued

```
SEQ ID NO: 75          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 75
ggtttctgaa ataacagcaa tagaa                                        25

SEQ ID NO: 76          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 76
gtttctgaaa taacagcaat agaag                                        25

SEQ ID NO: 77          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 77
ctgaaataac agcaatagaa gctga                                        25

SEQ ID NO: 78          moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 78
aagagaaagc ctgatgtagt tactc                                        25

SEQ ID NO: 79          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 79
agagaaagcc tgatgtagtt actcc                                        25

SEQ ID NO: 80          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 80
ggcttgaatg ttaagaaatt ttcag                                        25

SEQ ID NO: 81          moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 81
gcttgaatgt taagaaattt tcagc                                        25

SEQ ID NO: 82          moltype = RNA  length = 25
FEATURE                Location/Qualifiers
misc_feature           1..25
```

```
                         note = Synthetic Polynucleotide
source                   1..25
                         mol_type = other RNA
                         organism = synthetic construct
SEQUENCE: 82
cttgaatgtt aagaaatttt cagca                                        25

SEQ ID NO: 83            moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 83
ttgaatgtta agaaattttc agcag                                        25

SEQ ID NO: 84            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..24
                         note = RNA
misc_feature             25
                         note = DNA
SEQUENCE: 84
tgaatgttaa gaaattttca gcagt                                        25

SEQ ID NO: 85            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24
                         note = DNA
misc_feature             25
                         note = RNA
SEQUENCE: 85
gaatgttaag aaattttcag cagtg                                        25

SEQ ID NO: 86            moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 86
atgttaagaa attttcagca gtgca                                        25

SEQ ID NO: 87            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24..25
                         note = DNA
SEQUENCE: 87
agaaattttc agcagtgcat gagtt                                        25

SEQ ID NO: 88            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
```

```
                         note = RNA
misc_feature             24
                         note = DNA
misc_feature             25
                         note = RNA
SEQUENCE: 88
agcagtgcat gagtttcaaa atcta                                           25

SEQ ID NO: 89            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..24
                         note = RNA
misc_feature             25
                         note = DNA
SEQUENCE: 89
agattttgtt cgaggtcatt tctat                                           25

SEQ ID NO: 90            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24
                         note = DNA
misc_feature             25
                         note = RNA
SEQUENCE: 90
gttcgaggtc atttctatgg tcatc                                           25

SEQ ID NO: 91            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..24
                         note = RNA
misc_feature             25
                         note = DNA
SEQUENCE: 91
ttcgaggtca tttctatggt catct                                           25

SEQ ID NO: 92            moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24
                         note = DNA
misc_feature             25
                         note = RNA
SEQUENCE: 92
tcgaggtcat ttctatggtc atctc                                           25

SEQ ID NO: 93            moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 93
cgaggtcatt tctatggtca tctcg                                           25

SEQ ID NO: 94            moltype = RNA  length = 25
```

```
FEATURE                 Location/Qualifiers
misc_feature            1..25
                        note = Synthetic Polynucleotide
source                  1..25
                        mol_type = other RNA
                        organism = synthetic construct
SEQUENCE: 94
gaggtcattt ctatggtcat ctcga                                         25

SEQ ID NO: 95           moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 95
aggtcatttc tatggtcatc tcgac                                         25

SEQ ID NO: 96           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 96
ggtcatttct atggtcatct cgact                                         25

SEQ ID NO: 97           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 97
gtcatttcta tggtcatctc gactt                                         25

SEQ ID NO: 98           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 98
tgaaaagact ttgttccttt tcatt                                         25

SEQ ID NO: 99           moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 99
gaaaagactt tgttcctttt cattg                                         25

SEQ ID NO: 100          moltype = DNA  length = 25
FEATURE                 Location/Qualifiers
```

-continued

```
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 100
aaagactttg ttccttttca ttgct                                        25

SEQ ID NO: 101         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 101
ctgaggatgc ataaaagtga catca                                        25

SEQ ID NO: 102         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 102
gaggatgcat aaaagtgaca tcaca                                        25

SEQ ID NO: 103         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 103
tttttcatta tgcctgccaa gacaa                                        25

SEQ ID NO: 104         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 104
tcattatgcc tgccaagaca aataa                                        25

SEQ ID NO: 105         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 105
cattatgcct gccaagacaa ataat                                        25

SEQ ID NO: 106         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24..25
                       note = DNA
SEQUENCE: 106
attatgcctg ccaagacaaa taatt                                        25
```

```
SEQ ID NO: 107         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 107
atgcctgcca agacaaataa tttca                                        25

SEQ ID NO: 108         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 108
aatttcaacg tggaaaccct gaaag                                        25

SEQ ID NO: 109         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 109
atttcaacgt ggaaaccctg aaagg                                        25

SEQ ID NO: 110         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 110
tttcaacgtg gaaaccctga aagga                                        25

SEQ ID NO: 111         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 111
ttcaacgtgg aaaccctgaa aggac                                        25

SEQ ID NO: 112         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 112
tcaacgtgga aaccctgaaa ggaca                                        25

SEQ ID NO: 113         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24..25
                       note = DNA
SEQUENCE: 113
ttgcacattc tgtgaaggaa aagtt                                        25

SEQ ID NO: 114         moltype = DNA  length = 25
FEATURE                Location/Qualifiers
misc_feature           1..25
                       note = Synthetic Polynucleotide
```

```
source                  1..25
                        mol_type = other DNA
                        organism = synthetic construct
misc_feature            1..23
                        note = RNA
misc_feature            24..25
                        note = DNA
SEQUENCE: 114
tgcacattct gtgaaggaaa agttt                                        25

SEQ ID NO: 115          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 115
gcacattctg tgaaggaaaa gtttg                                        25

SEQ ID NO: 116          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 116
attctgtgaa ggaaaagttt ggaaa                                        25

SEQ ID NO: 117          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 117
gtgaaggaaa agtttggaaa aaaac                                        25

SEQ ID NO: 118          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 118
gaaaaaaact ctatgatgca ttatt                                        25

SEQ ID NO: 119          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 119
aaaaaaactc tatgatgcat tatta                                        25

SEQ ID NO: 120          moltype = RNA  length = 25
FEATURE                 Location/Qualifiers
misc_feature            1..25
```

```
                        note = Synthetic Polynucleotide
source                  1..25
                        mol_type = other RNA
                        organism = synthetic construct
SEQUENCE: 120
aaaaaactct atgatgcatt attaa                                           25

SEQ ID NO: 121          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 121
aaaaactcta tgatgcatta ttaag                                           25

SEQ ID NO: 122          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 122
ttattaagag gagaaattcc tgacc                                           25

SEQ ID NO: 123          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 123
tattaagagg agaaattcct gacct                                           25

SEQ ID NO: 124          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 124
attaagagga gaaattcctg acctg                                           25

SEQ ID NO: 125          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 125
ttaagaggag aaattcctga cctga                                           25

SEQ ID NO: 126          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 126
taagaggaga aattcctgac ctgaa                                           25

SEQ ID NO: 127          moltype = RNA  length = 25
FEATURE                 Location/Qualifiers
```

```
misc_feature          1..25
                      note = Synthetic Polynucleotide
source                1..25
                      mol_type = other RNA
                      organism = synthetic construct
SEQUENCE: 127
aagaggagaa attcctgacc tgaac                                        25

SEQ ID NO: 128        moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 128
cgagatgatc taacaattat gaaaa                                        25

SEQ ID NO: 129        moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 129
agatgatcta acaattatga aaaga                                        25

SEQ ID NO: 130        moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 130
gatgatctaa caattatgaa aagag                                        25

SEQ ID NO: 131        moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 131
atgatctaac aattatgaaa agagc                                        25

SEQ ID NO: 132        moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..23
                      note = RNA
misc_feature          24..25
                      note = DNA
SEQUENCE: 132
acaattatga aaagagccat ctttt                                        25

SEQ ID NO: 133        moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 133
gaaaagagcc atcttttcaa ctcag                                        25

SEQ ID NO: 134        moltype = RNA  length = 25
FEATURE               Location/Qualifiers
misc_feature          1..25
                      note = Synthetic Polynucleotide
source                1..25
                      mol_type = other RNA
                      organism = synthetic construct
```

```
SEQUENCE: 134
cccatcctca gcaccattag acgga                                          25

SEQ ID NO: 135          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 135
ccatcctcag caccattaga cggat                                          25

SEQ ID NO: 136          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 136
catcctcagc accattagac ggatt                                          25

SEQ ID NO: 137          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 137
atcctcagca ccattagacg gattg                                          25

SEQ ID NO: 138          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 138
tcctcagcac cattagacgg attgg                                          25

SEQ ID NO: 139          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 139
cccatggact atgaagagtt tgtta                                          25

SEQ ID NO: 140          moltype = RNA  length = 25
FEATURE                 Location/Qualifiers
misc_feature            1..25
                        note = Synthetic Polynucleotide
source                  1..25
                        mol_type = other RNA
```

```
                         organism = synthetic construct
SEQUENCE: 140
ccatggacta tgaagagttt gttag                                          25

SEQ ID NO: 141           moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24
                         note = DNA
misc_feature             25
                         note = RNA
SEQUENCE: 141
cttggagtat ttccatcata ctatg                                          25

SEQ ID NO: 142           moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 142
tggagtattt ccatcatact atgaa                                          25

SEQ ID NO: 143           moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 143
ggagtatttc catcatacta tgaac                                          25

SEQ ID NO: 144           moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 144
gagtatttcc atcatactat gaacc                                          25

SEQ ID NO: 145           moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24
                         note = DNA
misc_feature             25
                         note = RNA
SEQUENCE: 145
tatttccatc atactatgaa ccctg                                          25

SEQ ID NO: 146           moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..24
                         note = RNA
misc_feature             25
                         note = DNA
SEQUENCE: 146
atactccagc tgaatgcact gtgat                                          25
```

```
SEQ ID NO: 147         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 147
ggcagatatt accagcatgc cagac                                        25

SEQ ID NO: 148         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 148
gcagatatta ccagcatgcc agaca                                        25

SEQ ID NO: 149         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 149
cagatattac cagcatgcca gacac                                        25

SEQ ID NO: 150         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 150
agatattacc agcatgccag acacc                                        25

SEQ ID NO: 151         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 151
gatattacca gcatgccaga cacct                                        25

SEQ ID NO: 152         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 152
atattaccag catgccagac acctg                                        25

SEQ ID NO: 153         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 153
```

```
tattaccagc atgccagaca cctga                                        25

SEQ ID NO: 154         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 154
attaccagca tgccagacac ctgac                                        25

SEQ ID NO: 155         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 155
ttaccagcat gccagacacc tgaca                                        25

SEQ ID NO: 156         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 156
taccagcatg ccagacacct gacat                                        25

SEQ ID NO: 157         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24..25
                       note = DNA
SEQUENCE: 157
accagcatgc cagacacctg acatt                                        25

SEQ ID NO: 158         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 158
ccagcatgcc agacacctga catta                                        25

SEQ ID NO: 159         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 159
cagcatgcca gacacctgac attaa                                        25

SEQ ID NO: 160         moltype = RNA  length = 25
FEATURE                Location/Qualifiers
misc_feature           1..25
```

```
                        note = Synthetic Polynucleotide
source                  1..25
                        mol_type = other RNA
                        organism = synthetic construct
SEQUENCE: 160
agcatgccag acacctgaca ttaag                                        25

SEQ ID NO: 161          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 161
gcatgccaga cacctgacat taagc                                        25

SEQ ID NO: 162          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 162
tgccagacac ctgacattaa gcaga                                        25

SEQ ID NO: 163          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 163
cctgacatta agcagagctt ttcca                                        25

SEQ ID NO: 164          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 164
aagcagagct tttccagata aattc                                        25

SEQ ID NO: 165          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 165
gcagagcttt tccagataaa ttcca                                        25

SEQ ID NO: 166          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 166
ccagataaat tccatgtgga actaa                                        25

SEQ ID NO: 167          moltype = RNA  length = 25
FEATURE                 Location/Qualifiers
misc_feature            1..25
                        note = Synthetic Polynucleotide
source                  1..25
                        mol_type = other RNA
```

-continued

```
                         organism = synthetic construct
SEQUENCE: 167
cagataaatt ccatgtggaa ctaac                                          25

SEQ ID NO: 168           moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 168
tcctcagtac caccttctcc ttcag                                          25

SEQ ID NO: 169           moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 169
cctcagtacc accttctcct tcagg                                          25

SEQ ID NO: 170           moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..24
                         note = RNA
misc_feature             25
                         note = DNA
SEQUENCE: 170
gaaagggatc ggttaaatat caagt                                          25

SEQ ID NO: 171           moltype = RNA  length = 25
FEATURE                  Location/Qualifiers
misc_feature             1..25
                         note = Synthetic Polynucleotide
source                   1..25
                         mol_type = other RNA
                         organism = synthetic construct
SEQUENCE: 171
agggatcggt taaatatcaa gtcac                                          25

SEQ ID NO: 172           moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24..25
                         note = DNA
SEQUENCE: 172
atcggttaaa tatcaagtca ccatt                                          25

SEQ ID NO: 173           moltype = DNA  length = 25
FEATURE                  Location/Qualifiers
misc_feature             1..25
                         note = Synthetic Polynucleotide
source                   1..25
                         mol_type = other DNA
                         organism = synthetic construct
misc_feature             1..23
                         note = RNA
misc_feature             24
                         note = DNA
misc_feature             25
                         note = RNA
SEQUENCE: 173
ggttaaatat caagtcacca ttttc                                          25

SEQ ID NO: 174           moltype = RNA  length = 25
```

```
FEATURE               Location/Qualifiers
misc_feature          1..25
                      note = Synthetic Polynucleotide
source                1..25
                      mol_type = other RNA
                      organism = synthetic construct
SEQUENCE: 174
gttaaatatc aagtcaccat tttca                                       25

SEQ ID NO: 175        moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..23
                      note = RNA
misc_feature          24
                      note = DNA
misc_feature          25
                      note = RNA
SEQUENCE: 175
aaatatcaag tcaccatttt cactg                                       25

SEQ ID NO: 176        moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..23
                      note = RNA
misc_feature          24
                      note = DNA
misc_feature          25
                      note = RNA
SEQUENCE: 176
aagaaaaagc tgcatggtga atata                                       25

SEQ ID NO: 177        moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 177
agaaaaagct gcatggtgaa tataa                                       25

SEQ ID NO: 178        moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 178
aaaaagctgc atggtgaata taaga                                       25

SEQ ID NO: 179        moltype = RNA  length = 25
FEATURE               Location/Qualifiers
misc_feature          1..25
                      note = Synthetic Polynucleotide
source                1..25
                      mol_type = other RNA
                      organism = synthetic construct
SEQUENCE: 179
aaaagctgca tggtgaatat aagaa                                       25

SEQ ID NO: 180        moltype = DNA  length = 25
FEATURE               Location/Qualifiers
misc_feature          1..25
                      note = Synthetic Polynucleotide
source                1..25
                      mol_type = other DNA
                      organism = synthetic construct
misc_feature          1..24
```

```
                        note = RNA
misc_feature            25
                        note = DNA
SEQUENCE: 180
aagctgcatg gtgaatataa gaact                                              25

SEQ ID NO: 181          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 181
gctgcatggt gaatataaga actga                                              25

SEQ ID NO: 182          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 182
ctgcatggtg aatataagaa ctgaa                                              25

SEQ ID NO: 183          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 183
gcatggtgaa tataagaact gaatt                                              25

SEQ ID NO: 184          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 184
catggtgaat ataagaactg aattc                                              25

SEQ ID NO: 185          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 185
atggtgaata taagaactga attct                                              25

SEQ ID NO: 186          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
```

-continued

```
misc_feature           24
                       note = DNA
misc_feature           25
                       note = RNA
SEQUENCE: 186
tggtgaatat aagaactgaa ttcta                                          25

SEQ ID NO: 187         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 187
ggtgaatata agaactgaat tctac                                          25

SEQ ID NO: 188         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 188
gtgaatataa gaactgaatt ctaca                                          25

SEQ ID NO: 189         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 189
aatataagaa ctgaattcta catgt                                          25

SEQ ID NO: 190         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 190
atataagaac tgaattctac atgtg                                          25

SEQ ID NO: 191         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 191
ataagaactg aattctacat gtgct                                          25

SEQ ID NO: 192         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 192
```

```
aagaactgaa ttctacatgt gctgc                                       25

SEQ ID NO: 193         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 193
tcagccatct tccaaaatgc acctggc                                     27

SEQ ID NO: 194         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 194
atcagccatc ttccaaaatg cacctgg                                     27

SEQ ID NO: 195         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 195
tatcagccat cttccaaaat gcacctg                                     27

SEQ ID NO: 196         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 196
ctatcagcca tcttccaaaa tgcacct                                     27

SEQ ID NO: 197         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 197
tctatcagcc atcttccaaa atgcacc                                     27

SEQ ID NO: 198         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 198
aaaagtacca cataaggact tccttct                                     27

SEQ ID NO: 199         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 199
tcaaaaagta ccacataagg acttcct                                     27

SEQ ID NO: 200         moltype = RNA  length = 27
FEATURE                Location/Qualifiers
misc_feature           1..27
                       note = Synthetic Polynucleotide
source                 1..27
                       mol_type = other RNA
                       organism = synthetic construct
```

```
SEQUENCE: 200
gtcaaaaagt accacataag gacttcc                                     27

SEQ ID NO: 201         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 201
tgtcaaaaag taccacataa ggacttc                                     27

SEQ ID NO: 202         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 202
atgtcaaaaa gtaccacata aggactt                                     27

SEQ ID NO: 203         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 203
ctatgtcaaa aagtaccaca taaggac                                     27

SEQ ID NO: 204         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 204
ctgaatagcc tatgtcaaaa agtacca                                     27

SEQ ID NO: 205         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 205
atatcagcat atcattggct tctcggt                                     27

SEQ ID NO: 206         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 206
aatatcagca tatcattggc ttctcgg                                     27

SEQ ID NO: 207         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 207
aaatatcagc atatcattgg cttctcg                                     27

SEQ ID NO: 208         moltype = RNA  length = 27
FEATURE                Location/Qualifiers
misc_feature           1..27
                       note = Synthetic Polynucleotide
source                 1..27
                       mol_type = other RNA
```

```
                        organism = synthetic construct
SEQUENCE: 208
caaatatcag catatcattg gcttctc                                          27

SEQ ID NO: 209          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 209
tccaaatatc agcatatcat tggcttc                                          27

SEQ ID NO: 210          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 210
atccaaatat cagcatatca ttggctt                                          27

SEQ ID NO: 211          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 211
gatccaaata tcagcatatc attggct                                          27

SEQ ID NO: 212          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 212
aagatccaaa tatcagcata tcattgg                                          27

SEQ ID NO: 213          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 213
aaagatccaa atatcagcat atcattg                                          27

SEQ ID NO: 214          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 214
taaagatcca aatatcagca tatcatt                                          27

SEQ ID NO: 215          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 215
gttaaagatc caaatatcag catatca                                          27

SEQ ID NO: 216          moltype = RNA  length = 27
FEATURE                 Location/Qualifiers
misc_feature            1..27
                        note = Synthetic Polynucleotide
source                  1..27
```

```
                         mol_type = other RNA
                         organism = synthetic construct
SEQUENCE: 216
cagttaaaga tccaaatatc agcatat                                          27

SEQ ID NO: 217           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 217
cttttaagaa ccaggcagtt aaagatc                                          27

SEQ ID NO: 218           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 218
tcttttaaga accaggcagt taaagat                                          27

SEQ ID NO: 219           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 219
ctcttttaag aaccaggcag ttaaaga                                          27

SEQ ID NO: 220           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 220
cctcttttaa gaaccaggca gttaaag                                          27

SEQ ID NO: 221           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 221
acctctttta agaaccaggc agttaaa                                          27

SEQ ID NO: 222           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 222
gcctgccatt catggaattg ggcaacg                                          27

SEQ ID NO: 223           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 223
agcctgccat tcatggaatt gggcaac                                          27

SEQ ID NO: 224           moltype = RNA  length = 27
FEATURE                  Location/Qualifiers
misc_feature             1..27
                         note = Synthetic Polynucleotide
```

```
source                  1..27
                        mol_type = other RNA
                        organism = synthetic construct
SEQUENCE: 224
cagcctgcca ttcatggaat tgggcaa                                       27

SEQ ID NO: 225          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 225
ccagcctgcc attcatggaa ttgggca                                       27

SEQ ID NO: 226          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 226
tccagcctgc cattcatgga attgggc                                       27

SEQ ID NO: 227          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 227
ttccagcctg ccattcatgg aattggg                                       27

SEQ ID NO: 228          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 228
attccagcct gccattcatg gaattgg                                       27

SEQ ID NO: 229          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 229
aattccagcc tgccattcat ggaattg                                       27

SEQ ID NO: 230          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 230
caattccagc ctgccattca tggaatt                                       27

SEQ ID NO: 231          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 231
ccaattccag cctgccattc atggaat                                       27

SEQ ID NO: 232          moltype = RNA  length = 27
FEATURE                 Location/Qualifiers
misc_feature            1..27
```

```
                        note = Synthetic Polynucleotide
source                  1..27
                        mol_type = other RNA
                        organism = synthetic construct
SEQUENCE: 232
aatattgtgg caataggaag tttcctg                                         27

SEQ ID NO: 233          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 233
tcaatatttg ctgcacagag atacctc                                         27

SEQ ID NO: 234          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 234
atcaatattt gctgcacaga gatacct                                         27

SEQ ID NO: 235          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 235
aatcaatatt tgctgcacag agatacc                                         27

SEQ ID NO: 236          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 236
aaatcaatat ttgctgcaca gagatac                                         27

SEQ ID NO: 237          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 237
gaaatcaata tttgctgcac agagata                                         27

SEQ ID NO: 238          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 238
agaaatcaat atttgctgca cagagat                                         27

SEQ ID NO: 239          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 239
tagaaatcaa tatttgctgc acagaga                                         27

SEQ ID NO: 240          moltype = RNA  length = 27
FEATURE                 Location/Qualifiers
```

```
misc_feature            1..27
                        note = Synthetic Polynucleotide
source                  1..27
                        mol_type = other RNA
                        organism = synthetic construct
SEQUENCE: 240
gtagaaatca atatttgctg cacagag                                      27

SEQ ID NO: 241          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 241
tgtagaaatc aatatttgct gcacaga                                      27

SEQ ID NO: 242          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 242
ttgtagaaat caatatttgc tgcacag                                      27

SEQ ID NO: 243          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 243
gttgtagaaa tcaatatttg ctgcaca                                      27

SEQ ID NO: 244          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 244
ggttgtagaa atcaatattt gctgcac                                      27

SEQ ID NO: 245          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 245
tggttgtaga aatcaatatt tgctgca                                      27

SEQ ID NO: 246          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 246
atggttgtag aaatcaatat ttgctgc                                      27

SEQ ID NO: 247          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 247
gatggttgta gaaatcaata tttgctg                                      27

SEQ ID NO: 248          moltype = RNA  length = 27
```

```
FEATURE               Location/Qualifiers
misc_feature          1..27
                      note = Synthetic Polynucleotide
source                1..27
                      mol_type = other RNA
                      organism = synthetic construct
SEQUENCE: 248
tcaagatggt tgtagaaatc aatattt                                      27

SEQ ID NO: 249        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 249
ttatcaagat ggttgtagaa atcaata                                      27

SEQ ID NO: 250        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 250
acttatcaag atggttgtag aaatcaa                                      27

SEQ ID NO: 251        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 251
aacttatcaa gatggttgta gaaatca                                      27

SEQ ID NO: 252        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 252
taaacttatc aagatggttg tagaaat                                      27

SEQ ID NO: 253        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 253
gttaaactta tcaagatggt tgtagaa                                      27

SEQ ID NO: 254        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 254
tgttaaactt atcaagatgg ttgtaga                                      27

SEQ ID NO: 255        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 255
atgttaaact tatcaagatg gttgtag                                      27
```

-continued

```
SEQ ID NO: 256          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 256
aatgttaaac ttatcaagat ggttgta                                      27

SEQ ID NO: 257          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 257
caatgttaaa cttatcaaga tggttgt                                      27

SEQ ID NO: 258          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 258
tcaatgttaa acttatcaag atggttg                                      27

SEQ ID NO: 259          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 259
gtcaatgtta aacttatcaa gatggtt                                      27

SEQ ID NO: 260          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 260
tgtcaatgtt aaacttatca agatggt                                      27

SEQ ID NO: 261          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 261
ttgtcaatgt taaacttatc aagatgg                                      27

SEQ ID NO: 262          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 262
tgttatttca gaaaccgtgg tgaacac                                      27

SEQ ID NO: 263          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 263
tgctgttatt tcagaaaccg tggtgaa                                      27
```

```
SEQ ID NO: 264         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 264
attgctgtta tttcagaaac cgtggtg                                    27

SEQ ID NO: 265         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 265
tattgctgtt atttcagaaa ccgtggt                                    27

SEQ ID NO: 266         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 266
tctattgctg ttatttcaga aaccgtg                                    27

SEQ ID NO: 267         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 267
ttctattgct gttatttcag aaaccgt                                    27

SEQ ID NO: 268         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 268
cttctattgc tgttatttca gaaaccg                                    27

SEQ ID NO: 269         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 269
tcagcttcta ttgctgttat ttcagaa                                    27

SEQ ID NO: 270         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 270
gagtaactac atcaggcttt ctcttca                                    27

SEQ ID NO: 271         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 271
```

```
ggagtaacta catcaggctt tctcttc                                    27

SEQ ID NO: 272          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 272
ctgaaaattt cttaacattc aagccgt                                    27

SEQ ID NO: 273          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 273
gctgaaaatt tcttaacatt caagccg                                    27

SEQ ID NO: 274          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 274
tgctgaaaat ttcttaacat tcaagcc                                    27

SEQ ID NO: 275          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 275
ctgctgaaaa tttcttaaca ttcaagc                                    27

SEQ ID NO: 276          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 276
actgctgaaa atttcttaac attcaag                                    27

SEQ ID NO: 277          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 277
cactgctgaa aatttcttaa cattcaa                                    27

SEQ ID NO: 278          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 278
tgcactgctg aaaatttctt aacattc                                    27

SEQ ID NO: 279          moltype = RNA  length = 27
FEATURE                 Location/Qualifiers
misc_feature            1..27
                        note = Synthetic Polynucleotide
source                  1..27
                        mol_type = other RNA
                        organism = synthetic construct
```

```
SEQUENCE: 279
aactcatgca ctgctgaaaa tttctta                                 27

SEQ ID NO: 280         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 280
tagattttga aactcatgca ctgctga                                 27

SEQ ID NO: 281         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 281
atagaaatga cctcgaacaa aatcttg                                 27

SEQ ID NO: 282         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 282
gatgaccata gaaatgacct cgaacaa                                 27

SEQ ID NO: 283         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 283
agatgaccat agaaatgacc tcgaaca                                 27

SEQ ID NO: 284         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 284
gagatgacca tagaaatgac ctcgaac                                 27

SEQ ID NO: 285         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 285
cgagatgacc atagaaatga cctcgaa                                 27

SEQ ID NO: 286         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 286
tcgagatgac catagaaatg acctcga                                 27

SEQ ID NO: 287         moltype = RNA  length = 27
FEATURE                Location/Qualifiers
misc_feature           1..27
                       note = Synthetic Polynucleotide
source                 1..27
                       mol_type = other RNA
```

```
                        organism = synthetic construct
SEQUENCE: 287
gtcgagatga ccatagaaat gacctcg                                        27

SEQ ID NO: 288          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 288
agtcgagatg accatagaaa tgacctc                                        27

SEQ ID NO: 289          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 289
aagtcgagat gaccatagaa atgacct                                        27

SEQ ID NO: 290          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 290
aatgaaaagg aacaaagtct tttcaag                                        27

SEQ ID NO: 291          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 291
caatgaaaag gaacaaagtc ttttcaa                                        27

SEQ ID NO: 292          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 292
agcaatgaaa aggaacaaag tcttttc                                        27

SEQ ID NO: 293          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 293
tgatgtcact tttatgcatc ctcagca                                        27

SEQ ID NO: 294          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 294
tgtgatgtca cttttatgca tcctcag                                        27

SEQ ID NO: 295          moltype = RNA  length = 27
FEATURE                 Location/Qualifiers
misc_feature            1..27
                        note = Synthetic Polynucleotide
source                  1..27
```

```
                        mol_type = other RNA
                        organism = synthetic construct
SEQUENCE: 295
ttgtcttggc aggcataatg aaaaaca                                          27

SEQ ID NO: 296          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 296
ttatttgtct tggcaggcat aatgaaa                                          27

SEQ ID NO: 297          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 297
attatttgtc ttggcaggca taatgaa                                          27

SEQ ID NO: 298          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 298
aattatttgt cttggcaggc ataatga                                          27

SEQ ID NO: 299          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 299
tgaaattatt tgtcttggca ggcataa                                          27

SEQ ID NO: 300          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 300
ctttcagggt ttccacgttg aaattat                                          27

SEQ ID NO: 301          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 301
cctttcaggg tttccacgtt gaaatta                                          27

SEQ ID NO: 302          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 302
tcctttcagg gtttccacgt tgaaatt                                          27

SEQ ID NO: 303          moltype = RNA  length = 27
FEATURE                 Location/Qualifiers
misc_feature            1..27
                        note = Synthetic Polynucleotide
```

```
source                  1..27
                        mol_type = other RNA
                        organism = synthetic construct
SEQUENCE: 303
gtcctttcag ggtttccacg ttgaaat                                      27

SEQ ID NO: 304          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 304
tgtcctttca gggtttccac gttgaaa                                      27

SEQ ID NO: 305          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 305
aacttttcct tcacagaatg tgcaaca                                      27

SEQ ID NO: 306          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 306
aaacttttcc ttcacagaat gtgcaac                                      27

SEQ ID NO: 307          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 307
caaacttttc cttcacagaa tgtgcaa                                      27

SEQ ID NO: 308          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 308
tttccaaact tttccttcac agaatgt                                      27

SEQ ID NO: 309          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 309
gtttttttcc aaacttttcc ttcacag                                      27

SEQ ID NO: 310          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 310
aataatgcat catagagttt ttttcca                                      27

SEQ ID NO: 311          moltype = RNA  length = 27
FEATURE                 Location/Qualifiers
misc_feature            1..27
```

```
                      note = Synthetic Polynucleotide
source                1..27
                      mol_type = other RNA
                      organism = synthetic construct
SEQUENCE: 311
taataatgca tcatagagtt tttttcc                                    27

SEQ ID NO: 312        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 312
ttaataatgc atcatagagt ttttttc                                    27

SEQ ID NO: 313        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 313
cttaataatg catcatagag ttttttt                                    27

SEQ ID NO: 314        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 314
ggtcaggaat ttctcctctt aataatg                                    27

SEQ ID NO: 315        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 315
aggtcaggaa tttctcctct taataat                                    27

SEQ ID NO: 316        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 316
caggtcagga atttctcctc ttaataa                                    27

SEQ ID NO: 317        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 317
tcaggtcagg aatttctcct cttaata                                    27

SEQ ID NO: 318        moltype = RNA  length = 27
FEATURE               Location/Qualifiers
misc_feature          1..27
                      note = Synthetic Polynucleotide
source                1..27
                      mol_type = other RNA
                      organism = synthetic construct
SEQUENCE: 318
ttcaggtcag gaatttctcc tcttaat                                    27

SEQ ID NO: 319        moltype = RNA  length = 27
FEATURE               Location/Qualifiers
```

```
misc_feature            1..27
                        note = Synthetic Polynucleotide
source                  1..27
                        mol_type = other RNA
                        organism = synthetic construct
SEQUENCE: 319
gttcaggtca ggaatttctc ctcttaa                                        27

SEQ ID NO: 320          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 320
ttttcataat tgttagatca tctcgat                                        27

SEQ ID NO: 321          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 321
tcttttcata attgttagat catctcg                                        27

SEQ ID NO: 322          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 322
ctcttttcat aattgttaga tcatctc                                        27

SEQ ID NO: 323          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 323
gctcttttca taattgttag atcatct                                        27

SEQ ID NO: 324          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 324
aaaagatggc tcttttcata attgtta                                        27

SEQ ID NO: 325          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 325
ctgagttgaa aagatggctc ttttcat                                        27

SEQ ID NO: 326          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 326
tccgtctaat ggtgctgagg atggggt                                        27

SEQ ID NO: 327          moltype = RNA  length = 27
```

```
FEATURE                Location/Qualifiers
misc_feature           1..27
                       note = Synthetic Polynucleotide
source                 1..27
                       mol_type = other RNA
                       organism = synthetic construct
SEQUENCE: 327
atccgtctaa tggtgctgag gatgggg                                          27

SEQ ID NO: 328         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 328
aatccgtcta atggtgctga ggatggg                                          27

SEQ ID NO: 329         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 329
caatccgtct aatggtgctg aggatgg                                          27

SEQ ID NO: 330         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 330
ccaatccgtc taatggtgct gaggatg                                          27

SEQ ID NO: 331         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 331
taacaaactc ttcatagtcc atgggta                                          27

SEQ ID NO: 332         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 332
ctaacaaact cttcatagtc catgggt                                          27

SEQ ID NO: 333         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 333
catagtatga tggaaatact ccaagat                                          27

SEQ ID NO: 334         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 334
ttcatagtat gatggaaata ctccaag                                          27
```

```
SEQ ID NO: 335          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 335
gttcatagta tgatggaaat actccaa                                      27

SEQ ID NO: 336          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 336
ggttcatagt atgatggaaa tactcca                                      27

SEQ ID NO: 337          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 337
cagggttcat agtatgatgg aaatact                                      27

SEQ ID NO: 338          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 338
atcacagtgc attcagctgg agtataa                                      27

SEQ ID NO: 339          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 339
gtctggcatg ctggtaatat ctgccta                                      27

SEQ ID NO: 340          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 340
tgtctggcat gctggtaata tctgcct                                      27

SEQ ID NO: 341          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 341
gtgtctggca tgctggtaat atctgcc                                      27

SEQ ID NO: 342          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 342
ggtgtctggc atgctggtaa tatctgc                                      27
```

```
SEQ ID NO: 343          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 343
aggtgtctgg catgctggta atatctg                                      27

SEQ ID NO: 344          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 344
caggtgtctg gcatgctggt aatatct                                      27

SEQ ID NO: 345          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 345
tcaggtgtct ggcatgctgg taatatc                                      27

SEQ ID NO: 346          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 346
gtcaggtgtc tggcatgctg gtaatat                                      27

SEQ ID NO: 347          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 347
tgtcaggtgt ctggcatgct ggtaata                                      27

SEQ ID NO: 348          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 348
atgtcaggtg tctggcatgc tggtaat                                      27

SEQ ID NO: 349          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 349
aatgtcaggt gtctggcatg ctggtaa                                      27

SEQ ID NO: 350          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 350
```

```
taatgtcagg tgtctggcat gctggta                                      27

SEQ ID NO: 351         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 351
ttaatgtcag gtgtctggca tgctggt                                      27

SEQ ID NO: 352         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 352
cttaatgtca ggtgtctggc atgctgg                                      27

SEQ ID NO: 353         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 353
gcttaatgtc aggtgtctgg catgctg                                      27

SEQ ID NO: 354         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 354
tctgcttaat gtcaggtgtc tggcatg                                      27

SEQ ID NO: 355         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 355
tggaaaagct ctgcttaatg tcaggtg                                      27

SEQ ID NO: 356         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 356
gaatttatct ggaaaagctc tgcttaa                                      27

SEQ ID NO: 357         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 357
tggaatttat ctggaaaagc tctgctt                                      27

SEQ ID NO: 358         moltype = RNA  length = 27
FEATURE                Location/Qualifiers
misc_feature           1..27
                       note = Synthetic Polynucleotide
source                 1..27
                       mol_type = other RNA
                       organism = synthetic construct
```

```
SEQUENCE: 358
ttagttccac atggaattta tctggaa                                27

SEQ ID NO: 359          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 359
gttagttcca catggaattt atctgga                                27

SEQ ID NO: 360          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 360
ctgaaggaga aggtggtact gaggaag                                27

SEQ ID NO: 361          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 361
cctgaaggag aaggtggtac tgaggaa                                27

SEQ ID NO: 362          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 362
acttgatatt taaccgatcc ctttcag                                27

SEQ ID NO: 363          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 363
gtgacttgat atttaaccga tcccttt                                27

SEQ ID NO: 364          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 364
aatggtgact tgatatttaa ccgatcc                                27

SEQ ID NO: 365          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 365
gaaaatggtg acttgatatt taaccga                                27

SEQ ID NO: 366          moltype = RNA  length = 27
FEATURE                 Location/Qualifiers
misc_feature            1..27
                        note = Synthetic Polynucleotide
source                  1..27
                        mol_type = other RNA
```

```
                         organism = synthetic construct
SEQUENCE: 366
tgaaaatggt gacttgatat ttaaccg                                             27

SEQ ID NO: 367           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 367
cagtgaaaat ggtgacttga tatttaa                                             27

SEQ ID NO: 368           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 368
tatattcacc atgcagcttt ttcttcc                                             27

SEQ ID NO: 369           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 369
ttatattcac catgcagctt tttcttc                                             27

SEQ ID NO: 370           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 370
tcttatattc accatgcagc tttttct                                             27

SEQ ID NO: 371           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 371
ttcttatatt caccatgcag ctttttc                                             27

SEQ ID NO: 372           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 372
agttcttata ttcaccatgc agctttt                                             27

SEQ ID NO: 373           moltype = RNA  length = 27
FEATURE                  Location/Qualifiers
misc_feature             1..27
                         note = Synthetic Polynucleotide
source                   1..27
                         mol_type = other RNA
                         organism = synthetic construct
SEQUENCE: 373
tcagttctta tattcaccat gcagctt                                             27

SEQ ID NO: 374           moltype = RNA  length = 27
FEATURE                  Location/Qualifiers
misc_feature             1..27
                         note = Synthetic Polynucleotide
source                   1..27
```

```
                        mol_type = other RNA
                        organism = synthetic construct
SEQUENCE: 374
ttcagttctt atattcacca tgcagct                                        27

SEQ ID NO: 375          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 375
aattcagttc ttatattcac catgcag                                        27

SEQ ID NO: 376          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 376
gaattcagtt cttatattca ccatgca                                        27

SEQ ID NO: 377          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 377
agaattcagt tcttatattc accatgc                                        27

SEQ ID NO: 378          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 378
tagaattcag ttcttatatt caccatg                                        27

SEQ ID NO: 379          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 379
gtagaattca gttcttatat tcaccat                                        27

SEQ ID NO: 380          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 380
tgtagaattc agttcttata ttcacca                                        27

SEQ ID NO: 381          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 381
acatgtagaa ttcagttctt atattca                                        27

SEQ ID NO: 382          moltype = RNA  length = 27
FEATURE                 Location/Qualifiers
misc_feature            1..27
                        note = Synthetic Polynucleotide
```

```
source                  1..27
                        mol_type = other RNA
                        organism = synthetic construct
SEQUENCE: 382
cacatgtaga attcagttct tatattc                                   27

SEQ ID NO: 383          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 383
agcacatgta gaattcagtt cttatat                                   27

SEQ ID NO: 384          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 384
gcagcacatg tagaattcag ttcttat                                   27

SEQ ID NO: 385          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 385
aggtgcattt tggaagatgg gcagccgaaa ggctgc                         36

SEQ ID NO: 386          moltype = RNA  length = 35
FEATURE                 Location/Qualifiers
misc_feature            1..35
                        note = Synthetic Polynucleotide
source                  1..35
                        mol_type = other RNA
                        organism = synthetic construct
SEQUENCE: 386
aggtgcattt tggaagatgg cagccgaaag gctgc                          35

SEQ ID NO: 387          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 387
ggtgcatttt ggaagatggc gcagccgaaa ggctgc                         36

SEQ ID NO: 388          moltype = RNA  length = 35
FEATURE                 Location/Qualifiers
misc_feature            1..35
                        note = Synthetic Polynucleotide
source                  1..35
                        mol_type = other RNA
                        organism = synthetic construct
SEQUENCE: 388
ggtgcatttt ggaagatggg cagccgaaag gctgc                          35

SEQ ID NO: 389          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 389
aaggaagtcc ttatgtggta gcagccgaaa ggctgc                         36

SEQ ID NO: 390          moltype = RNA  length = 35
FEATURE                 Location/Qualifiers
misc_feature            1..35
```

```
                         note = Synthetic Polynucleotide
source                   1..35
                         mol_type = other RNA
                         organism = synthetic construct
SEQUENCE: 390
aaggaagtcc ttatgtggtg cagccgaaag gctgc                           35

SEQ ID NO: 391           moltype = RNA  length = 36
FEATURE                  Location/Qualifiers
misc_feature             1..36
                         note = Synthetic Polynucleotide
source                   1..36
                         mol_type = other RNA
                         organism = synthetic construct
SEQUENCE: 391
atgatatgct gatatttgga gcagccgaaa ggctgc                          36

SEQ ID NO: 392           moltype = RNA  length = 35
FEATURE                  Location/Qualifiers
misc_feature             1..35
                         note = Synthetic Polynucleotide
source                   1..35
                         mol_type = other RNA
                         organism = synthetic construct
SEQUENCE: 392
atgatatgct gatatttggg cagccgaaag gctgc                           35

SEQ ID NO: 393           moltype = RNA  length = 36
FEATURE                  Location/Qualifiers
misc_feature             1..36
                         note = Synthetic Polynucleotide
source                   1..36
                         mol_type = other RNA
                         organism = synthetic construct
SEQUENCE: 393
agcaaatatt gatttctaca gcagccgaaa ggctgc                          36

SEQ ID NO: 394           moltype = RNA  length = 35
FEATURE                  Location/Qualifiers
misc_feature             1..35
                         note = Synthetic Polynucleotide
source                   1..35
                         mol_type = other RNA
                         organism = synthetic construct
SEQUENCE: 394
agcaaatatt gatttctacg cagccgaaag gctgc                           35

SEQ ID NO: 395           moltype = RNA  length = 36
FEATURE                  Location/Qualifiers
misc_feature             1..36
                         note = Synthetic Polynucleotide
source                   1..36
                         mol_type = other RNA
                         organism = synthetic construct
SEQUENCE: 395
ccacggtttc tgaaataaca gcagccgaaa ggctgc                          36

SEQ ID NO: 396           moltype = RNA  length = 35
FEATURE                  Location/Qualifiers
misc_feature             1..35
                         note = Synthetic Polynucleotide
source                   1..35
                         mol_type = other RNA
                         organism = synthetic construct
SEQUENCE: 396
ccacggtttc tgaaataacg cagccgaaag gctgc                           35

SEQ ID NO: 397           moltype = RNA  length = 36
FEATURE                  Location/Qualifiers
misc_feature             1..36
                         note = Synthetic Polynucleotide
source                   1..36
                         mol_type = other RNA
                         organism = synthetic construct
SEQUENCE: 397
cttgaatgtt aagaaatttt gcagccgaaa ggctgc                          36

SEQ ID NO: 398           moltype = RNA  length = 35
FEATURE                  Location/Qualifiers
```

```
misc_feature            1..35
                        note = Synthetic Polynucleotide
source                  1..35
                        mol_type = other RNA
                        organism = synthetic construct
SEQUENCE: 398
cttgaatgtt aagaaatttg cagccgaaag gctgc                       35

SEQ ID NO: 399          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 399
tgaatgttaa gaaattttca gcagccgaaa ggctgc                      36

SEQ ID NO: 400          moltype = RNA  length = 35
FEATURE                 Location/Qualifiers
misc_feature            1..35
                        note = Synthetic Polynucleotide
source                  1..35
                        mol_type = other RNA
                        organism = synthetic construct
SEQUENCE: 400
tgaatgttaa gaaattttcg cagccgaaag gctgc                       35

SEQ ID NO: 401          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 401
cgaggtcatt tctatggtca gcagccgaaa ggctgc                      36

SEQ ID NO: 402          moltype = RNA  length = 35
FEATURE                 Location/Qualifiers
misc_feature            1..35
                        note = Synthetic Polynucleotide
source                  1..35
                        mol_type = other RNA
                        organism = synthetic construct
SEQUENCE: 402
cgaggtcatt tctatggtcg cagccgaaag gctgc                       35

SEQ ID NO: 403          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 403
attctgtgaa ggaaaagttt gcagccgaaa ggctgc                      36

SEQ ID NO: 404          moltype = RNA  length = 35
FEATURE                 Location/Qualifiers
misc_feature            1..35
                        note = Synthetic Polynucleotide
source                  1..35
                        mol_type = other RNA
                        organism = synthetic construct
SEQUENCE: 404
attctgtgaa ggaaaagttg cagccgaaag gctgc                       35

SEQ ID NO: 405          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 405
cttggagtat ttccatcata gcagccgaaa ggctgc                      36

SEQ ID NO: 406          moltype = RNA  length = 35
```

```
FEATURE                 Location/Qualifiers
misc_feature            1..35
                        note = Synthetic Polynucleotide
source                  1..35
                        mol_type = other RNA
                        organism = synthetic construct
SEQUENCE: 406
cttggagtat ttccatcatg cagccgaaag gctgc                            35

SEQ ID NO: 407          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 407
tggagtattt ccatcatact gcagccgaaa ggctgc                           36

SEQ ID NO: 408          moltype = RNA  length = 35
FEATURE                 Location/Qualifiers
misc_feature            1..35
                        note = Synthetic Polynucleotide
source                  1..35
                        mol_type = other RNA
                        organism = synthetic construct
SEQUENCE: 408
tggagtattt ccatcatacg cagccgaaag gctgc                            35

SEQ ID NO: 409          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 409
gagtatttcc atcatactat gcagccgaaa ggctgc                           36

SEQ ID NO: 410          moltype = RNA  length = 35
FEATURE                 Location/Qualifiers
misc_feature            1..35
                        note = Synthetic Polynucleotide
source                  1..35
                        mol_type = other RNA
                        organism = synthetic construct
SEQUENCE: 410
gagtatttcc atcatactag cagccgaaag gctgc                            35

SEQ ID NO: 411          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 411
ccagcatgcc agacacctga gcagccgaaa ggctgc                           36

SEQ ID NO: 412          moltype = RNA  length = 35
FEATURE                 Location/Qualifiers
misc_feature            1..35
                        note = Synthetic Polynucleotide
source                  1..35
                        mol_type = other RNA
                        organism = synthetic construct
SEQUENCE: 412
ccagcatgcc agacacctgg cagccgaaag gctgc                            35

SEQ ID NO: 413          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 413
agaaaaagct gcatggtgaa gcagccgaaa ggctgc                           36
```

```
SEQ ID NO: 414         moltype = RNA  length = 35
FEATURE                Location/Qualifiers
misc_feature           1..35
                       note = Synthetic Polynucleotide
source                 1..35
                       mol_type = other RNA
                       organism = synthetic construct
SEQUENCE: 414
agaaaaagct gcatggtgag cagccgaaag gctgc                               35

SEQ ID NO: 415         moltype = RNA  length = 36
FEATURE                Location/Qualifiers
misc_feature           1..36
                       note = Synthetic Polynucleotide
source                 1..36
                       mol_type = other RNA
                       organism = synthetic construct
SEQUENCE: 415
tggtgaatat aagaactgaa gcagccgaaa ggctgc                              36

SEQ ID NO: 416         moltype = RNA  length = 35
FEATURE                Location/Qualifiers
misc_feature           1..35
                       note = Synthetic Polynucleotide
source                 1..35
                       mol_type = other RNA
                       organism = synthetic construct
SEQUENCE: 416
tggtgaatat aagaactgag cagccgaaag gctgc                               35

SEQ ID NO: 417         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 417
ccatcttcca aaatgcacct gg                                             22

SEQ ID NO: 418         moltype = RNA  length = 21
FEATURE                Location/Qualifiers
misc_feature           1..21
                       note = Synthetic Polynucleotide
source                 1..21
                       mol_type = other RNA
                       organism = synthetic construct
SEQUENCE: 418
catcttccaa aatgcacctg g                                              21

SEQ ID NO: 419         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 419
gccatcttcc aaaatgcacc tg                                             22

SEQ ID NO: 420         moltype = RNA  length = 21
FEATURE                Location/Qualifiers
misc_feature           1..21
                       note = Synthetic Polynucleotide
source                 1..21
                       mol_type = other RNA
                       organism = synthetic construct
SEQUENCE: 420
ccatcttcca aaatgcacct g                                              21

SEQ ID NO: 421         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 421
taccacataa ggacttcctt ct                                             22
```

```
SEQ ID NO: 422         moltype = DNA  length = 22
FEATURE                Location/Qualifiers
misc_feature           1..22
                       note = Synthetic Polynucleotide
source                 1..22
                       mol_type = other DNA
                       organism = synthetic construct
misc_feature           1..18
                       note = RNA
misc_feature           19
                       note = DNA
misc_feature           20..22
                       note = RNA
SEQUENCE: 422
taccacataa ggacttcctt ct                                            22

SEQ ID NO: 423         moltype = DNA  length = 21
FEATURE                Location/Qualifiers
misc_feature           1..21
                       note = Synthetic Polynucleotide
source                 1..21
                       mol_type = other DNA
                       organism = synthetic construct
misc_feature           1..17
                       note = RNA
misc_feature           18
                       note = DNA
misc_feature           19..21
                       note = RNA
SEQUENCE: 423
accacataag gacttccttc t                                             21

SEQ ID NO: 424         moltype = RNA  length = 21
FEATURE                Location/Qualifiers
misc_feature           1..21
                       note = Synthetic Polynucleotide
source                 1..21
                       mol_type = other RNA
                       organism = synthetic construct
SEQUENCE: 424
accacataag gacttccttc t                                             21

SEQ ID NO: 425         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 425
tccaaatatc agcatatcat tg                                            22

SEQ ID NO: 426         moltype = DNA  length = 22
FEATURE                Location/Qualifiers
misc_feature           1..22
                       note = Synthetic Polynucleotide
source                 1..22
                       mol_type = other DNA
                       organism = synthetic construct
misc_feature           1..16
                       note = RNA
misc_feature           17
                       note = DNA
misc_feature           18..22
                       note = RNA
SEQUENCE: 426
tccaaatatc agcatatcat tg                                            22

SEQ ID NO: 427         moltype = DNA  length = 21
FEATURE                Location/Qualifiers
misc_feature           1..21
                       note = Synthetic Polynucleotide
source                 1..21
                       mol_type = other DNA
                       organism = synthetic construct
misc_feature           1..15
                       note = RNA
misc_feature           16
```

```
                        note = DNA
misc_feature            17..21
                        note = RNA
SEQUENCE: 427
ccaaatatca gcatatcatt g                                                21

SEQ ID NO: 428          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 428
ccaaatatca gcatatcatt g                                                21

SEQ ID NO: 429          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 429
tgtagaaatc aatatttgct gc                                               22

SEQ ID NO: 430          moltype = DNA  length = 22
FEATURE                 Location/Qualifiers
misc_feature            1..22
                        note = Synthetic Polynucleotide
source                  1..22
                        mol_type = other DNA
                        organism = synthetic construct
misc_feature            1..12
                        note = RNA
misc_feature            13
                        note = DNA
misc_feature            14..16
                        note = RNA
misc_feature            17
                        note = DNA
misc_feature            18..22
                        note = RNA
SEQUENCE: 430
tgtagaaatc aatatttgct gc                                               22

SEQ ID NO: 431          moltype = DNA  length = 21
FEATURE                 Location/Qualifiers
misc_feature            1..21
                        note = Synthetic Polynucleotide
source                  1..21
                        mol_type = other DNA
                        organism = synthetic construct
misc_feature            1
                        note = RNA
misc_feature            2
                        note = DNA
misc_feature            3..11
                        note = RNA
misc_feature            12
                        note = DNA
misc_feature            13..15
                        note = RNA
misc_feature            16
                        note = DNA
misc_feature            17..21
                        note = RNA
SEQUENCE: 431
gtagaaatca atatttgctg c                                                21

SEQ ID NO: 432          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 432
gtagaaatca atatttgctg c                                                21
```

```
SEQ ID NO: 433          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 433
tgttatttca gaaaccgtgg tg                                            22

SEQ ID NO: 434          moltype = DNA  length = 21
FEATURE                 Location/Qualifiers
misc_feature            1..21
                        note = Synthetic Polynucleotide
source                  1..21
                        mol_type = other DNA
                        organism = synthetic construct
misc_feature            1
                        note = RNA
misc_feature            2
                        note = DNA
misc_feature            3..21
                        note = RNA
SEQUENCE: 434
gttatttcag aaaccgtggt g                                             21

SEQ ID NO: 435          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 435
gttatttcag aaaccgtggt g                                             21

SEQ ID NO: 436          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 436
aaaatttctt aacattcaag cc                                            22

SEQ ID NO: 437          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 437
aaatttctta acattcaagc c                                             21

SEQ ID NO: 438          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 438
tgaaaatttc ttaacattca ag                                            22

SEQ ID NO: 439          moltype = DNA  length = 22
FEATURE                 Location/Qualifiers
misc_feature            1..22
                        note = Synthetic Polynucleotide
source                  1..22
                        mol_type = other DNA
                        organism = synthetic construct
misc_feature            1..16
                        note = RNA
misc_feature            17
                        note = DNA
misc_feature            18..22
```

```
                        note = RNA
SEQUENCE: 439
tgaaaatttc ttaacattca ag                                    22

SEQ ID NO: 440          moltype = DNA  length = 21
FEATURE                 Location/Qualifiers
misc_feature            1..21
                        note = Synthetic Polynucleotide
source                  1..21
                        mol_type = other DNA
                        organism = synthetic construct
misc_feature            1..15
                        note = RNA
misc_feature            16
                        note = DNA
misc_feature            17..21
                        note = RNA
SEQUENCE: 440
gaaaatttct taacattcaa g                                     21

SEQ ID NO: 441          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 441
gaaaatttct taacattcaa g                                     21

SEQ ID NO: 442          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 442
tgaccataga aatgacctcg aa                                    22

SEQ ID NO: 443          moltype = DNA  length = 22
FEATURE                 Location/Qualifiers
misc_feature            1..22
                        note = Synthetic Polynucleotide
source                  1..22
                        mol_type = other DNA
                        organism = synthetic construct
misc_feature            1..12
                        note = RNA
misc_feature            13
                        note = DNA
misc_feature            14..22
                        note = RNA
SEQUENCE: 443
tgaccataga aatgacctcg aa                                    22

SEQ ID NO: 444          moltype = DNA  length = 21
FEATURE                 Location/Qualifiers
misc_feature            1..21
                        note = Synthetic Polynucleotide
source                  1..21
                        mol_type = other DNA
                        organism = synthetic construct
misc_feature            1..11
                        note = RNA
misc_feature            12
                        note = DNA
misc_feature            13..21
                        note = RNA
SEQUENCE: 444
gaccatagaa atgacctcga a                                     21

SEQ ID NO: 445          moltype = RNA  length = 21
FEATURE                 Location/Qualifiers
misc_feature            1..21
                        note = Synthetic Polynucleotide
source                  1..21
                        mol_type = other RNA
                        organism = synthetic construct
```

```
SEQUENCE: 445
gaccatagaa atgacctcga a                                            21

SEQ ID NO: 446         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 446
aaacttttcc ttcacagaat gt                                           22

SEQ ID NO: 447         moltype = RNA  length = 21
FEATURE                Location/Qualifiers
misc_feature           1..21
                       note = Synthetic Polynucleotide
source                 1..21
                       mol_type = other RNA
                       organism = synthetic construct
SEQUENCE: 447
aacttttcct tcacagaatg t                                            21

SEQ ID NO: 448         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 448
tatgatggaa atactccaag at                                           22

SEQ ID NO: 449         moltype = DNA  length = 21
FEATURE                Location/Qualifiers
misc_feature           1..21
                       note = Synthetic Polynucleotide
source                 1..21
                       mol_type = other DNA
                       organism = synthetic construct
misc_feature           1
                       note = RNA
misc_feature           2
                       note = DNA
misc_feature           3..21
                       note = RNA
SEQUENCE: 449
atgatggaaa tactccaaga t                                            21

SEQ ID NO: 450         moltype = RNA  length = 21
FEATURE                Location/Qualifiers
misc_feature           1..21
                       note = Synthetic Polynucleotide
source                 1..21
                       mol_type = other RNA
                       organism = synthetic construct
SEQUENCE: 450
atgatggaaa tactccaaga t                                            21

SEQ ID NO: 451         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 451
agtatgatgg aaatactcca ag                                           22

SEQ ID NO: 452         moltype = DNA  length = 22
FEATURE                Location/Qualifiers
misc_feature           1..22
                       note = Synthetic Polynucleotide
source                 1..22
                       mol_type = other DNA
                       organism = synthetic construct
misc_feature           1..16
                       note = RNA
misc_feature           17
```

```
                        note = DNA
misc_feature            18..22
                        note = RNA
SEQUENCE: 452
agtatgatgg aaatactcca ag                                              22

SEQ ID NO: 453          moltype = DNA  length = 21
FEATURE                 Location/Qualifiers
misc_feature            1..21
                        note = Synthetic Polynucleotide
source                  1..21
                        mol_type = other DNA
                        organism = synthetic construct
misc_feature            1
                        note = RNA
misc_feature            2
                        note = DNA
misc_feature            3..15
                        note = RNA
misc_feature            16
                        note = DNA
misc_feature            17..21
                        note = RNA
SEQUENCE: 453
gtatgatgga aatactccaa g                                               21

SEQ ID NO: 454          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 454
gtatgatgga aatactccaa g                                               21

SEQ ID NO: 455          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 455
atagtatgat ggaaatactc ca                                              22

SEQ ID NO: 456          moltype = DNA  length = 22
FEATURE                 Location/Qualifiers
misc_feature            1..22
                        note = Synthetic Polynucleotide
source                  1..22
                        mol_type = other DNA
                        organism = synthetic construct
misc_feature            1
                        note = RNA
misc_feature            2
                        note = DNA
misc_feature            3..18
                        note = RNA
misc_feature            19
                        note = DNA
misc_feature            20..22
                        note = RNA
SEQUENCE: 456
atagtatgat ggaaatactc ca                                              22

SEQ ID NO: 457          moltype = DNA  length = 21
FEATURE                 Location/Qualifiers
misc_feature            1..21
                        note = Synthetic Polynucleotide
source                  1..21
                        mol_type = other DNA
                        organism = synthetic construct
misc_feature            1..17
                        note = RNA
misc_feature            18
                        note = DNA
misc_feature            19..21
                        note = RNA
```

```
SEQUENCE: 457
tagtatgatg gaaatactcc a                                            21

SEQ ID NO: 458          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 458
tagtatgatg gaaatactcc a                                            21

SEQ ID NO: 459          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 459
tcaggtgtct ggcatgctgg ta                                           22

SEQ ID NO: 460          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 460
caggtgtctg gcatgctggt a                                            21

SEQ ID NO: 461          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 461
ttcaccatgc agctttttct tc                                           22

SEQ ID NO: 462          moltype = DNA  length = 22
FEATURE                 Location/Qualifiers
misc_feature            1..22
                        note = Synthetic Polynucleotide
source                  1..22
                        mol_type = other DNA
                        organism = synthetic construct
misc_feature            1
                        note = RNA
misc_feature            2
                        note = DNA
misc_feature            3..16
                        note = RNA
misc_feature            17
                        note = DNA
misc_feature            18..22
                        note = RNA
SEQUENCE: 462
ttcaccatgc agctttttct tc                                           22

SEQ ID NO: 463          moltype = DNA  length = 21
FEATURE                 Location/Qualifiers
misc_feature            1..21
                        note = Synthetic Polynucleotide
source                  1..21
                        mol_type = other DNA
                        organism = synthetic construct
misc_feature            1..15
                        note = RNA
misc_feature            16
                        note = DNA
misc_feature            17..21
                        note = RNA
SEQUENCE: 463
tcaccatgca gctttttctt c                                            21
```

```
SEQ ID NO: 464          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 464
tcaccatgca gctttttctt c                                    21

SEQ ID NO: 465          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 465
ttcagttctt atattcacca tg                                   22

SEQ ID NO: 466          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 466
tcagttctta tattcaccat g                                    21

SEQ ID NO: 467          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 467
ggaggcatct atactgtgat tcaga                                25

SEQ ID NO: 468          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 468
ggcatctata ctgtgattca gacaa                                25

SEQ ID NO: 469          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 469
gcatctatac tgtgattcag acaaa                                25

SEQ ID NO: 470          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 470
gtccatattt tgagcataat atgaa                                25

SEQ ID NO: 471          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
```

```
misc_feature           25
                       note = DNA
SEQUENCE: 471
atattttgag cataatatga agact                                      25

SEQ ID NO: 472         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 472
acggcttgaa tgttaagaaa ttttc                                      25

SEQ ID NO: 473         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 473
cggcttgaat gttaagaaat tttca                                      25

SEQ ID NO: 474         moltype = RNA  length = 25
FEATURE                Location/Qualifiers
misc_feature           1..25
                       note = Synthetic Polynucleotide
source                 1..25
                       mol_type = other RNA
                       organism = synthetic construct
SEQUENCE: 474
aatgttaaga aattttcagc agtgc                                      25

SEQ ID NO: 475         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
                       note = RNA
misc_feature           25
                       note = DNA
SEQUENCE: 475
tgttaagaaa ttttcagcag tgcat                                      25

SEQ ID NO: 476         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..23
                       note = RNA
misc_feature           24
                       note = DNA
misc_feature           25
                       note = RNA
SEQUENCE: 476
gttaagaaat tttcagcagt gcatg                                      25

SEQ ID NO: 477         moltype = DNA  length = 25
FEATURE                Location/Qualifiers
misc_feature           1..25
                       note = Synthetic Polynucleotide
source                 1..25
                       mol_type = other DNA
                       organism = synthetic construct
misc_feature           1..24
```

```
                        note = RNA
misc_feature            25
                        note = DNA
SEQUENCE: 477
tgcatggtga atataagaac tgaat                                     25

SEQ ID NO: 478          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 478
tgaatataag aactgaattc tacat                                     25

SEQ ID NO: 479          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 479
gaatataaga actgaattct acatg                                     25

SEQ ID NO: 480          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 480
caaagtaaga ctaattattt aaaat                                     25

SEQ ID NO: 481          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 481
aaagtaagac taattattta aaata                                     25

SEQ ID NO: 482          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
```

```
SEQUENCE: 482
agaaattgag tgaatgacaa ttttg                                   25

SEQ ID NO: 483          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 483
aaattgagtg aatgacaatt ttgta                                   25

SEQ ID NO: 484          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 484
attgagtgaa tgacaatttt gtaat                                   25

SEQ ID NO: 485          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 485
aatgacaatt ttgtaattta ggata                                   25

SEQ ID NO: 486          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 486
aagtgttttt aaaatggtga attta                                   25

SEQ ID NO: 487          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 487
agtgttttta aaatggtgaa tttaa                                   25

SEQ ID NO: 488          moltype = DNA  length = 25
FEATURE                 Location/Qualifiers
misc_feature            1..25
                        note = Synthetic Polynucleotide
```

```
source                  1..25
                        mol_type = other DNA
                        organism = synthetic construct
misc_feature            1..24
                        note = RNA
misc_feature            25
                        note = DNA
SEQUENCE: 488
cttactctgt ttatttttaa atgat                                        25

SEQ ID NO: 489          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 489
ctctgtttat ttttaaatga tcatc                                        25

SEQ ID NO: 490          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 490
tctgtttatt tttaaatgat catca                                        25

SEQ ID NO: 491          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 491
gtttattttt aaatgatcat cataa                                        25

SEQ ID NO: 492          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 492
atcatcataa tcctttgctt actat                                        25

SEQ ID NO: 493          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 493
gtgcactacc tacatttttt aaata                                        25

SEQ ID NO: 494          moltype = RNA  length = 25
FEATURE                 Location/Qualifiers
misc_feature            1..25
```

```
                     note = Synthetic Polynucleotide
source               1..25
                     mol_type = other RNA
                     organism = synthetic construct
SEQUENCE: 494
gctaggtttt tactgattat tttca                                          25

SEQ ID NO: 495       moltype = DNA  length = 25
FEATURE              Location/Qualifiers
misc_feature         1..25
                     note = Synthetic Polynucleotide
source               1..25
                     mol_type = other DNA
                     organism = synthetic construct
misc_feature         1..24
                     note = RNA
misc_feature         25
                     note = DNA
SEQUENCE: 495
ctaggttttt actgattatt ttcat                                          25

SEQ ID NO: 496       moltype = DNA  length = 25
FEATURE              Location/Qualifiers
misc_feature         1..25
                     note = Synthetic Polynucleotide
source               1..25
                     mol_type = other DNA
                     organism = synthetic construct
misc_feature         1..23
                     note = RNA
misc_feature         24..25
                     note = DNA
SEQUENCE: 496
aggtttttac tgattatttt cattt                                          25

SEQ ID NO: 497       moltype = RNA  length = 25
FEATURE              Location/Qualifiers
misc_feature         1..25
                     note = Synthetic Polynucleotide
source               1..25
                     mol_type = other RNA
                     organism = synthetic construct
SEQUENCE: 497
ctgattattt tcatttttca catgc                                          25

SEQ ID NO: 498       moltype = RNA  length = 25
FEATURE              Location/Qualifiers
misc_feature         1..25
                     note = Synthetic Polynucleotide
source               1..25
                     mol_type = other RNA
                     organism = synthetic construct
SEQUENCE: 498
atggacattt atgtcacttt tgaaa                                          25

SEQ ID NO: 499       moltype = DNA  length = 25
FEATURE              Location/Qualifiers
misc_feature         1..25
                     note = Synthetic Polynucleotide
source               1..25
                     mol_type = other DNA
                     organism = synthetic construct
misc_feature         1..24
                     note = RNA
misc_feature         25
                     note = DNA
SEQUENCE: 499
gacatttatg tcacttttga aatct                                          25

SEQ ID NO: 500       moltype = DNA  length = 25
FEATURE              Location/Qualifiers
misc_feature         1..25
                     note = Synthetic Polynucleotide
source               1..25
                     mol_type = other DNA
                     organism = synthetic construct
misc_feature         1..23
                     note = RNA
misc_feature         24
```

```
                        note = DNA
misc_feature            25
                        note = RNA
SEQUENCE: 500
acatttatgt cacttttgaa atcta                                             25

SEQ ID NO: 501          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 501
tagaattgat gttgtaatta atgca                                             25

SEQ ID NO: 502          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 502
agaattgatg ttgtaattaa tgcaa                                             25

SEQ ID NO: 503          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 503
gaattgatgt tgtaattaat gcaag                                             25

SEQ ID NO: 504          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 504
accatcttac tgtaacattt ttcta                                             25

SEQ ID NO: 505          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 505
catcttactg taacattttt ctatt                                             25

SEQ ID NO: 506          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 506
tcttactgta acatttttct attgt                                             25
```

```
SEQ ID NO: 507          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 507
cttactgtaa catttttcta ttgtt                                        25

SEQ ID NO: 508          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24..25
                        note = DNA
SEQUENCE: 508
ttactgtaac atttttctat tgttt                                        25

SEQ ID NO: 509          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 509
actgtaacat ttttctattg tttaa                                        25

SEQ ID NO: 510          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 510
ctgtaacatt tttctattgt ttaaa                                        25

SEQ ID NO: 511          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..24
                        note = RNA
misc_feature            25
                        note = DNA
SEQUENCE: 511
tgtaacattt ttctattgtt taaat                                        25

SEQ ID NO: 512          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 512
gtaacatttt tctattgttt aaata                                        25
```

```
SEQ ID NO: 513          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 513
taacattttt ctattgttta aatag                                          25

SEQ ID NO: 514          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 514
aacattttc tattgtttaa ataga                                           25

SEQ ID NO: 515          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 515
acatttttct attgtttaaa tagaa                                          25

SEQ ID NO: 516          moltype = RNA  length = 25
FEATURE                 Location/Qualifiers
misc_feature            1..25
                        note = Synthetic Polynucleotide
source                  1..25
                        mol_type = other RNA
                        organism = synthetic construct
SEQUENCE: 516
catttttcta ttgtttaaat agaaa                                          25

SEQ ID NO: 517          moltype = DNA  length = 25
FEATURE                 Location/Qualifiers
misc_feature            1..25
                        note = Synthetic Polynucleotide
source                  1..25
                        mol_type = other DNA
                        organism = synthetic construct
misc_feature            1..23
                        note = RNA
misc_feature            24
                        note = DNA
misc_feature            25
                        note = RNA
SEQUENCE: 517
gtcaatcttc atagatgata acttg                                          25

SEQ ID NO: 518          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 518
tctgaatcac agtatagatg cctccaa                                        27

SEQ ID NO: 519          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 519
ttgtctgaat cacagtatag atgcctc                                        27

SEQ ID NO: 520          moltype = RNA  length = 27
FEATURE                 Location/Qualifiers
misc_feature            1..27
```

```
                        note = Synthetic Polynucleotide
source                  1..27
                        mol_type = other RNA
                        organism = synthetic construct
SEQUENCE: 520
tttgtctgaa tcacagtata gatgcct                                          27

SEQ ID NO: 521          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 521
ttcatattat gctcaaaata tggacct                                          27

SEQ ID NO: 522          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 522
agtcttcata ttatgctcaa aatatgg                                          27

SEQ ID NO: 523          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 523
gaaaatttct taacattcaa gccgttt                                          27

SEQ ID NO: 524          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 524
tgaaaatttc ttaacattca agccgtt                                          27

SEQ ID NO: 525          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 525
gcactgctga aaatttctta acattca                                          27

SEQ ID NO: 526          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 526
atgcactgct gaaaatttct taacatt                                          27

SEQ ID NO: 527          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 527
catgcactgc tgaaaatttc ttaacat                                          27

SEQ ID NO: 528          moltype = RNA  length = 27
FEATURE                 Location/Qualifiers
```

```
misc_feature           1..27
                       note = Synthetic Polynucleotide
source                 1..27
                       mol_type = other RNA
                       organism = synthetic construct
SEQUENCE: 528
attcagttct tatattcacc atgcagc                                        27

SEQ ID NO: 529         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 529
atgtagaatt cagttcttat attcacc                                        27

SEQ ID NO: 530         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 530
catgtagaat tcagttctta tattcac                                        27

SEQ ID NO: 531         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 531
attttaaata attagtctta ctttgct                                        27

SEQ ID NO: 532         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 532
tattttaaat aattagtctt actttgc                                        27

SEQ ID NO: 533         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 533
caaaattgtc attcactcaa tttcttc                                        27

SEQ ID NO: 534         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 534
tacaaaattg tcattcactc aatttct                                        27

SEQ ID NO: 535         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 535
attacaaaat tgtcattcac tcaattt                                        27

SEQ ID NO: 536         moltype = RNA  length = 27
```

```
FEATURE                Location/Qualifiers
misc_feature           1..27
                       note = Synthetic Polynucleotide
source                 1..27
                       mol_type = other RNA
                       organism = synthetic construct
SEQUENCE: 536
tatcctaaat tacaaaattg tcattca                                        27

SEQ ID NO: 537         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 537
taaattcacc attttaaaaa cactttt                                        27

SEQ ID NO: 538         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 538
ttaaattcac cattttaaaa acacttt                                        27

SEQ ID NO: 539         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 539
atcatttaaa aataaacaga gtaagag                                        27

SEQ ID NO: 540         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 540
gatgatcatt taaaaataaa cagagta                                        27

SEQ ID NO: 541         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 541
tgatgatcat ttaaaaataa acagagt                                        27

SEQ ID NO: 542         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 542
ttatgatgat catttaaaaa taaacag                                        27

SEQ ID NO: 543         moltype = RNA  length = 27
FEATURE                Location/Qualifiers
misc_feature           1..27
                       note = Synthetic Polynucleotide
source                 1..27
                       mol_type = other RNA
                       organism = synthetic construct
SEQUENCE: 543
atagtaagca aaggattatg atgatca                                        27
```

```
SEQ ID NO: 544          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 544
tatttaaaaa atgtaggtag tgcacat                                       27

SEQ ID NO: 545          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 545
tgaaaataat cagtaaaaac ctagcta                                       27

SEQ ID NO: 546          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 546
atgaaaataa tcagtaaaaa cctagct                                       27

SEQ ID NO: 547          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 547
aaatgaaaat aatcagtaaa aacctag                                       27

SEQ ID NO: 548          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 548
gcatgtgaaa aatgaaaata atcagta                                       27

SEQ ID NO: 549          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 549
tttcaaaagt gacataaatg tccatta                                       27

SEQ ID NO: 550          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 550
agatttcaaa agtgacataa atgtcca                                       27

SEQ ID NO: 551          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 551
tagatttcaa aagtgacata aatgtcc                                       27
```

```
SEQ ID NO: 552          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 552
tgcattaatt acaacatcaa ttctaga                                          27

SEQ ID NO: 553          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 553
ttgcattaat tacaacatca attctag                                          27

SEQ ID NO: 554          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 554
cttgcattaa ttacaacatc aattcta                                          27

SEQ ID NO: 555          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 555
tagaaaaatg ttacagtaag atggtgg                                          27

SEQ ID NO: 556          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 556
aatagaaaaa tgttacagta agatggt                                          27

SEQ ID NO: 557          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 557
acaatagaaa aatgttacag taagatg                                          27

SEQ ID NO: 558          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 558
aacaatagaa aaatgttaca gtaagat                                          27

SEQ ID NO: 559          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 559
```

```
aaacaataga aaaatgttac agtaaga                                          27

SEQ ID NO: 560          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 560
ttaaacaata gaaaaatgtt acagtaa                                          27

SEQ ID NO: 561          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 561
tttaaacaat agaaaaatgt tacagta                                          27

SEQ ID NO: 562          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 562
atttaaacaa tagaaaaatg ttacagt                                          27

SEQ ID NO: 563          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 563
tatttaaaca atagaaaaat gttacag                                          27

SEQ ID NO: 564          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 564
ctatttaaac aatagaaaaa tgttaca                                          27

SEQ ID NO: 565          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 565
tctatttaaa caatagaaaa atgttac                                          27

SEQ ID NO: 566          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 566
ttctatttaa acaatagaaa aatgtta                                          27

SEQ ID NO: 567          moltype = RNA  length = 27
FEATURE                 Location/Qualifiers
misc_feature            1..27
                        note = Synthetic Polynucleotide
source                  1..27
                        mol_type = other RNA
                        organism = synthetic construct
```

```
SEQUENCE: 567
tttctattta aacaatagaa aaatgtt                                    27

SEQ ID NO: 568          moltype = RNA  length = 27
FEATURE                 Location/Qualifiers
misc_feature            1..27
                        note = Synthetic Polynucleotide
source                  1..27
                        mol_type = other RNA
                        organism = synthetic construct
SEQUENCE: 568
caagttatca tctatgaaga ttgacca                                    27

SEQ ID NO: 569          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 569
ggcatctata ctgtgattca gcagccgaaa ggctgc                          36

SEQ ID NO: 570          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 570
gcatctatac tgtgattcag gcagccgaaa ggctgc                          36

SEQ ID NO: 571          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 571
gcagcaaata ttgatttcta gcagccgaaa ggctgc                          36

SEQ ID NO: 572          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 572
ctgaaataac agcaatagaa gcagccgaaa ggctgc                          36

SEQ ID NO: 573          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 573
acggcttgaa tgttaagaaa gcagccgaaa ggctgc                          36

SEQ ID NO: 574          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 574
agtgttttta aaatggtgaa gcagccgaaa ggctgc                          36

SEQ ID NO: 575          moltype = RNA  length = 22
FEATURE                 Location/Qualifiers
misc_feature            1..22
                        note = Synthetic Polynucleotide
source                  1..22
                        mol_type = other RNA
```

```
                         organism = synthetic construct
SEQUENCE: 575
tgaatcacag tatagatgcc gg                                              22

SEQ ID NO: 576           moltype = RNA  length = 22
FEATURE                  Location/Qualifiers
misc_feature             1..22
                         note = Synthetic Polynucleotide
source                   1..22
                         mol_type = other RNA
                         organism = synthetic construct
SEQUENCE: 576
ctgaatcaca gtatagatgc gg                                              22

SEQ ID NO: 577           moltype = RNA  length = 22
FEATURE                  Location/Qualifiers
misc_feature             1..22
                         note = Synthetic Polynucleotide
source                   1..22
                         mol_type = other RNA
                         organism = synthetic construct
SEQUENCE: 577
tagaaatcaa tatttgctgc gg                                              22

SEQ ID NO: 578           moltype = RNA  length = 22
FEATURE                  Location/Qualifiers
misc_feature             1..22
                         note = Synthetic Polynucleotide
source                   1..22
                         mol_type = other RNA
                         organism = synthetic construct
SEQUENCE: 578
ttctattgct gttatttcag gg                                              22

SEQ ID NO: 579           moltype = RNA  length = 22
FEATURE                  Location/Qualifiers
misc_feature             1..22
                         note = Synthetic Polynucleotide
source                   1..22
                         mol_type = other RNA
                         organism = synthetic construct
SEQUENCE: 579
tttcttaaca ttcaagccgt gg                                              22

SEQ ID NO: 580           moltype = RNA  length = 22
FEATURE                  Location/Qualifiers
misc_feature             1..22
                         note = Synthetic Polynucleotide
source                   1..22
                         mol_type = other RNA
                         organism = synthetic construct
SEQUENCE: 580
ttcaccattt taaaaacact gg                                              22

SEQ ID NO: 581           moltype = RNA  length = 35
FEATURE                  Location/Qualifiers
misc_feature             1..35
                         note = Synthetic Polynucleotide
source                   1..35
                         mol_type = other RNA
                         organism = synthetic construct
SEQUENCE: 581
gaatgttaag aaattttcag cagccgaaag gctgc                                35

SEQ ID NO: 582           moltype = RNA  length = 36
FEATURE                  Location/Qualifiers
misc_feature             1..36
                         note = Synthetic Polynucleotide
source                   1..36
                         mol_type = other RNA
                         organism = synthetic construct
SEQUENCE: 582
tgcatgagtt tcaaaatcta gcagccgaaa ggctgc                               36

SEQ ID NO: 583           moltype = RNA  length = 36
FEATURE                  Location/Qualifiers
misc_feature             1..36
                         note = Synthetic Polynucleotide
source                   1..36
```

```
                        mol_type = other RNA
                        organism = synthetic construct
SEQUENCE: 583
tcgagatgat ctaacaatta gcagccgaaa ggctgc                            36

SEQ ID NO: 584          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 584
agactaatta tttaaaataa gcagccgaaa ggctgc                            36

SEQ ID NO: 585          moltype = RNA  length = 36
FEATURE                 Location/Qualifiers
misc_feature            1..36
                        note = Synthetic Polynucleotide
source                  1..36
                        mol_type = other RNA
                        organism = synthetic construct
SEQUENCE: 585
agaattgatg ttgtaattaa gcagccgaaa ggctgc                            36

SEQ ID NO: 586          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 586
taaatttctt aacattcaag gg                                           22

SEQ ID NO: 587          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 587
aaatttctta acattcaagg g                                            21

SEQ ID NO: 588          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 588
ttcaccatgc agctttttct gg                                           22

SEQ ID NO: 589          moltype = RNA  length = 21
FEATURE                 Location/Qualifiers
misc_feature            1..21
                        note = Synthetic Polynucleotide
source                  1..21
                        mol_type = other RNA
                        organism = synthetic construct
SEQUENCE: 589
tcaccatgca gctttttctg g                                            21

SEQ ID NO: 590          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 590
tgaaaatttc ttaacattca gg                                           22

SEQ ID NO: 591          moltype = RNA  length = 22
FEATURE                 Location/Qualifiers
misc_feature            1..22
                        note = Synthetic Polynucleotide
```

```
source                1..22
                      mol_type = other RNA
                      organism = synthetic construct
SEQUENCE: 591
ttcagttctt atattcacca gg                                              22

SEQ ID NO: 592        moltype = RNA  length = 22
FEATURE               Location/Qualifiers
misc_feature          1..22
                      note = Synthetic Polynucleotide
source                1..22
                      mol_type = other RNA
                      organism = synthetic construct
SEQUENCE: 592
aaaatttctt aacattcaag gg                                              22

SEQ ID NO: 593        moltype = RNA  length = 21
FEATURE               Location/Qualifiers
misc_feature          1..21
                      note = Synthetic Polynucleotide
source                1..21
                      mol_type = other RNA
                      organism = synthetic construct
SEQUENCE: 593
tgaaaatttc ttaacattcg g                                               21

SEQ ID NO: 594        moltype = RNA  length = 22
FEATURE               Location/Qualifiers
misc_feature          1..22
                      note = Synthetic Polynucleotide
source                1..22
                      mol_type = other RNA
                      organism = synthetic construct
SEQUENCE: 594
tagattttga aactcatgca gg                                              22

SEQ ID NO: 595        moltype = RNA  length = 22
FEATURE               Location/Qualifiers
misc_feature          1..22
                      note = Synthetic Polynucleotide
source                1..22
                      mol_type = other RNA
                      organism = synthetic construct
SEQUENCE: 595
taattgttag atcatctcga gg                                              22

SEQ ID NO: 596        moltype = RNA  length = 22
FEATURE               Location/Qualifiers
misc_feature          1..22
                      note = Synthetic Polynucleotide
source                1..22
                      mol_type = other RNA
                      organism = synthetic construct
SEQUENCE: 596
ttattttaaa taattagtct gg                                              22

SEQ ID NO: 597        moltype = RNA  length = 22
FEATURE               Location/Qualifiers
misc_feature          1..22
                      note = Synthetic Polynucleotide
source                1..22
                      mol_type = other RNA
                      organism = synthetic construct
SEQUENCE: 597
ttaattacaa catcaattct gg                                              22

SEQ ID NO: 598        moltype = DNA  length = 22
FEATURE               Location/Qualifiers
misc_feature          1..22
                      note = Synthetic Polynucleotide
source                1..22
                      mol_type = other DNA
                      organism = synthetic construct
misc_feature          1
                      note = RNA
misc_feature          2
                      note = DNA
misc_feature          3..22
                      note = RNA
```

```
SEQUENCE: 598
ttcagttctt atattcacca tg                                        22

SEQ ID NO: 599          moltype = DNA  length = 40
FEATURE                 Location/Qualifiers
source                  1..40
                        mol_type = unassigned DNA
                        organism = Homo sapiens
SEQUENCE: 599
gatagaagga agtccttatg tggtactttt tgacataggc                     40

SEQ ID NO: 600          moltype = DNA  length = 48
FEATURE                 Location/Qualifiers
source                  1..48
                        mol_type = unassigned DNA
                        organism = Homo sapiens
SEQUENCE: 600
gaccgagaag ccaatgatat gctgatattt ggatctttaa ctgcctgg            48

SEQ ID NO: 601          moltype = DNA  length = 37
FEATURE                 Location/Qualifiers
source                  1..37
                        mol_type = unassigned DNA
                        organism = Homo sapiens
SEQUENCE: 601
tccaaacggc ttgaatgtta agaaattttc agcagtg                        37

SEQ ID NO: 602          moltype = DNA  length = 37
FEATURE                 Location/Qualifiers
source                  1..37
                        mol_type = unassigned DNA
                        organism = Homo sapiens
SEQUENCE: 602
ttgttcgagg tcatttctat ggtcatctcg actttga                        37

SEQ ID NO: 603          moltype = DNA  length = 56
FEATURE                 Location/Qualifiers
source                  1..56
                        mol_type = unassigned DNA
                        organism = Homo sapiens
SEQUENCE: 603
tgcacattct gtgaaggaaa agtttggaaa aaaactctat gatgcattat taagag   56

SEQ ID NO: 604          moltype = DNA  length = 43
FEATURE                 Location/Qualifiers
source                  1..43
                        mol_type = unassigned DNA
                        organism = Homo sapiens
SEQUENCE: 604
aagctgcatg gtgaatataa gaactgaatt ctacatgtgc tgc                 43

SEQ ID NO: 605          moltype = DNA  length = 47
FEATURE                 Location/Qualifiers
source                  1..47
                        mol_type = unassigned DNA
                        organism = Homo sapiens
SEQUENCE: 605
gtggaagaaa ttgagtgaat gacaattttg taatttagga taagatc             47

SEQ ID NO: 606          moltype = DNA  length = 39
FEATURE                 Location/Qualifiers
source                  1..39
                        mol_type = unassigned DNA
                        organism = Homo sapiens
SEQUENCE: 606
tttctcttac tctgtttatt tttaaatgat catcataat                      39

SEQ ID NO: 607          moltype = DNA  length = 44
FEATURE                 Location/Qualifiers
source                  1..44
                        mol_type = unassigned DNA
                        organism = Homo sapiens
SEQUENCE: 607
tagctaggtt tttactgatt attttcattt ttcacatgca tcag                44

SEQ ID NO: 608          moltype = DNA  length = 37
FEATURE                 Location/Qualifiers
source                  1..37
                        mol_type = unassigned DNA
```

```
                        organism = Homo sapiens
SEQUENCE: 608
tcttactgta acatttttct attgtttaaa tagaaag                          37

SEQ ID NO: 609          moltype = DNA  length = 3132
FEATURE                 Location/Qualifiers
source                  1..3132
                        mol_type = unassigned DNA
                        organism = Homo sapiens
SEQUENCE: 609
agatactgac agggcagata ccgtcctcac aatacctgcc cagaaagacg agaaagagga  60
ggaagaattc ctccttccac caggaattct gtgggaagca cataagattt catgctacta  120
gtttattccc aagagaagct accaaagcct ggtaactcta ccaactctaa cttttgtgcc  180
tgtaagttct cttctcctgg gattacaact aattgaaaca ggaattcaaa ggagtctcgg  240
aggactgtaa gaagaatgct tcgaggccga tccctctctg taacatccct gggtgggctt  300
ccccagtggg aagtcgaaga acttcctgtg gaggagttac tgctctttga agttgcttgg  360
gaagtgacca ataaagttgg aggcatctat actgtgattc agacaaaggc caaaacaaca  420
gcagatgaat ggggagagaa ctattttctg ataggtccat attttgagca taatatgaag  480
actcaggtgg aacagtgtga acctgtaaat gatgctgtca gaagagcagt ggacgcaatg  540
aataagcatg gctgccaggt gcattttgga agatggctga tagaaggaag tccttatgtg  600
gtacttttg acataggcta ttcagcttgg aatctggaca ggtggaaggg tgacctctgg  660
gaagcatgca gtgtcggcat tccttatcat gaccgagaag ccaatgatat gctgatattt  720
ggatctttaa ctgcctggtt cttaaaagag gtgacagatc atgcagatgg taaatatgtc  780
gttgcccaat tccatgaatg gcaggctgga attggactga tcctttctcg agccaggaaa  840
cttcctattg ccacaatatt tacaacccac gctacactac ttgggaggta tctctgtgca  900
gcaaatattg atttctacaa ccatcttgat aagtttaaca ttgacaaaga ggctggggaa  960
aggcagattt accaccggta ctgcatggag cgagcttccg ttcattgcgc tcacgtgttc  1020
accacggttt ctgaaataac agcaatagaa gctgaacata tgctgaagag aaagcctgat  1080
gtagttactc caaacggctt gaatgttaag aaattttcag cagtgcatga gtttcaaaat  1140
ctacatgcca tgtacaaggc cagaatccaa gattttgttc gaggtcattt ctatggtcat  1200
ctcgactttg atcttgaaaa gactttgttc cttttcattg ctgggaggta tgagttttca  1260
aacaaaggag ctgacatctt cctagaatcc ttatccaggc taaatttcct gctgaggatg  1320
cataaaagtg acatcacagt gatggtgttt ttcattatgc ctgccaagac aaataatttc  1380
aacgtggaaa ccctgaaagg acaagcagtg cgaaaacagc tgtgggatgt tgcacattct  1440
gtgaaggaaa agtttggaaa aaaactctat gatgcattat taagaggaga aattcctgac  1500
ctgaacgata ttttagatcg agatgatcta acaattatga aaagagccat cttttcaact  1560
cagcgacagt cattgccccc agtgaccacg cacaacatga ttgatgactc caccgacccc  1620
atcctcagca ccattagacg gattggactt ttcaacaacc gcacagatag agtcaaggtg  1680
attttgcacc cagagtttct atcctccacc agtcccttac tacccatgga ctatgaagag  1740
tttgttagag gttgtcatct tggagtattt ccatcatact atgaaccctg ggttatact   1800
ccagctgaat gcactgtgat gggtatcccc agtgtgacca cgaatctctc cgggtttggc  1860
tgtttcatgc aggagcacgt ggctgatcct actgcttacg gtatttacat cgttgacagg  1920
cggttccgtt ctccagatga ttcttgcaat cagctgacta agtttctcta tggattttgc  1980
aaacagtcac gccgccaaag gattatccag aggaacagaa ctgagaggct ctcagatctt  2040
ctggattgga gatacttagg cagatattac cagcatgcca gacacctgac attaagcaga  2100
gcttttccag ataaattcca tgtggaacta acatcaccac caacgacaga aggatttaaa  2160
tatcccaggc cttcctcagt accaccttct ccttcagggt ctcaggcctc cagtcctcag  2220
agcagtgatg tggaagatga agtggaggat gagagatacg atgaggaaga ggaggctgaa  2280
agggatcggt taaatatcaa gtcaccattt tcactgagcc acgttcctca tgggaagaaa  2340
aagctgcatg gtgaatataa gaactgaatt ctacatgtgc tgcatgaaga gctaatttaa  2400
aaaagcaaag taagactaat tatttaaaat aaaaatgcca caaatttcat ttctccttc  2460
taagtattac aatggagttt attctctgcc taaaaagtgg aagaaattga gtgaatgaca  2520
attttgtaat ttaggataag atccaagtta ttttccccaa ctcttgtttc ccccataaag  2580
ttaggcatga ggaggagcac tcattaaagg cagaagacgg aaaagtgttt ttaaaatggt  2640
gaatttaagt ggtaaggatt ttctcttact ctgtttattt ttaaatgatc atcataatcc  2700
tttgcttact atttatgcag cttctctacc ccaccacaca aatttcccat ttcccccccg  2760
aaaaccttga tcttacccat gaatgtgcac tacctacatt ttttaaatag ctaggttttt  2820
actgattatt ttcatttttc acatgcatca gaaccatgat ttagatgtag ttttgcagag  2880
acaaaaatcc atgagtgaat agctatccta agtccatatt ttgatgcata ttaatggaca  2940
tttatgtcac ttttgaaatc tagaattgat gttgtaatta atgcaagata ttaccatgta  3000
catggtacca ccatcttact gtaacatttt tctattgttt aaatagaaag ccttttttaaa 3060
atttggtcaa tcttcataga tgataacttg taaaatccaa gtaaataaac acattaatat  3120
ttaataactt aa                                                     3132

SEQ ID NO: 610          moltype = DNA  length = 3149
FEATURE                 Location/Qualifiers
source                  1..3149
                        mol_type = unassigned DNA
                        organism = Macaca mulatta
SEQUENCE: 610
agatactggt agggcagaaa cttcctaaca atacctgccc agaaagacgg gaaagaggag  60
gaaaaattcc tctttccacc aggaattctc tgggaagcac ataggatttc acgctactag  120
tttattccca agagaagcta ccaaagcttg gtaactacca actcttaact tttgtgtctc  180
taagtacact tctcctggga ttacaacaaa ttgaaccagg gatttaacgg aatctcagag  240
gaccgtaaga agaatgcttc gaggccgatc cctgtctgta acatccctga gtgggctgcc  300
ccggtgggaa gtcaaagaac ttcctgtgga ggagttactg ctctttgaag ttgcttggga  360
ggtgaccaat aaagttggag gcatctatac tgtgattcag acaaaggcca aaacaacagc  420
agatgaatgg ggagacaact attttctgat aggtccatat tttgagcata atatgaagac  480
tcaggtggaa caatgtgaac ctgtaaatga tgctgtcaga agagcagtgg atgcaatgaa  540
```

```
taagcatggc tgccaggtgc attttggaag atggctgata gaaggaagtc cttatgtggt  600
actttttgac ataggctttt cagcttggaa tctggatagg tggaagggtg acctctggga  660
agcatgcagt gtcggcattc cttatcatga ccgagaagcc aatgatatgc tgatatttgg  720
atctttaact gcctggttct taaaagaggt gacagatcac gcagatgata aacatgtcgt  780
tgcccaattc catgaatggc aggctggaat tggactgatc ctttctcgag ccaggaaact  840
tcctattgcc acaatattta caacccacgc tacactactc gggaggtatc tctgtgcagc  900
aaatattgat ttctacaacc atcttgataa gtttaacata gacaaagagg ctggggaaag  960
gcagatttac caccggtact gcatggagcg agcctccgtt cattgcgctc atgtgttcac  1020
cacggtttct gaaataacag caatagaggc cgaacacatg ctgaagagaa agcctgatgt  1080
agttactcca aatggcttga atgttaagaa attttcagca gtgcatgagt ttcaaaatct  1140
acatgccatg tacaaggcca gaatccaaga ttttgttcga ggtcatttct atggtcatct  1200
ggactttgat cttgaaaaga ctttgttcct tttcattgct gggagatatg agttttcaaa  1260
caaaggagct gacatcttcc tagaatcctt atccaggcta aatttcctgc tgaggatgca  1320
taaaagtgac gtcacagtgg tggtgttttt cattatgcct gccaagacaa ataatttcaa  1380
cgtggaaacc ctgaaaggac aagcagtgcg aaaacaactg tgggacattg cacattctgt  1440
gaaggaaaag tttggaaaaa aactctatga tgcattatta agaggagaaa ttcctgacat  1500
gaacaatatt ttagatcgag atgatctaac aattatgaaa agagccatct tttcaactca  1560
gcgacagtca ttgcccccag tgaccacgca caacatgatt gatgactcca ccgaccccat  1620
cctcagcacc attagacgga tcggactttt caacaaccgc acagacagag tcaaggtgat  1680
tttgcacccg gaatttctat cctccaccag tcccctacta cccatggact atgaagagtt  1740
cgtcagaggt tgtcaccttg gagtatttcc atcatactat gaaccctggg gttatactcc  1800
agctgaatgc acagtgatgg gtatccccag tgtgaccacg aatctctccg ggtttggctg  1860
tttcatgcag gagcatgtgg ctgatcctac tgcttacggt atttacatcg ttgacaggcg  1920
gttccgttct ccagatgatt cttgcaatca gctgactcag tttctttatg gatttgcaa  1980
acagtcacgc cgccaaagga ttatccagag gaacagaact gagaggctct cagatcttct  2040
ggattggaga tacttaggca gatattacca gcatgccaga cacctgacat taagcagagc  2100
ttttccagat aaattccatg tggaactaac atcaccacca atgacagaag gatttaaata  2160
tcccaggcct tcctcagtac caccttctcc ttcagggtct caggcctcca gtcctcagag  2220
cagtgatgtg gaagacgaag tggaggatga gagatacgat gaggaaaagg aggctgaaag  2280
ggatcggtta aatatcaagt caccatttgc actgagccac gttcctcgtg ggaagaaaaa  2340
gctgcatggt gaatataaga actgaattct acatgtgctg agaagagcta atttcataaa  2400
gcaaagtaag actaattatt taaaataaaa atgccacaca tttcattttc tccttctaag  2460
tattacaatg gaatttatta tctgcctaaa aagtggaaga aattgagtga atgacaattt  2520
cataatttag aataagatcc aagttgtttt ccccaactct tgttttcccc gtaaaagtta  2580
ggcatgagga ggagcactca ttaaaggcag aagatggaaa agtgttttta aaatggtgaa  2640
tttaagtggt aaggatttc tcttactctg tttattttta aattatcacc ataatccttt  2700
gcttactatt tatgcagctt ctctacccca ccacacaaat ttctcatttc cctctgaaaa  2760
ccttgatctt tcccatgaat gtgcactacc tacatatttt aaatagctag atttttactg  2820
attattttca tttttcacat gcatcagaac catgatttat atgtagtgtt gcagagacaa  2880
aatccatgtg tgaacagcta tcctaagttc atattttgat gcatactaat gcacatttat  2940
gtcacttttg aactctagaa tttatgttgt aattaatgga agatattatc atgtgaatgg  3000
aagatattac catgtgcatg gtaccaacat cttactgtaa catttttcta ttgtttaaat  3060
agaaagactt taaaaaaatt tggtcaatct tcatagatga taagttgtta aatcccagta  3120
aataaatgca ttaatattta ataacttaa                                  3149

SEQ ID NO: 611         moltype = DNA  length = 2671
FEATURE                Location/Qualifiers
source                 1..2671
                       mol_type = unassigned DNA
                       organism = Mus musculus
SEQUENCE: 611
tcatgctcag tctgtcctct ggctacctgc cctgctgtga atagtcaggt ttcagctgcg  60
attttttgtt ttgttttgtc ttgttttttt tgtttttggg tgtctgtgtg gattataact  120
gtgaggcact gccctctcct gaaaggcagc aaggagctgg gcacgcttca tccagctgcg  180
ctgggttcat gtgacctcag attgctggct caccctgtag aggctatccc aaggctgctg  240
ctttttctca gtgctgactg cagtcagctg aatcaggtcc caaacggcac cacacagctg  300
gaagaagaat gctcagaggc cgctccttgt cggtgacatc ccttggtggg ctccctgtgt  360
gggaagctga aagactccct gtggaagact tactgctttt tgaagtttct tgggaggtga  420
ccaacaaagt tgggggcatc tgtactgtga tccagaccaa ggccaaaacg acagccgatg  480
agtggggaga gaattacttc ctgataggtc cgtactttga gcataaatatg aagactcaag  540
tagaacaatg tgagcccacc aacgatgctg tcagaaaagc tgtggatgcg atgaataaac  600
atggctgcca ggtgcatttt ggaagatggc tcatagaagg gagtccctac gtggtgctct  660
ttgacatcag ctcctcagca tggaacctgg acagatggaa gggtgacttc tgggaagctt  720
gtggcgttgg catccctcat catgaccgag aagctaacga catgctcata tttgggtctt  780
taactgcctg gttcttaaag gaggtgacag accacgcaga cggtaaacac gtcattgccc  840
aattccatga atggcaggct gggactgggc tgatcctttc tcgtgccagg aaactcccca  900
ttgccacagt atttacaacc catgccacac tgcttgggcg ttatctctgt gcagcaaata  960
ttgacttcta caaccagctt gacaagttcg acattgacaa agaggccggg gagaggcaga  1020
tataccaccg ctactgcatg gagcgggcat ccgtgcactg tgcgcacgtg ttcaccacag  1080
tgtcagaaat cacagccatc gaggcagagc acatgctgaa gaggaagcct gatgtagtga  1140
ctccaaatgg tttgaatgtt aagaagtttt ctgcagtgca tgaatttcaa aatctccacg  1200
ccatgtacaa ggccaggata caggatttcg ttcgaggtca tttctatggt catctggact  1260
ttgatcttga gaagacttta ttcctcttca ttgctgggag atatgaattc tcaaacaaag  1320
gagcagacat cttcctggag tccttatcca ggcttaattt cctcctgagg atgcataaga  1380
gtaacgtcac cgtggtagtg tttttcatca tgcctgccaa gacaaacaat ttcaacgtgg  1440
aaaccctgaa gggccaggca gtgcggaaac agctgtggga cactgtgcat tgtttgaagg  1500
agaagtttgg gaagaaactc tatgacgggt tattaagagg agaaattcct gacatgaata  1560
gtatttgga tcgagatgac ttaacaatta tgaaaagggc catttttca actcagagac  1620
agtctttgcc tcctgtgacc actcacaata tgatcgatga ttccacggat cccatcctca  1680
```

-continued

```
gcaccattag acgaatcgga cttttcaaca atcgtgcaga cagagtcaag gtgattttac  1740
acccagaatt cctgtcctcc accagccctc tattgcccat ggattatgaa gagtttgtcc  1800
gaggttgtca ccttggggtg tttccatcgt actatgaacc ctggggttac acaccagctg  1860
aatgcacagt gatgggcatc cccagtgtga ctacaaacct ctccggtttt gggtgtttcg  1920
tgcaggagca tgtggctgac cctactgcat acggtattta catcgtggac agacgcttcc  1980
gctctccaga cgattcttgc aaccagctga ctcagttcct ctacgggttt tgtaaacagt  2040
cacgccggca aaggatcatt cagaggaacc gcacggagag gctctcagat ctcctggact  2100
ggagatacct gggcagatat taccagcatg ccagacacct gacactgagc agggcttttc  2160
cagacaaatt ccacctagag cccacatcac caccaacgac ggatggcttt aagtatccca  2220
ggccctcctc agtaccacct tctccgtcag gatcccaggc ctccagtcct cagtgcagtg  2280
atgcggaaga cgaagaagat gaggatgaga ggtatgatga ggaagaggag gctgagaggg  2340
atcggctaaa tatcaagtca ccgttttctc tgaaccactt tccaaagggg aagaaaaagc  2400
ttcatggaga atataagaac tgactgagct caaacgaaat gattcagaat ccacaagaaa  2460
atgagctgcc ccaagtccac accctgatgc agaccaacag atatttacat cctgacatct  2520
gaaatctaga atttgtatcc agatcattga taggaacttg tagccaccaa tgtgagtcac  2580
cttactgtaa cggtactttt gttgtctaat tggaaatttc aatctgttag agataataaa  2640
ttgccaaatt caaatgaaaa aaaaaaaaaa a                                 2671

SEQ ID NO: 612         moltype = RNA  length = 36
FEATURE                Location/Qualifiers
misc_feature           1..36
                       note = Synthetic Polynucleotide
source                 1..36
                       mol_type = other RNA
                       organism = synthetic construct
SEQUENCE: 612
tgggaggtat gagttttcaa gcagccgaaa ggctgc                            36

SEQ ID NO: 613         moltype = RNA  length = 36
FEATURE                Location/Qualifiers
misc_feature           1..36
                       note = Synthetic Polynucleotide
source                 1..36
                       mol_type = other RNA
                       organism = synthetic construct
SEQUENCE: 613
aggaaaagtt tggaaaaaaa gcagccgaaa ggctgc                            36

SEQ ID NO: 614         moltype = RNA  length = 36
FEATURE                Location/Qualifiers
misc_feature           1..36
                       note = Synthetic Polynucleotide
source                 1..36
                       mol_type = other RNA
                       organism = synthetic construct
SEQUENCE: 614
tggtcaatct tcatagatga gcagccgaaa ggctgc                            36

SEQ ID NO: 615         moltype = RNA  length = 36
FEATURE                Location/Qualifiers
misc_feature           1..36
                       note = Synthetic Polynucleotide
source                 1..36
                       mol_type = other RNA
                       organism = synthetic construct
SEQUENCE: 615
ggtttctgaa ataacagcaa gcagccgaaa ggctgc                            36

SEQ ID NO: 616         moltype = RNA  length = 36
FEATURE                Location/Qualifiers
misc_feature           1..36
                       note = Synthetic Polynucleotide
source                 1..36
                       mol_type = other RNA
                       organism = synthetic construct
SEQUENCE: 616
gtgaatataa gaactgaatt gcagccgaaa ggctgc                            36

SEQ ID NO: 617         moltype = RNA  length = 36
FEATURE                Location/Qualifiers
misc_feature           1..36
                       note = Synthetic Polynucleotide
source                 1..36
                       mol_type = other RNA
                       organism = synthetic construct
SEQUENCE: 617
attgagtgaa tgacaatttt gcagccgaaa ggctgc                            36

SEQ ID NO: 618         moltype = RNA  length = 36
```

```
FEATURE                Location/Qualifiers
misc_feature           1..36
                       note = Synthetic Polynucleotide
source                 1..36
                       mol_type = other RNA
                       organism = synthetic construct
SEQUENCE: 618
aatgacaatt ttgtaattta gcagccgaaa ggctgc                          36

SEQ ID NO: 619         moltype = RNA  length = 36
FEATURE                Location/Qualifiers
misc_feature           1..36
                       note = Synthetic Polynucleotide
source                 1..36
                       mol_type = other RNA
                       organism = synthetic construct
SEQUENCE: 619
gaattgatgt tgtaattaat gcagccgaaa ggctgc                          36

SEQ ID NO: 620         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 620
ttgaaaactc atacctccca gg                                         22

SEQ ID NO: 621         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 621
tttttttcca aacttttcct gg                                         22

SEQ ID NO: 622         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 622
tcatctatga agattgacca gg                                         22

SEQ ID NO: 623         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 623
ttgctgttat ttcagaaacc gg                                         22

SEQ ID NO: 624         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 624
aattcagttc ttatattcac gg                                         22

SEQ ID NO: 625         moltype = RNA  length = 22
FEATURE                Location/Qualifiers
misc_feature           1..22
                       note = Synthetic Polynucleotide
source                 1..22
                       mol_type = other RNA
                       organism = synthetic construct
SEQUENCE: 625
aaaattgtca ttcactcaat gg                                         22
```

-continued

```
SEQ ID NO: 626          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 626
taaattacaa aattgtcatt gg                                           22

SEQ ID NO: 627          moltype = RNA  length = 22
FEATURE                 Location/Qualifiers
misc_feature            1..22
                        note = Synthetic Polynucleotide
source                  1..22
                        mol_type = other RNA
                        organism = synthetic construct
SEQUENCE: 627
attaattaca acatcaattc gg                                           22
```